(12) United States Patent
Sedig et al.

(10) Patent No.: US 12,027,029 B2
(45) Date of Patent: Jul. 2, 2024

(54) KEEP OUT ZONE SYSTEM

(71) Applicant: Milwaukee Electric Tool Corporation, Brookfield, WI (US)

(72) Inventors: Steven B. Sedig, Fox Point, WI (US); Sara D. Linginfelter, Milwaukee, WI (US); Todd Andrew Zeilinger, Wauwatosa, WI (US); Samuel L. Lombardi, Milwaukee, WI (US); Benjamin T. Jones, St. Francis, WI (US); Scott Michael Cline, Menomonee Falls, WI (US); George I. Roudebush, Wauwatosa, WI (US); Jonathan E. Abbott, Milwaukee, WI (US); Carter H. Ypma, Milwaukee, WI (US); Nicholas J. LePar, West Allis, WI (US); Arhum M. Zafar, Chicago, IL (US); Hannah Elizabeth Phipps, Greenwood, IN (US); James C. Popp, Milwaukee, WI (US)

(73) Assignee: Milwaukee Electric Tool Corporation, Brookfield, WI (US)

( * ) Notice: Subject to any disclaimer, the term of this patent is extended or adjusted under 35 U.S.C. 154(b) by 55 days.

(21) Appl. No.: 17/853,270

(22) Filed: Jun. 29, 2022

(65) Prior Publication Data

US 2022/0406161 A1      Dec. 22, 2022

Related U.S. Application Data

(63) Continuation of application No. PCT/US2022/033425, filed on Jun. 14, 2022.

(Continued)

(51) Int. Cl.
    *G08B 21/04*    (2006.01)
    *G08B 25/01*    (2006.01)
    *G08B 25/14*    (2006.01)

(52) U.S. Cl.
    CPC ....... *G08B 21/0492* (2013.01); *G08B 21/043* (2013.01); *G08B 25/016* (2013.01); *G08B 25/14* (2013.01)

(58) Field of Classification Search
None
See application file for complete search history.

(56) References Cited

U.S. PATENT DOCUMENTS

| 4,146,887 A | 3/1979 | Magnante |
| 4,154,586 A | 5/1979 | Jones et al. |

(Continued)

FOREIGN PATENT DOCUMENTS

| CN | 107993389 | 5/2018 |
| CN | 107730428 | 4/2021 |

(Continued)

OTHER PUBLICATIONS

"Triax + EarthCam: The Future of Site Security Webinar," https://www.youtube.com/watch?v=79rgW5336XA, available at least as early as Nov. 18, 2021.

(Continued)

*Primary Examiner* — K. Wong
(74) *Attorney, Agent, or Firm* — Reinhart Boerner Van Deuren s.c.

(57) ABSTRACT

Various embodiments of a jobsite keep out zone system are provided. The system includes one or more detectors configured to determine when an intruder is within and/or is approaching a protected area. In response to the determination, one or more alarms and/or notifications are generated.

21 Claims, 80 Drawing Sheets

Related U.S. Application Data

(60) Provisional application No. 63/311,743, filed on Feb. 18, 2022, provisional application No. 63/290,433, filed on Dec. 16, 2021, provisional application No. 63/278,712, filed on Nov. 12, 2021, provisional application No. 63/256,210, filed on Oct. 15, 2021, provisional application No. 63/246,122, filed on Sep. 20, 2021, provisional application No. 63/241,321, filed on Sep. 7, 2021, provisional application No. 63/237,774, filed on Aug. 27, 2021, provisional application No. 63/233,021, filed on Aug. 13, 2021, provisional application No. 63/227,682, filed on Jul. 30, 2021, provisional application No. 63/223,246, filed on Jul. 19, 2021, provisional application No. 63/212,340, filed on Jun. 18, 2021.

(56) References Cited

U.S. PATENT DOCUMENTS

| | | |
|---|---|---|
| 4,155,358 A | 5/1979 | McAllister et al. |
| 4,326,514 A | 4/1982 | Eian |
| 5,297,544 A | 3/1994 | May et al. |
| 5,323,774 A | 6/1994 | Fehlauer |
| 5,659,296 A | 8/1997 | Debe et al. |
| 5,666,949 A | 9/1997 | Debe et al. |
| 6,118,382 A | 9/2000 | Hibbs et al. |
| 6,186,140 B1 | 2/2001 | Hoague |
| 6,216,693 B1 | 4/2001 | Rekow et al. |
| 6,417,774 B1 | 7/2002 | Hibbs et al. |
| 6,497,756 B1 | 12/2002 | Curado et al. |
| 6,700,497 B2 | 3/2004 | Hibbs et al. |
| 6,782,240 B1 | 8/2004 | Tabe |
| 6,868,697 B2 | 3/2005 | Baum |
| 6,995,665 B2 | 2/2006 | Appelt et al. |
| 7,073,351 B2 | 7/2006 | Baum et al. |
| 7,116,941 B1 | 10/2006 | Tabe |
| 7,271,720 B2 | 9/2007 | Tabe |
| 7,287,400 B1 | 10/2007 | Baum et al. |
| 7,442,237 B1 | 10/2008 | Gardner |
| 7,449,146 B2 | 11/2008 | Rakow et al. |
| 7,749,303 B2 | 7/2010 | Wright |
| 7,769,342 B2 | 8/2010 | Tabe |
| 7,860,662 B2 | 12/2010 | Parham et al. |
| 7,872,575 B2 | 1/2011 | Tabe |
| 7,875,100 B2 | 1/2011 | Wright |
| 7,878,199 B2 | 2/2011 | Ging et al. |
| 7,894,069 B2 | 2/2011 | Duncan et al. |
| 7,906,223 B2 | 3/2011 | Rakow et al. |
| 7,967,013 B2 | 6/2011 | Ging et al. |
| 8,067,110 B2 | 11/2011 | Rakow et al. |
| 8,070,205 B2 | 12/2011 | Schermerhorn et al. |
| 8,085,144 B2 | 12/2011 | Appelt et al. |
| 8,099,054 B2 | 1/2012 | Tabe |
| 8,136,524 B2 | 3/2012 | Ging et al. |
| 8,225,782 B2 | 7/2012 | Rakow et al. |
| 8,328,903 B2 | 12/2012 | Parham et al. |
| 8,336,543 B2 | 12/2012 | Holmquist-Brown et al. |
| 8,365,723 B2 | 2/2013 | Poirier et al. |
| 8,459,200 B2 | 6/2013 | Battiato et al. |
| 8,506,902 B2 | 8/2013 | Rakow et al. |
| 8,616,205 B2 | 12/2013 | Tobias et al. |
| 8,698,634 B2 | 4/2014 | Guedes Lopes Da Fonseca et al. |
| 8,859,995 B2 | 10/2014 | Liu et al. |
| 8,941,833 B2 | 1/2015 | Kanukurthy et al. |
| 8,955,515 B2 | 2/2015 | Rakow et al. |
| 9,011,584 B2 | 4/2015 | Tobias et al. |
| 9,044,626 B2 | 6/2015 | Truex et al. |
| 9,079,049 B2 | 7/2015 | Tobias et al. |
| 9,283,411 B2 | 3/2016 | Larsen et al. |
| 9,311,801 B2 | 4/2016 | Cholhan et al. |
| 9,322,684 B2 | 4/2016 | Pike |
| 9,333,378 B2 | 5/2016 | Ishikawa et al. |
| 9,358,494 B2 | 6/2016 | Frankel et al. |
| 9,442,073 B2 | 9/2016 | Joly et al. |
| 9,504,859 B2 | 11/2016 | Ding et al. |
| 9,569,951 B2 | 2/2017 | Cholhan et al. |
| 9,642,978 B2 | 5/2017 | Ging et al. |
| 9,751,038 B2 | 9/2017 | Frankel et al. |
| 9,848,666 B1 | 12/2017 | Egeland et al. |
| 9,901,125 B2 | 2/2018 | Insley et al. |
| 9,922,536 B2 | 3/2018 | Cholhan et al. |
| 9,978,247 B2 | 5/2018 | Alampallam et al. |
| 10,065,055 B2 | 9/2018 | Larsen |
| 10,140,841 B2 | 11/2018 | Cholhan et al. |
| 10,206,447 B2 | 2/2019 | Egeland et al. |
| 10,213,629 B2 | 2/2019 | Tobias |
| 10,235,857 B2 * | 3/2019 | Jones ............... H04W 4/80 |
| 10,269,232 B2 | 4/2019 | Rachakonda et al. |
| 10,349,686 B2 | 7/2019 | Insley et al. |
| 10,373,480 B2 | 8/2019 | Cholhan et al. |
| 10,515,521 B2 | 12/2019 | Klein et al. |
| 10,535,242 B2 | 1/2020 | Rahman et al. |
| 10,535,249 B2 | 1/2020 | Cholhan et al. |
| 10,575,579 B2 | 3/2020 | Egeland et al. |
| 10,576,407 B2 | 3/2020 | Ding et al. |
| 10,646,732 B2 | 5/2020 | Rachapudi et al. |
| 10,830,392 B2 * | 11/2020 | Frederick ............ H03K 17/9502 |
| 2001/0013347 A1 | 8/2001 | Rekow et al. |
| 2001/0024949 A1 | 9/2001 | Yanagida et al. |
| 2004/0062682 A1 | 4/2004 | Rakow et al. |
| 2005/0001728 A1 | 1/2005 | Appelt et al. |
| 2007/0094268 A1 | 4/2007 | Tabe |
| 2010/0189922 A1 | 7/2010 | Rakow et al. |
| 2011/0232646 A1 | 9/2011 | Ho et al. |
| 2012/0055815 A1 | 3/2012 | Truex et al. |
| 2012/0176237 A1 | 7/2012 | Tabe |
| 2012/0296974 A1 | 11/2012 | Tabe |
| 2013/0278410 A1 * | 10/2013 | Smith ............... G08B 25/00 |
| | | 340/517 |
| 2015/0346174 A1 | 12/2015 | Beaulieu et al. |
| 2015/0347600 A1 | 12/2015 | Tabe |
| 2016/0174626 A1 | 6/2016 | Mazzarolo et al. |
| 2016/0213954 A1 | 7/2016 | Ding et al. |
| 2016/0317771 A1 | 11/2016 | Klee et al. |
| 2017/0080261 A1 | 3/2017 | Sutton et al. |
| 2017/0169533 A1 | 6/2017 | O'Brien |
| 2017/0203068 A1 | 7/2017 | Ging et al. |
| 2017/0206534 A1 | 7/2017 | O'Brien |
| 2017/0243457 A1 | 8/2017 | Milbrand |
| 2017/0281991 A1 | 10/2017 | Wang et al. |
| 2017/0309152 A1 | 10/2017 | Dinkins |
| 2017/0312555 A1 | 11/2017 | Olmsted et al. |
| 2018/0028846 A1 | 2/2018 | Hur et al. |
| 2018/0067593 A1 * | 3/2018 | Tiwari ............... G08B 13/22 |
| 2018/0295188 A1 | 10/2018 | Bahners et al. |
| 2018/0311517 A1 | 11/2018 | Patil et al. |
| 2018/0338561 A1 | 11/2018 | Destrian et al. |
| 2018/0369616 A1 | 12/2018 | Dobbing |
| 2019/0064750 A1 | 2/2019 | Awiszus et al. |
| 2019/0143154 A1 | 5/2019 | Gangadhar et al. |
| 2019/0242861 A1 | 8/2019 | Croll et al. |
| 2019/0262573 A1 | 8/2019 | McKenna et al. |
| 2019/0275359 A1 | 9/2019 | Shen et al. |
| 2019/0313710 A1 | 10/2019 | Insley et al. |
| 2019/0333178 A1 * | 10/2019 | Cheng ............... G06Q 50/265 |
| 2019/0355232 A1 | 11/2019 | Cholhan et al. |
| 2019/0358473 A1 | 11/2019 | Szasz et al. |
| 2020/0179859 A1 | 6/2020 | Ding et al. |
| 2020/0179903 A1 | 6/2020 | Beiermann et al. |
| 2020/0215364 A1 | 7/2020 | Webb et al. |

FOREIGN PATENT DOCUMENTS

| | | |
|---|---|---|
| JP | 2005-031831 | 2/2005 |
| JP | 2007-004619 | 1/2007 |
| KR | 10-2012-0096977 | 9/2012 |
| KR | 10-2017-0138862 | 12/2017 |
| WO | WO09141474 | 11/2009 |
| WO | WO14049187 | 4/2014 |
| WO | WO15131876 | 9/2015 |
| WO | WO16106556 | 7/2016 |
| WO | WO16115707 | 7/2016 |
| WO | WO17002123 | 1/2017 |

(56) References Cited

FOREIGN PATENT DOCUMENTS

| WO | WO17085640 | 5/2017 |
|----|------------|--------|
| WO | WO17135945 | 8/2017 |
| WO | WO19215580 | 11/2019 |

OTHER PUBLICATIONS

"EarthCam and Triax—The Next Level of Access Control for Construction," https://www.youtube.com/watch?v=xBTbWSyPN6o, available at least as early as Oct. 22, 2019.

Irisys Vector 4D, people counting system: https://www.youtube.com/watch?v=Cm6rn_M63SDs, available at least as early as Dec. 21, 2020.

XOVIS PC2R Sensor: https://shop.verncogroup.com/products/xovis-pc2r, available at least as early as Sep. 23, 2020, per Wayback Machine.

International Search Report and Written Opinion for International Application No. PCT/US2022/033425, dated Oct. 11, 2022, 11 pages.

* cited by examiner

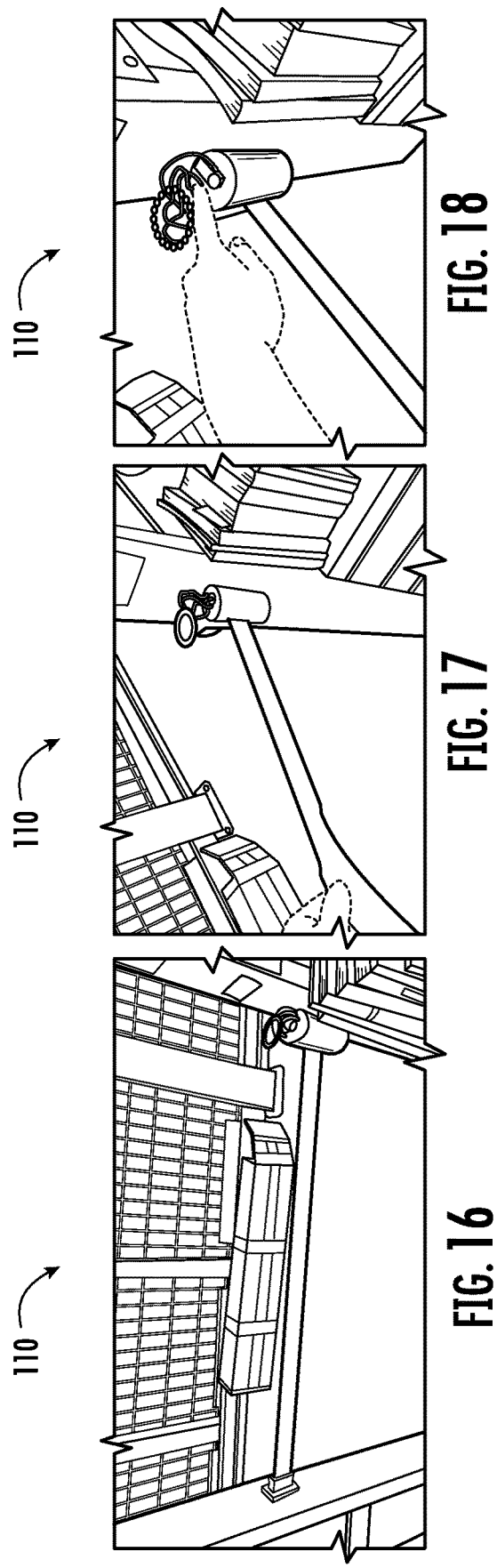

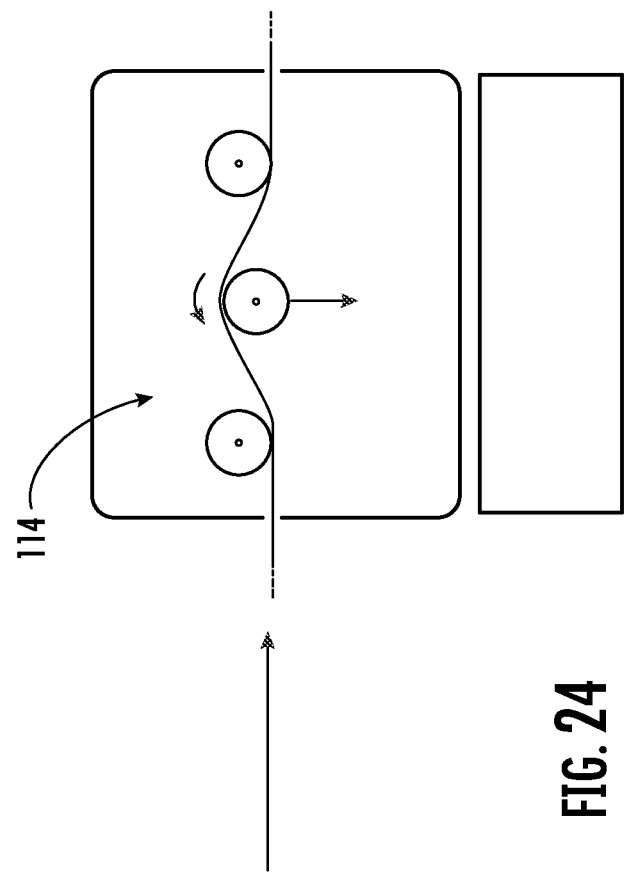
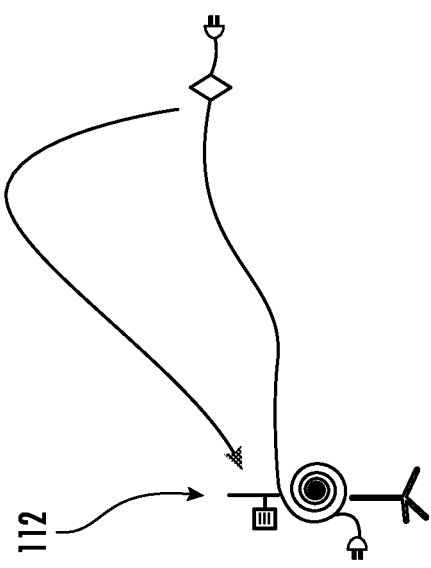
FIG. 24

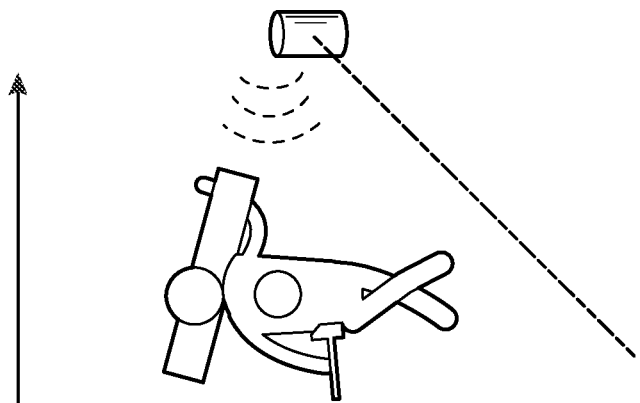
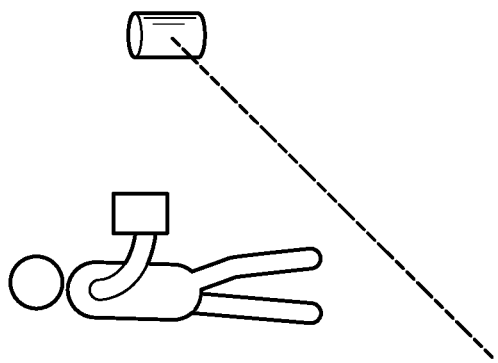
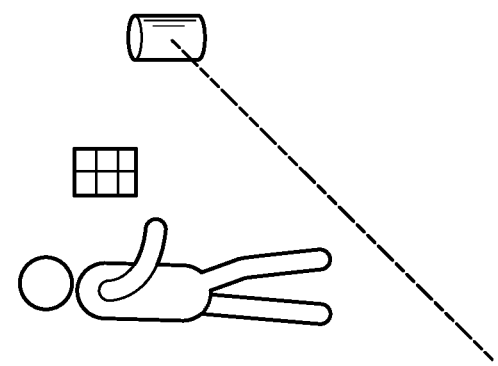
FIG. 28

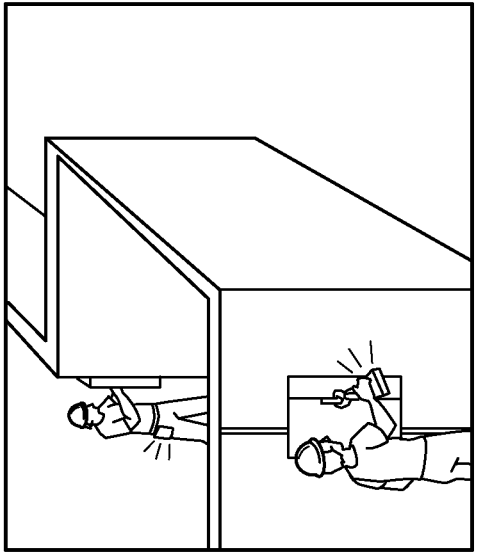
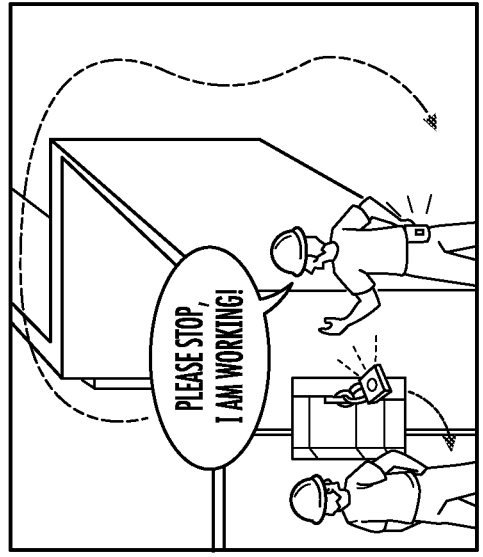
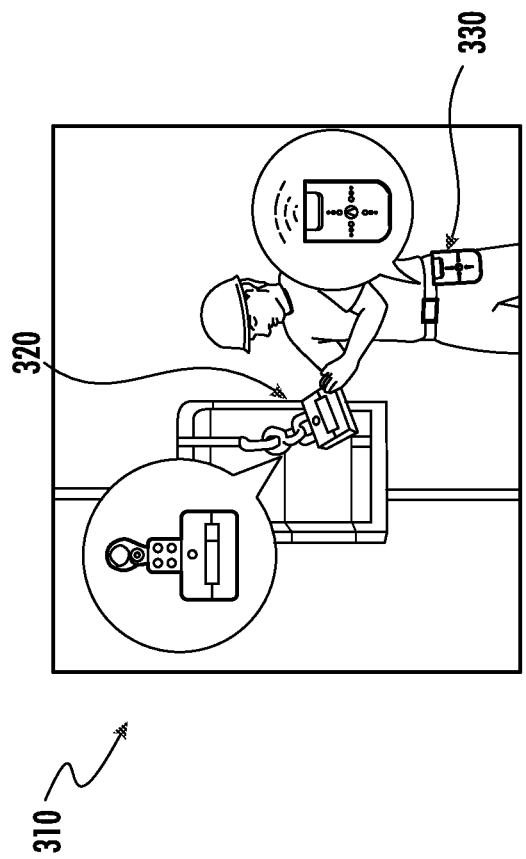
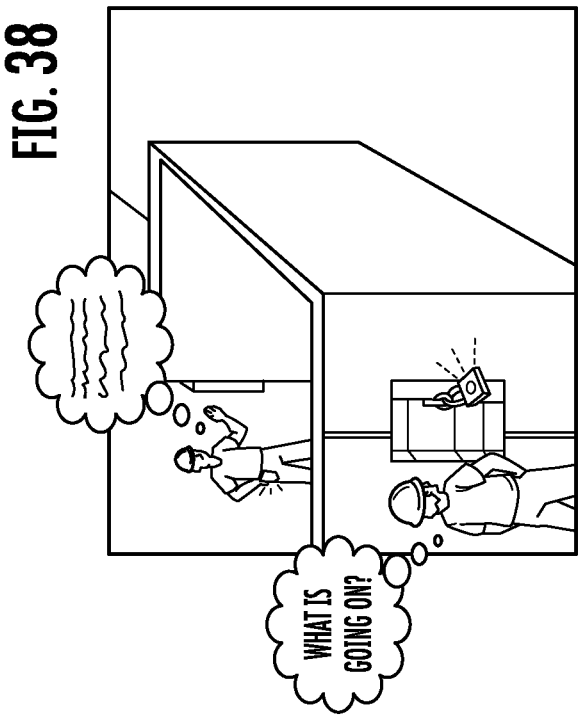

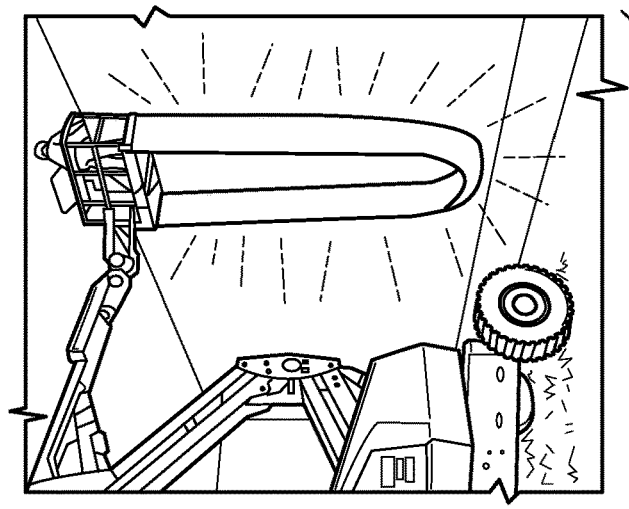
FIG. 82
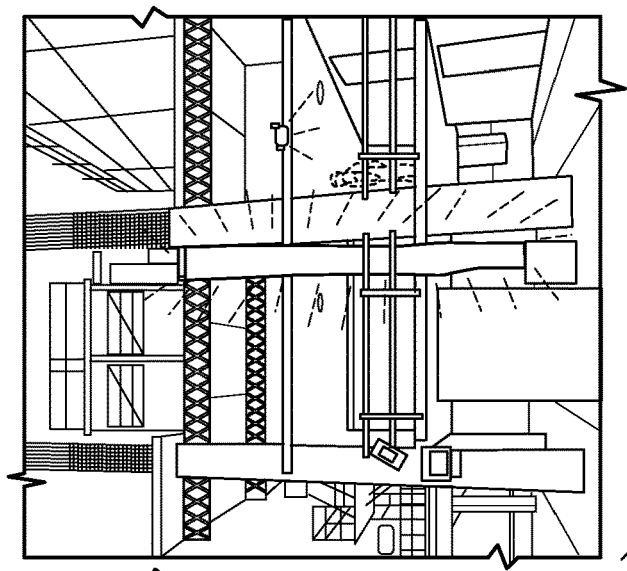
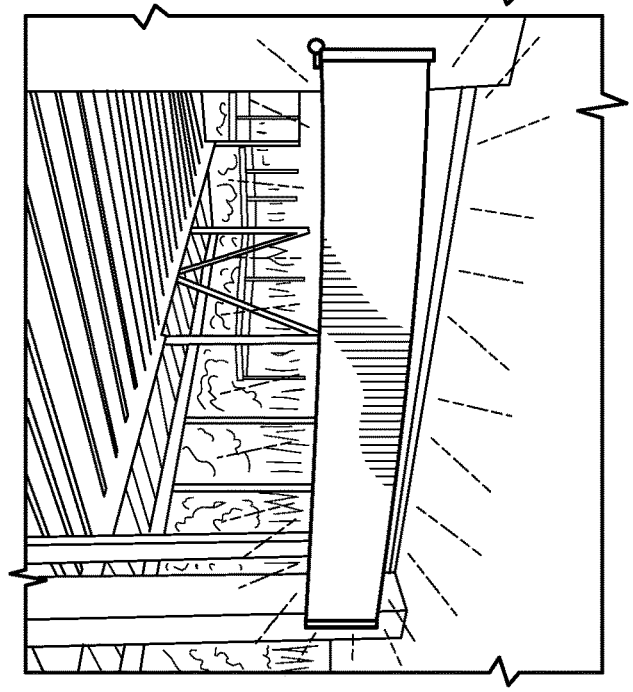
FIG. 81

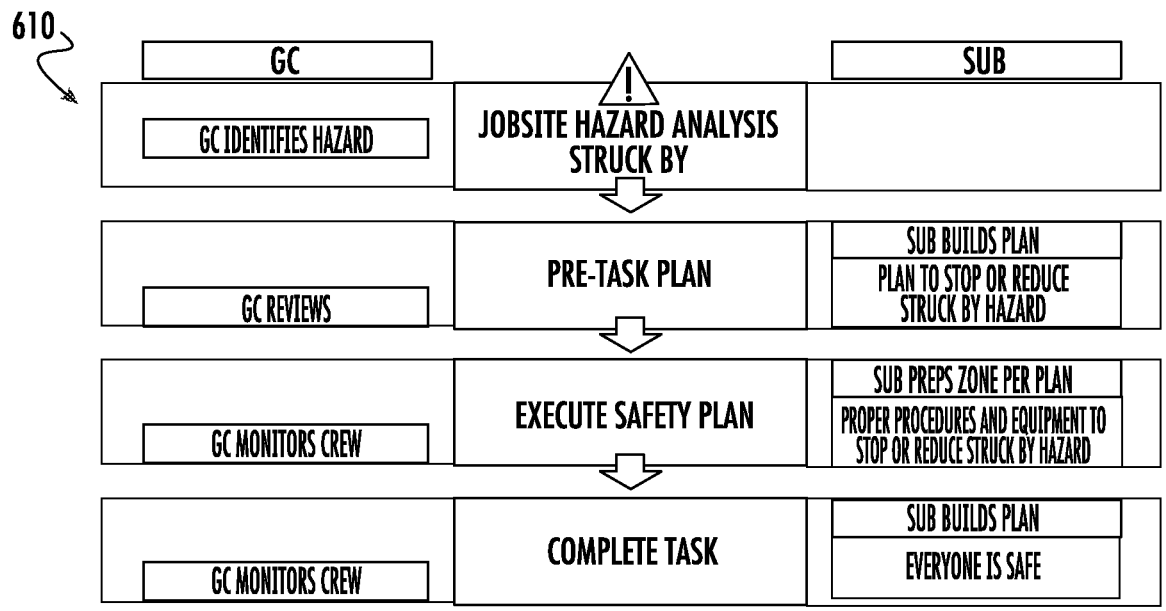
FIG. 98
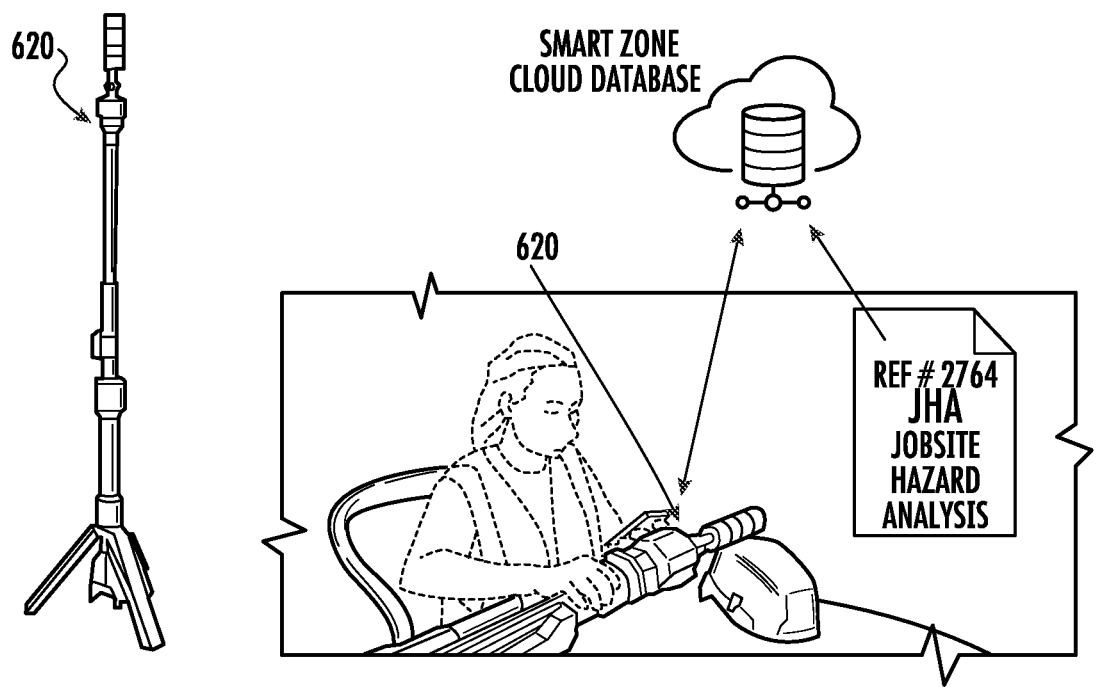
FIG. 99
FIG. 100

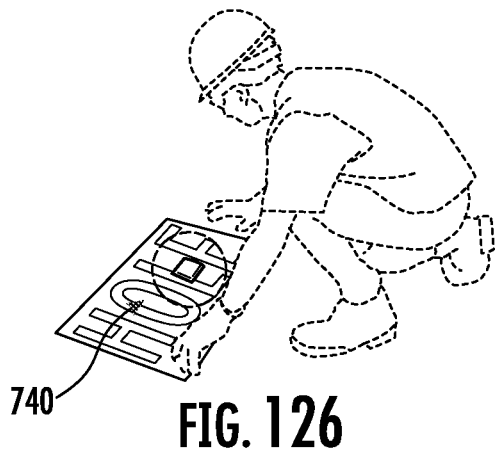
740  FIG. 126
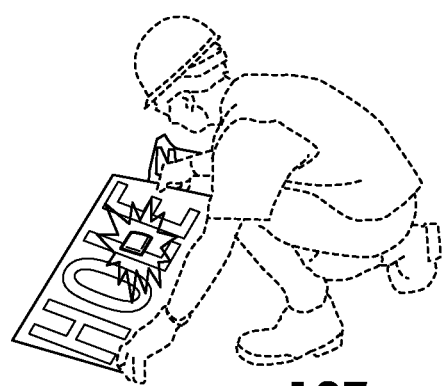
FIG. 127
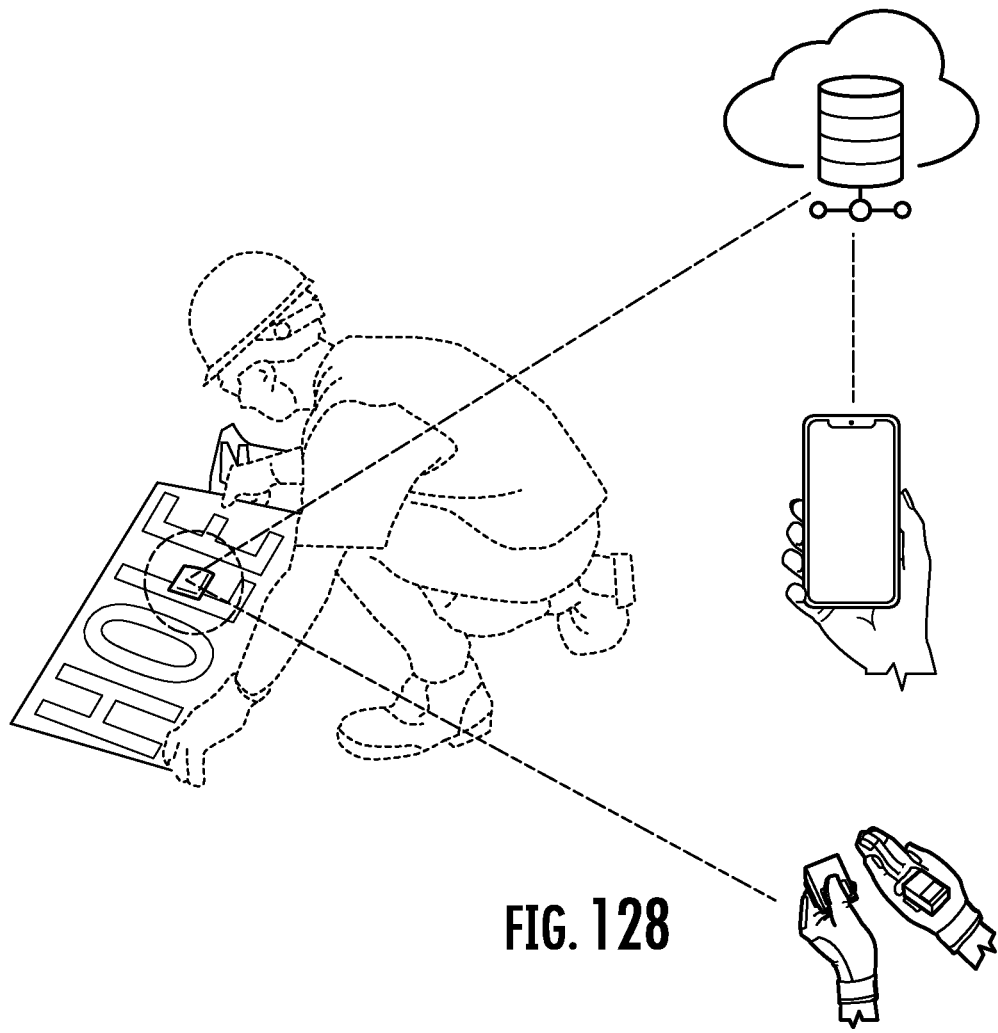
FIG. 128

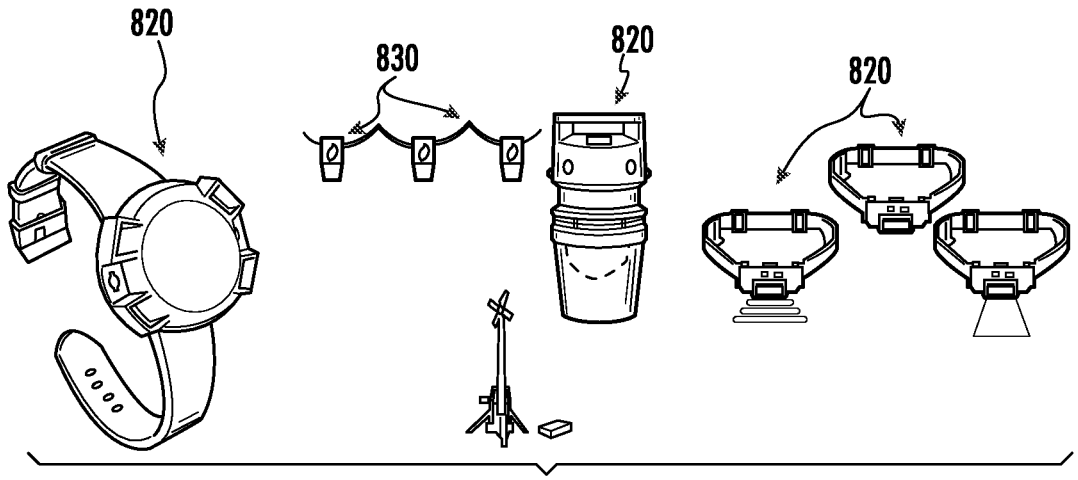

FIG. 134

| | WARNING ←――――――――――――――――――――――→ FULL ALERT | | | | |
|---|---|---|---|---|---|
| ENTERING/IN A ZONE | TOOL LIGHT FLASHES | TOOL TRIGGER PULL DELAY | TOOL DOES NOT WORK | | |
| | HEADLAMP FLASHES | TOOL RUMBLE/ REV [POSSIBLE] | FUTURE TOOLS MAY HAVE HAPTIC FEATURE USE TOOLS PRIMARY BRUSHLESS MOTOR FOR HAPTICS | HEADLAMP FLASHES & BEEPS | SITE LIGHTING FLASHES &/OR BEEPS |
| SOMEONE HAS ENTERED MY ZONE | TOOL LIGHT FLASHES | TOOL TRIGGER PULL DELAY | TOOL DOES NOT WORK | | |
| | HEADLAMP FLASHES | TOOL RUMBLE/ REV [POSSIBLE] | | HEADLAMP FLASHES & BEEPS | SITE LIGHTING FLASHES &/OR BEEPS |

FIG. 135

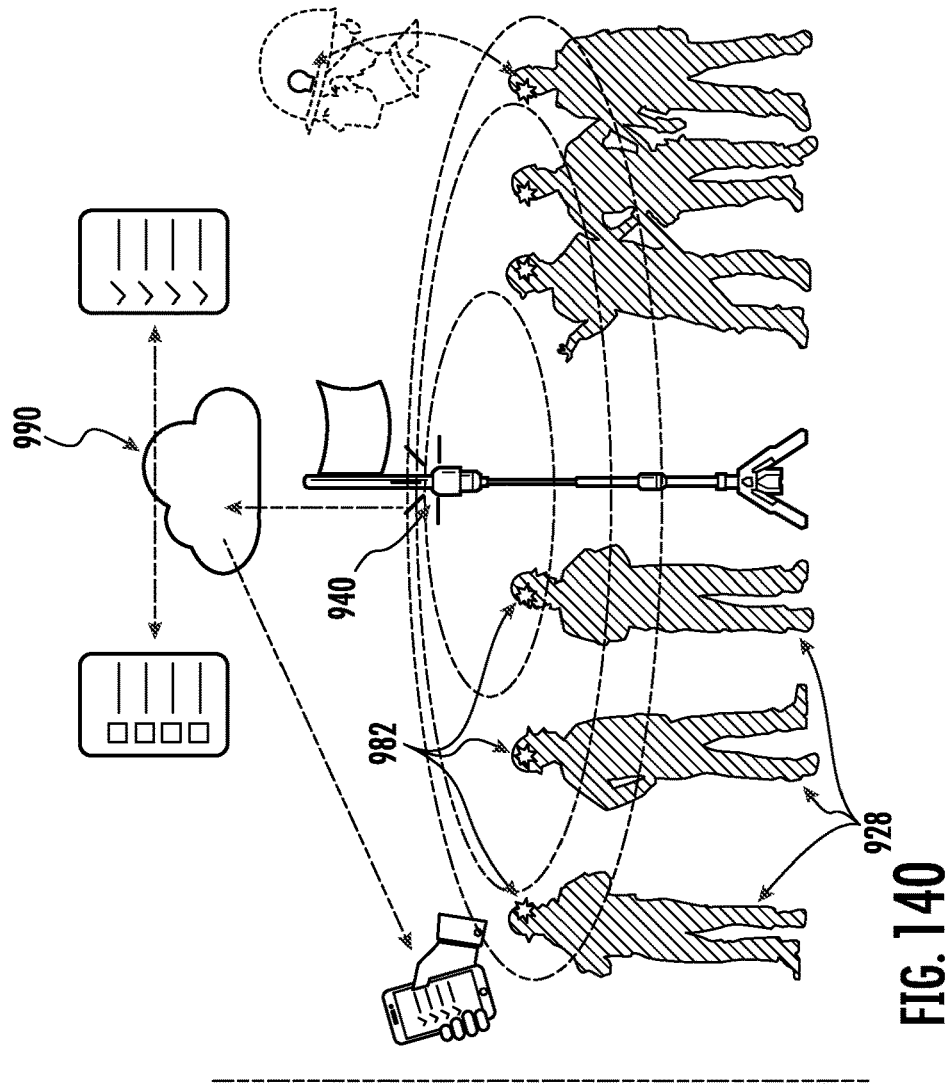
FIG. 140
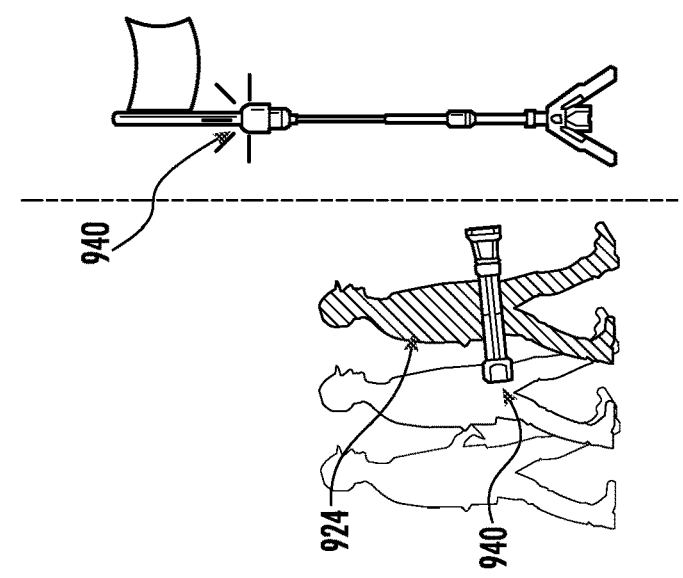

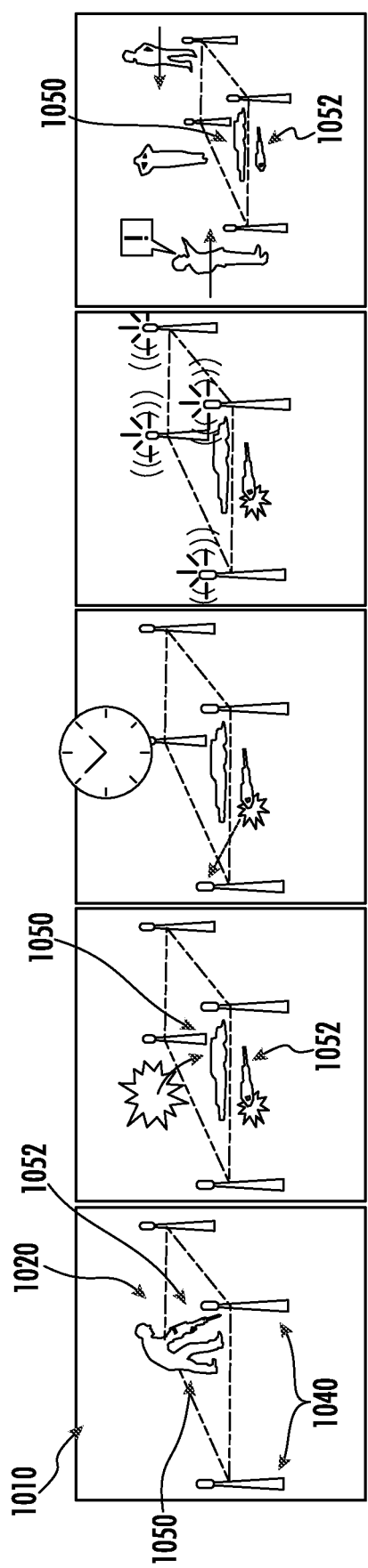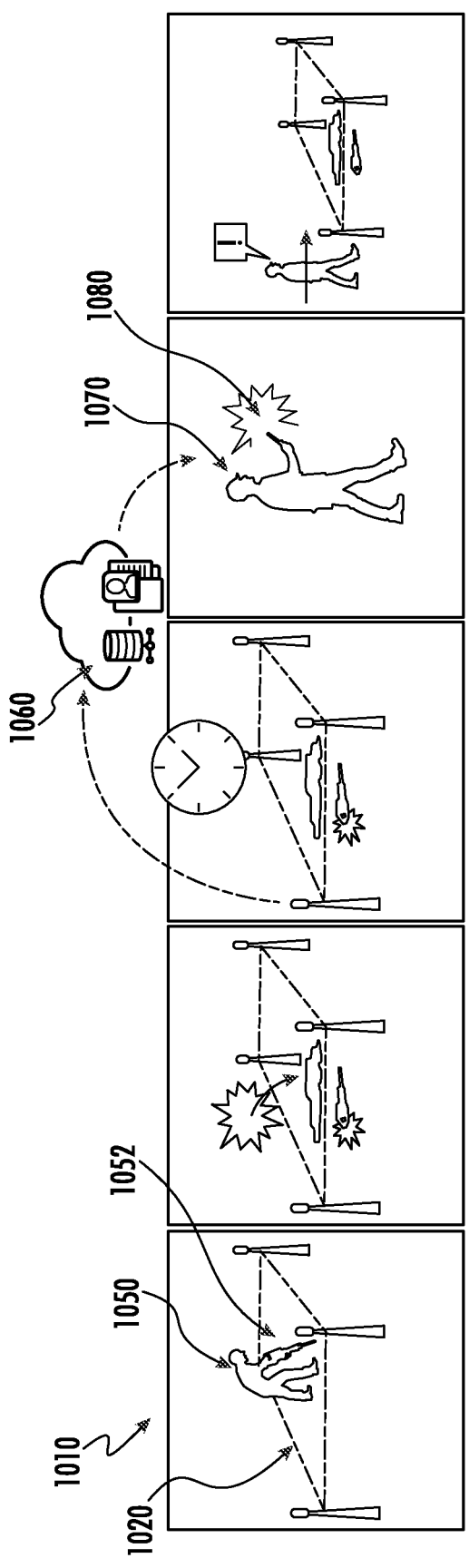

KEEP OUT ZONE SYSTEM

CROSS-REFERENCE TO RELATED PATENT APPLICATIONS

The present application is a continuation of International Application No. PCT/US2022/033425, filed Jun. 14, 2022, which claims the benefit of and priority to U.S. Provisional Application No. 63/311,743, filed on Feb. 18, 2022, U.S. Provisional Application No. 63/290,433, filed on Dec. 16, 2021, U.S. Provisional Application No. 63/278,712, filed on Nov. 12, 2021, U.S. Provisional Application No. 63/256,210, filed on Oct. 15, 2021, U.S. Provisional Application No. 63/246,122, filed on Sep. 20, 2021, U.S. Provisional Application No. 63/241,321, filed on Sep. 7, 2021, U.S. Provisional Application No. 63/237,774, filed on Aug. 27, 2021, U.S. Provisional Application No. 63/233,021, filed on Aug. 13, 2021, U.S. Provisional Application No. 63/227,682, filed on Jul. 30, 2021, U.S. Provisional Application No. 63/223,246, filed on Jul. 19, 2021, and U.S. Provisional Application No. 63/212,340, filed on Jun. 18, 2021, each of which is incorporated herein by reference in its entirety.

BACKGROUND OF THE INVENTION

The present disclosure is directed generally to the field of monitoring systems. The present disclosure relates specifically to a safety monitoring system for a worksite.

SUMMARY OF THE INVENTION

Various embodiments the invention relate to a jobsite or worksite keep out zone system.

One embodiment of the invention relates to a safety monitoring system including a first device, a second device, and a third device. The first device is configured to generate an alert providing an indication of a protected area on a construction site, and the alert comprises audio and/or visual elements. The second device is configured to generate an electronic signal in response to detecting an intrusion to the protected area. The third device is remote from the second device, and the third device is configured to receive a notification that the intrusion was detected in the protected area.

Another embodiment of the invention relates to a safety monitoring system including a first device configured to generate an electronic signal in response to detecting an intrusion to a protected area on a construction site, and an electric tool. The electric tool is configured to receive a notification that the intrusion was detected in the protected area, and generate a safety alarm in response to the detection of the intrusion.

Another embodiment of the invention relates to a safety monitoring system including a first monitoring device and a central server. The first monitoring device is configured to measure an atmospheric condition, to monitor the presence of a worker within a protected area on a construction site, and to generate a notification indicating the measurement of the atmospheric condition and the presence of the worker. The central server is configured to receive the notification from the first monitoring device, analyze the notification, and transmit an alarm to the worker in response to the analyzing of the notification.

Another embodiment of the invention relates to a method for monitoring a safety zone at a construction site. The method includes receiving a first signal indicating a first number of people in a protected area on a construction site, receiving a second signal indicating the occurrence of an emergency event that corresponds to the protected area, receiving a third signal indicating a second number of the people that were in the protected area, and determining whether the protected area is evacuated by comparing the first number to the second number.

Another embodiment of the invention relates to a safety monitoring system. The safety monitoring system includes a plurality of monitoring devices. The plurality of monitoring devices are positioned to detect an intrusion within a protected area at a construction site. A first device of the plurality of monitoring devices is configured to generate an electronic signal in response to the detection of an intrusion to the protected area. A notification is generated in response to determining that an intrusion was detected.

In various embodiments, a computing device remote from the first device receives a notification from the first device that an intruder was detected in the protected area. In a specific embodiment, the notification sent to the computing device includes data that identifies an identify of the intruder. In a specific embodiment, the notification is sent to a device associated with the intruder. In various embodiments, one of the monitoring devices includes a laser transmitter and another of the monitoring devices includes a light detector.

Another embodiment of the invention relates to a method of monitoring a safety area. The method includes arranging a plurality of monitoring devices to monitor a protected area at a construction site. The method further includes determining whether a notification should be generated based at least in part on analyzing an electronic signal. The method further includes sending a notification.

Another embodiment of the invention relates to a safety monitoring system including a plurality of portable electronic monitoring devices configured to monitor a plurality of protected areas at a construction site, and a central server. A first monitoring device of the plurality of monitoring devices is configured to measure an atmospheric condition, to monitor the presence of a plurality of workers within a first protected area of the plurality of protected areas, and to generate a signal indicating the measurement of the atmospheric condition and/or the presence of the workers. The central server is configured to receive the signal from the first monitoring device, analyze the signal, and generate an alarm based on the analyzing of the signal.

In various embodiments, the central server is further configured to generate a signal to a remote personal device in response to generating the alarm, and the remote personal device is associated with a person responsible for the first protected area. In various embodiments, the central server is further configured to generate an alarm in response to determining at least one worker is within the first protected area. In various embodiments, the central server is configured to not generate an alarm in response to determining that no workers are within the first protected area (e.g., the central server only generates an alarm if at least one person is within the first protected area).

In various embodiments, the safety monitoring system includes a plurality of ID devices each configured to couple to a worker of the plurality of workers. Each ID device of the plurality of ID devices is configured to provide identifying information to the first monitoring device, and the identifying information uniquely identifies the respective ID device.

According to another embodiment of the invention, a safety monitoring system includes a plurality of portable electronic monitoring devices configured to monitor a plurality of protected areas at a construction site, and a central server. A first monitoring device of the plurality of monitoring devices is configured to monitor the presence of a plurality of workers within a first protected area of the plurality of protected areas, and to generate a signal indicating the presence of the workers. The central server is configured to receive the signal from the first monitoring device, to analyze the signal and generate an alarm based on the analyzing of the signal.

In various embodiments, the central server is configured to receive a second signal indicating a count of the workers, and the central server is further configured to compare the count of the workers to the monitoring of the workers to determine whether any workers are unaccounted for (e.g., not present for the count). In various embodiments, the workers are each wearing an ID device of a plurality of ID devices, and the second signal is received from a personal electronic device, such as a cell phone, configured to receive a counting signal from each of the plurality of ID devices.

Additional features and advantages will be set forth in the detailed description which follows, and, in part, will be readily apparent to those skilled in the art from the description or recognized by practicing the embodiments as described in the written description included, as well as the appended drawings. It is to be understood that both the foregoing general description and the following detailed description are exemplary.

The accompanying drawings are included to provide further understanding and are incorporated in and constitute a part of this specification. The drawings illustrate one or more embodiments and, together with the description, serve to explain principles and operation of the various embodiments.

BRIEF DESCRIPTION OF THE DRAWINGS

This application will become more fully understood from the following detailed description, taken in conjunction with the accompanying figures, wherein like reference numerals refer to like elements in which:

FIGS. 13-31 depict various aspects of the safety monitoring system of FIG. 1, according to an exemplary embodiment.

FIGS. 38-45 depict various aspects of a safety monitoring system, according to an exemplary embodiment.

FIGS. 46-83 depict various aspects of one or more safety monitoring systems, according to exemplary embodiments.

FIGS. 98-112 provide details regarding various aspects and embodiments related to a safety monitoring system.

FIGS. 113-132 provide details regarding various aspects and embodiments related to safety monitoring system.

FIGS. 133-137 provide details regarding various aspects and embodiments related to safety monitoring system.

FIGS. 138-142 provide details regarding various aspects and embodiments related to safety monitoring system.

FIGS. 143-152 provide details regarding various aspects and embodiments related to a safety monitoring system.

DETAILED DESCRIPTION

Figure 1:
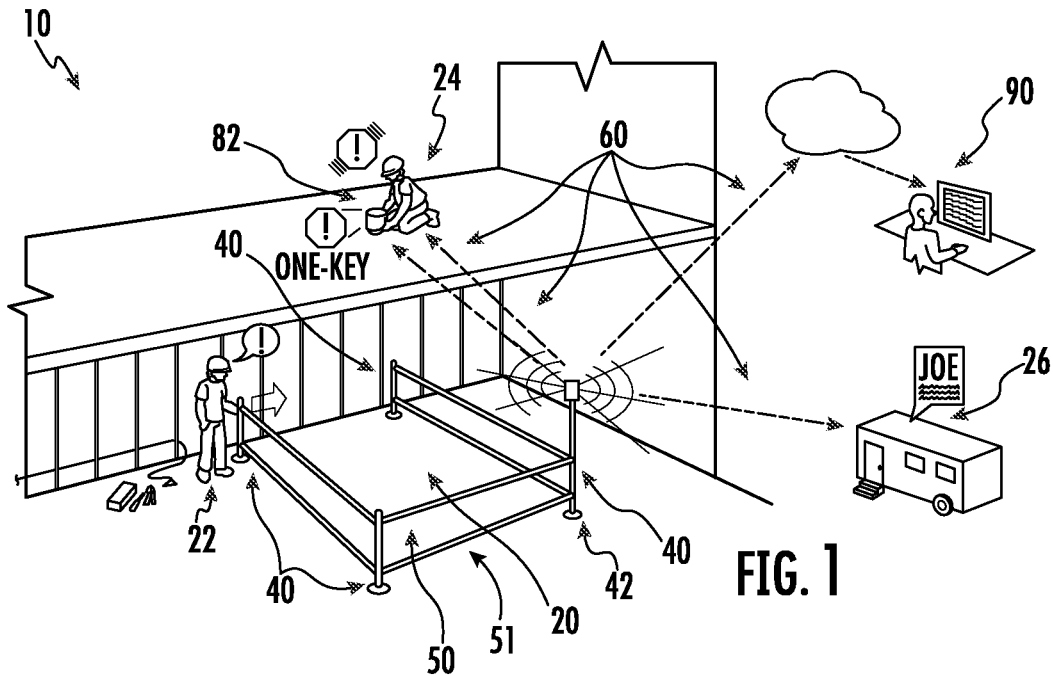
FIG. 1 depicts an exemplary embodiment of a safety monitoring system for a worksite, according to an exemplary embodiment.

Referring generally to the figures, various embodiments of a computer-based keep out zone system for a worksite are provided. One of the goals of the keep out zone system is to bring a protected area to life and notify stakeholders to keep them safe. Benefits of the computer-based keep out zone system include reducing the likelihood that someone is in a hazardous area, reducing the likelihood that people entering or leaving protected areas goes unnoticed or ignored, and reducing the likelihood that people congregate in a hazardous area (e.g., where there is a risk they may be struck). Another benefit of the computer-based keep out zone system is that they can be dynamically adjusted both in terms of their location, and in terms of the alarms generated (e.g., the severity of the alarm could be escalated or reduced based on changed circumstances within the protected area).

As explained in more detail in the attached figures, in one embodiment, a laser beam identifies the boundary of the keep out zone, and if a user passes through a laser, a notification (e.g., loud sound, light, Wi-Fi notification, etc.) or alarm is sounded. In another example, users get notifications that they are leaving the safe zone and/or entering a dangerous zone. In such embodiments, users may have a receiver device (e.g., such as a watch, a helmet, eyewear, a smart phone, etc.) that communicates with the keep out zone system. This helps make the protected area more safe by improving situational awareness of peopled around the protected area. In particular, the person approaching intruding into the protected area is quickly alerted that they are entering an area with increased risks/dangers, and people working within the protected area receive notifications that unauthorized people may be nearby and/or in danger.

Sending signals to personal receiving devices enables the keep out system to send personalized messages to different individuals. For example, the person monitoring the protected area can be alerted when new people are in the protected area and when people leave the protected area. As another example, intrusions into the protected area(s) may be logged in a central database and the data is used to improve overall safety at the worksite.

In another embodiment, the keep out zone system includes multiple protective devices transmitting ultra-wideband signals that are placed around an area. In a specific embodiment the protective devices are pucks. If a user with a receiver comes within a certain distance to the area, they get a personal notification. If a user passes by a protective device (e.g., a short amount of time the signal is detected), then there is no notification. If a user is walking towards a protective device (a signal is detected for a predetermined amount of time and/or the signal is getting stronger and/or signals from multiple protective devices are received) then the user is notified. In another embodiment, a capacitive sensor or motion sensor is applied to a safety lock or a lock box and if the lock is tampered with, broken, etc., the user gets a notification.

Figure 2:
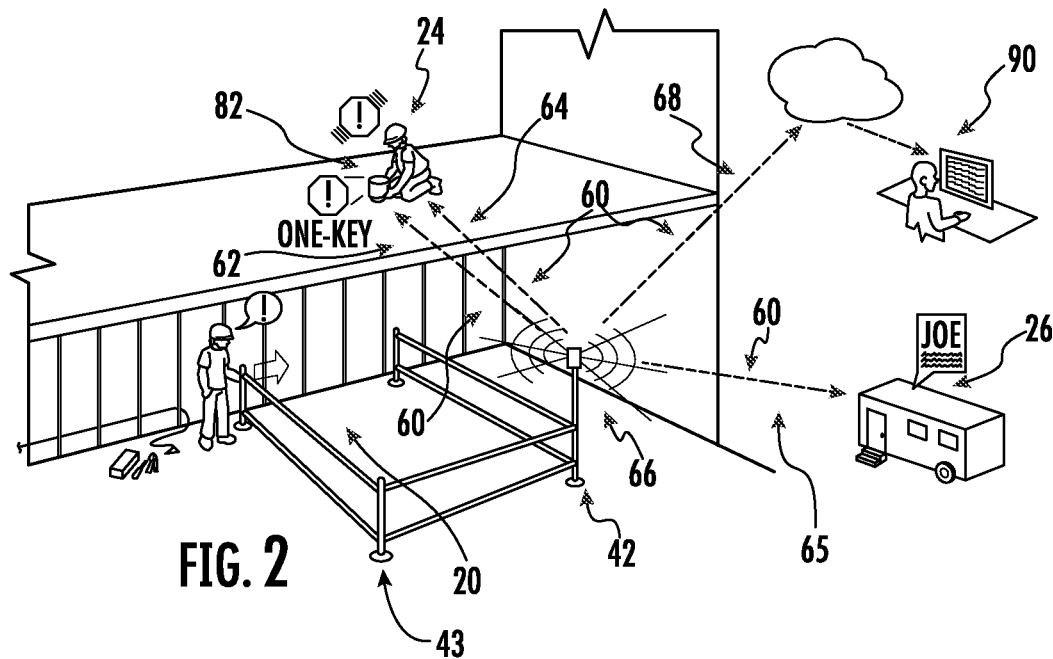
FIG. 2 depicts the safety monitoring system of FIG. 1, according to an exemplary embodiment.

Referring to FIGS. 1-2, a safety monitoring system, shown as a keep out zone system 10, is shown according to an exemplary embodiment. In various embodiments keep out zone system 10 is utilized to monitor one or more protected areas 20 at worksites, such as construction sites.

Keep out zone system 10 includes one or more monitoring devices, shown as portable electronic monitoring devices 40. Portable electronic monitoring devices 40 are arranged to monitor and protect protected area 20, such as by individual 24 in charge of protected area 20 placing portable electronic monitoring devices 40 at various locations around protected area 20. In various embodiments, portable electronic monitoring devices 40 can be arranged and activated at new locations quickly. Further, the distance between portable electronic monitoring devices 40, and thus the area and/or shape of protected area 20, are dynamically adjustable and permit large distances between portable electronic monitoring devices 40 (e.g., 100+ feet).

In on example, keep out zone system 10 includes a first device 42, a second device 43, and a third device (e.g., database 90, personal device 80). In various embodiments, the first device 42 is configured to generate an alert providing an indication of a protected area on a construction site, the alert including audio and/or visual elements (e.g., a flashing light), the second device 43 is configured to generate an electronic signal in response to detecting an intrusion to the protected area, the third device 80, 90 is remote from the second device 43, and the third device is configured to receive a notification that the intrusion was detected in the protected area. In various embodiments, second device 43 is configured to emit light (e.g., a laser) along a periphery of the protected area, and the first device 42 includes a detector, such as photodiode 46, configured to detect the laser.

In various embodiments, the third device is remote from the protected area (e.g., database 90 is remote from the protected area; personal device 80 associated with safety monitor individual 26 is remote from the protected area). In various embodiments, the electronic signal sent from the second device 43 (e.g., via a personal device 80) includes a text message and/or the notification sent to safety monitor individual 26 includes the text message. In various embodiments, the text message includes information identifying an intruder that caused the intrusion.

Figure 6:
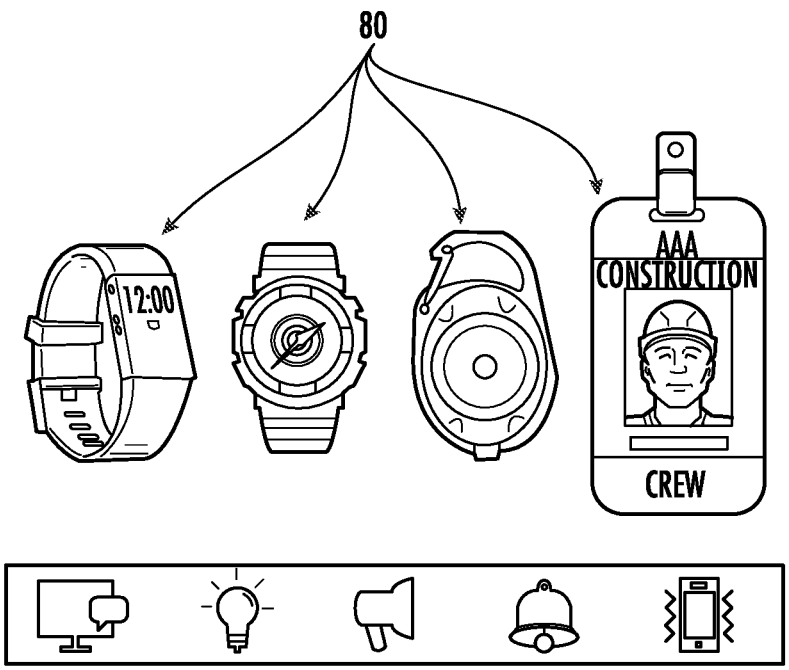
FIG. 6 depicts various personal devices that receive input from the safety monitoring system of FIG. 1, according to an exemplary embodiment.
Figure 7:
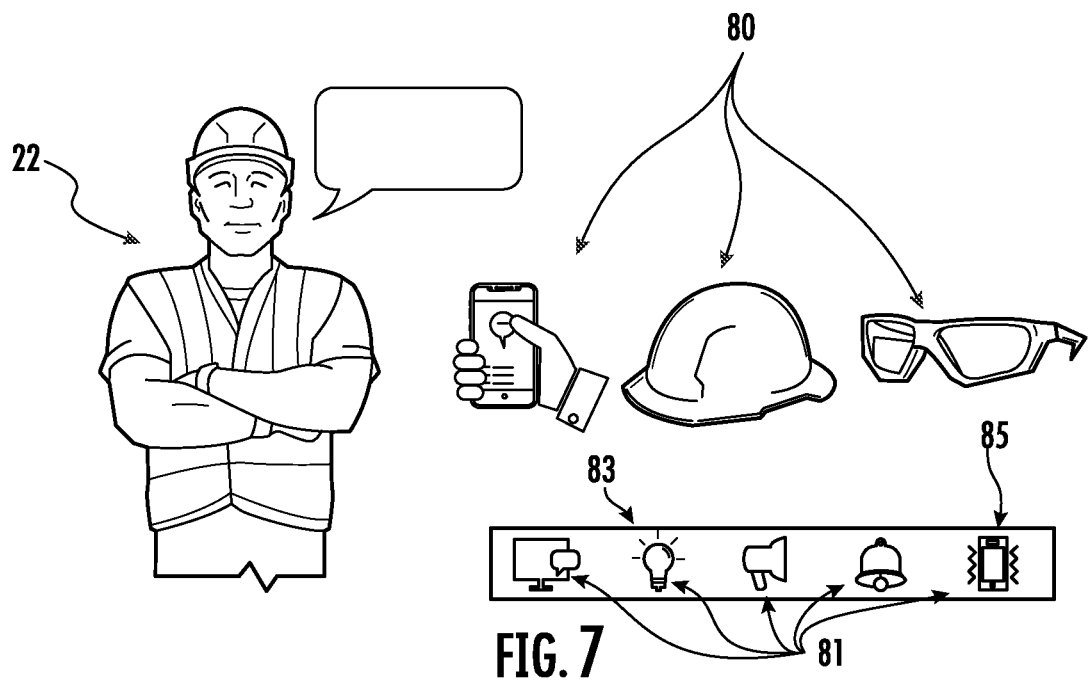
FIG. 7 depicts various personal devices that receive input from the safety monitoring system of FIG. 1, according to an exemplary embodiment.

In various embodiments, the third device receiving the notification includes a hard hat (e.g., see FIG. 7). In various embodiments, the personal device 80 (e.g., a hard hat) includes notification devices 81 (e.g, haptic, alarm-generating, light generating), such as lighting element 83 and/or haptic element 85 configured to vibrate and/or move. For example, the personal device 80 (e.g., a hard hat) includes a lighting element 83 configured to emit a light in response to receiving the notification that the intrusion was detected in the protected area (see FIGS. 6-7). As another example, personal device 80 (e.g., a hard hat) includes a haptic element 85 configured to vibrate in response to receiving the notification that the intrusion was detected in the protected area.

Protected area 20 is around a dangerous area. In various embodiments, protected area 20 is placed around a hole being excavated, a building being erected, a perimeter of a building (to protect from objects being dropped), a perimeter of a roof (to protect against individuals and/or objects falling off the roof), holes on an interior of a building (e.g., to protect people from falling down holes or shafts), and/or delivery paths (e.g., to protect people from heavy equipment and/or objects transiting the delivery paths).

In various embodiments, one or more of portable electronic monitoring devices 40 emit, reflect, and/or detect light, such as lasers 50. In a specific embodiment, laser 50 is a Pulse Width Modulation (PWM) laser. When one or more of portable electronic monitoring devices 40, such as first monitoring device 42, detect an intruder 22 close to or within protected area 20, the first monitoring device 42 and/or second monitoring device 43 sends a notification 60 to one or more remote devices and/or people.

Referring to FIG. 2, in various embodiments keep out zone system 10 is configured to send one or more different types of notifications 60. As an example, first monitoring device 42 issues an alert, shown as an audio and visual alert 66. As another example, first monitoring device 42 sends a wireless signal, shown as short to medium range wireless signal 64, to an individual 24 in charge of protected area 20 and/or that arranged portable electronic monitoring devices 40 around protected area 20. As another example, first monitoring device 42 sends a wireless signal, shown as cellular signal 68, to a database 90 that stores some and/or all intrusion events within protected area 20. As another example, first monitoring device 42 sends a wireless signal, shown as a medium to long range wireless signal 65, to individual 26 responsible for safety at the worksite.

As another example, first monitoring device 42 sends a wireless signal, shown as Bluetooth signal 62, to tool 82 (e.g., electric tool) associated with protected area 20. In a specific embodiment, tool 82 automatically disables upon receiving notification 60 of an intruder 22 within protected area 20. In various embodiments, electric tool 82 is configured to receive a notification that the intrusion was detected in the protected area (e.g., from device 42), and generate a safety alarm in response to the detection of the intrusion. In one example, tool 82 is configured to disable a functionality in response to the detection of the intrusion (e.g., tool 82 is a power drill and the rotating tip of the drill is disabled in response to receiving the notification).

In various embodiments, keep out zone system 10 includes a wire 51 around protected area 20, the wire 51 emitting a radio frequency. When an individual carrying an electronic personal device (e.g., personal device 80) approaches within a threshold distance of protected area 20, an alarm and/or notification is generated via the personal device detecting the radio signal emitted by wire 51, and as a result personal device 80 emits a warning signal.

In another embodiment, keep out zone system 10 includes pucks arranged around protected area 20. When an individual carrying an electronic personal device approaches within a threshold distance of protected area 20, an alarm and/or notification is generated. If a user walks past a protective device in a direction that passes by the protected area 20 (e.g., the person is detected for a short length of time and/or by a small signal detection), then the system does not generate an alarm and/or notification. In contrast, if the user is walking towards a protective device (e.g., a signal is detected for a predetermined amount of time and/or the signal is getting stronger and/or signals from multiple protective devices are received) then an alarm and/or notification is generated (e.g., the user is notified).

In another embodiment, a capacitive sensor or motion sensor is applied to a safety lock or a lock box. If the lock is messed with and/or approached within a threshold distance, an alarm and/or notification is generated (e.g., a user receives a notification).

Figure 3:
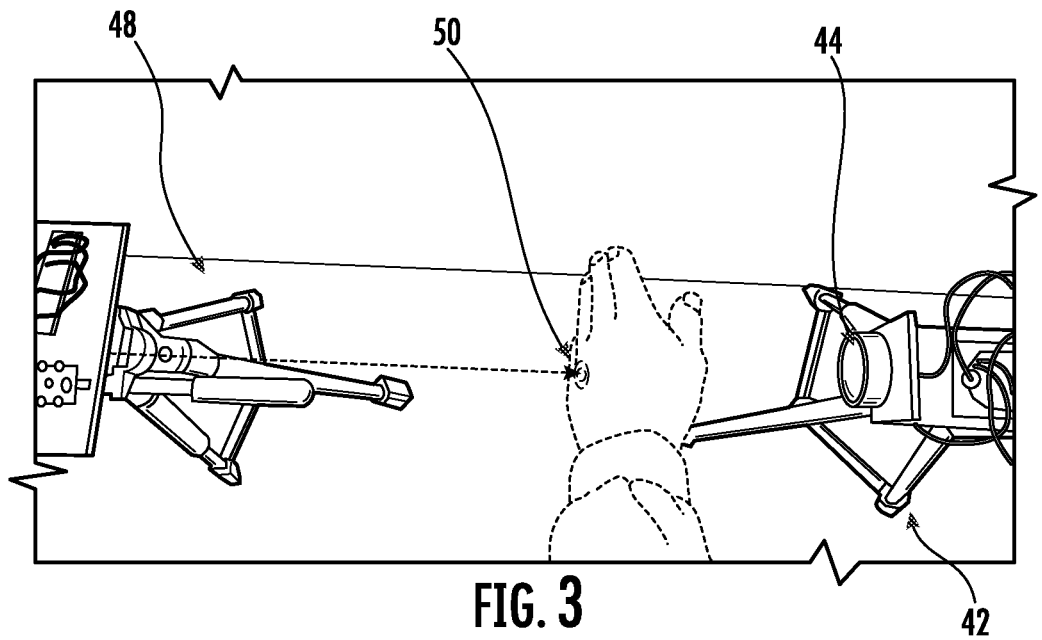
FIG. 3 depicts two monitoring devices of the safety monitoring system of FIG. 1, according to an exemplary embodiment.
Figure 4:
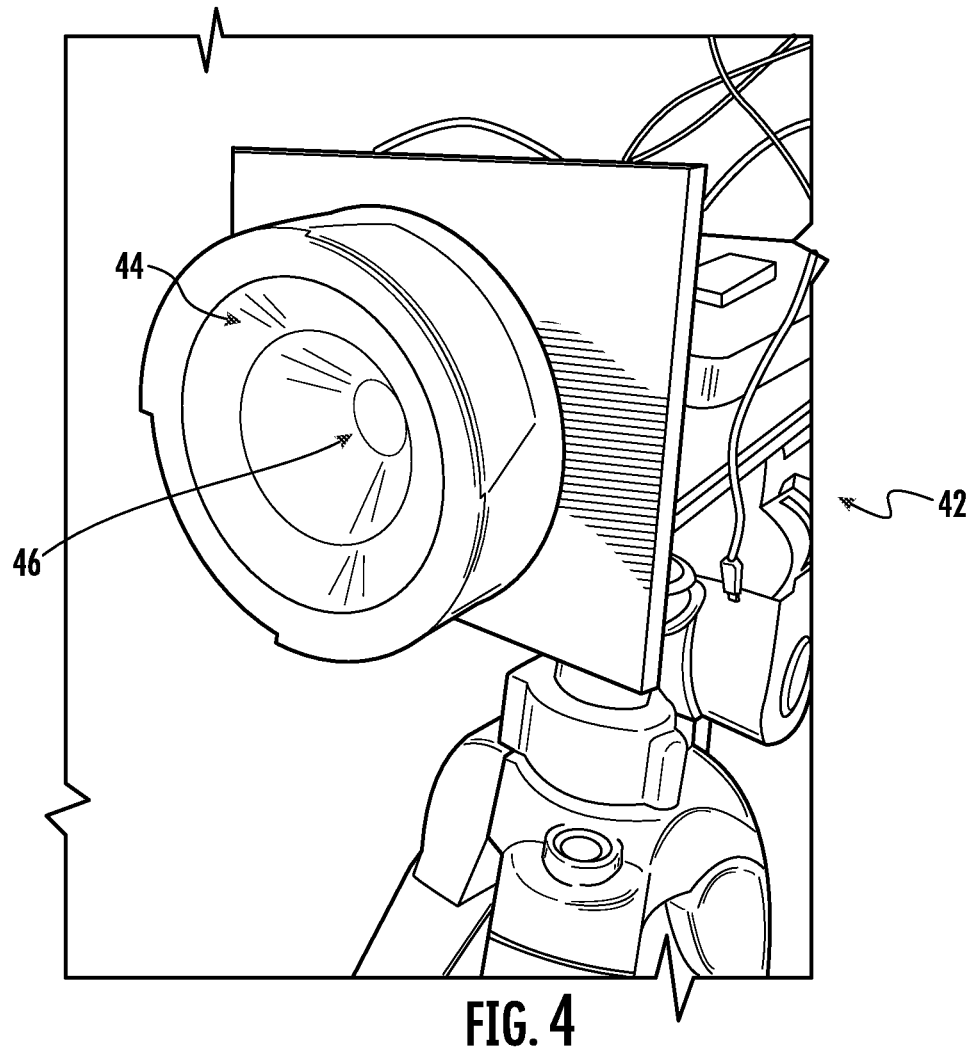
FIG. 4 depicts a monitoring device of the safety monitoring system of FIG. 1, according to an exemplary embodiment.

Referring to FIGS. 3-4, first monitoring device 42 includes a light detector, shown as photodiode 46, and a reflective surface, such as a curved reflector, shown as parabolic reflector 44. Second monitoring device 48 emits laser 50 towards first monitoring device 42, and more specifically laser 50 is emitted towards parabolic reflector 44 and photodiode 46. The person arranging second monitoring device 48 can observe parabolic reflector 44 to help the person determine when the laser 50 is correctly aimed at parabolic reflector 44 and photodiode 46. After the devices are correctly configured and activated, when an object or individual crosses in front of laser 50, the photodiode 46 no longer receives the expected signal and generates an alarm and/or notification.

Figure 5:
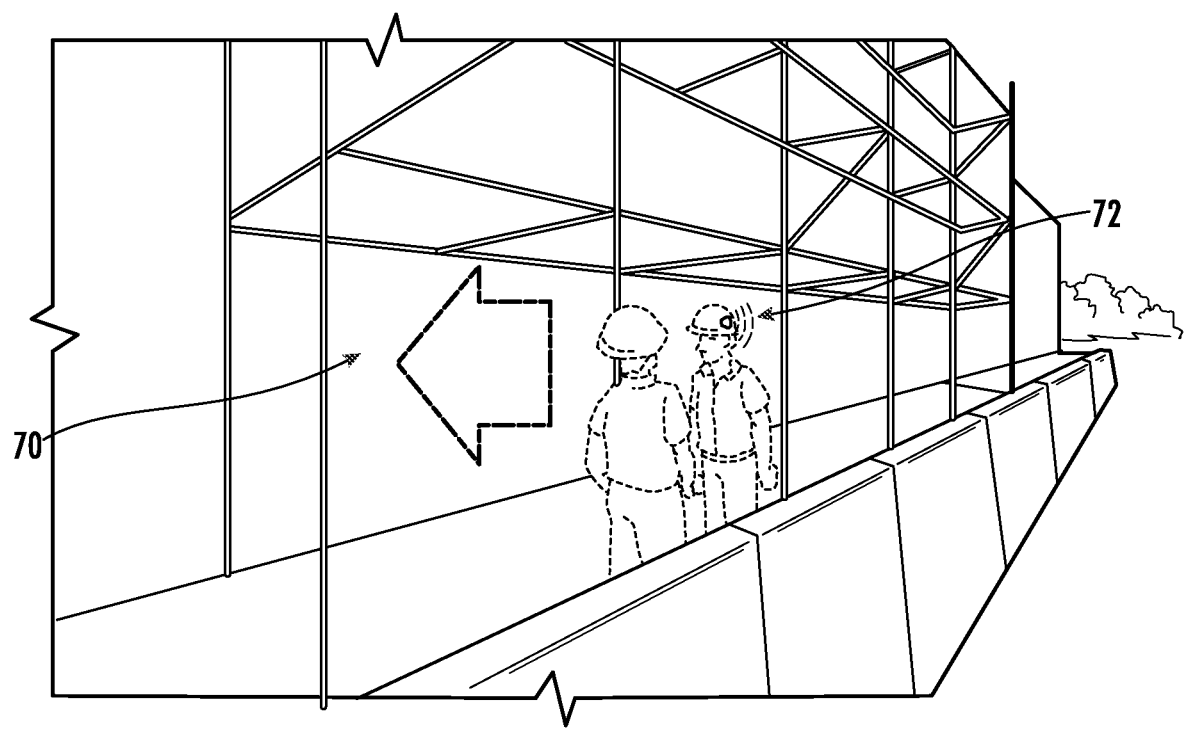
FIG. 5 depicts alarms and notifications being generated by the safety monitoring system of FIG. 1, according to an exemplary embodiment.

Referring to FIGS. 5-7, various warning signals and/or alerts are generated by keep out zone system 10. In various embodiments, keep out zone system 10 generates a visual and/or audio alarm (e.g., a light signal and/or a smoke alarm), a remote indication of a zone violation (e.g., flashing light and/or audio alarm on a remote device, such as a beeper), a communication (e.g., a text message with zone ID and violation, a text message with the ID of the intruder, zone ID, and/or a time stamp), and/or documentation of the violation (e.g., a photograph of the intrusion to the protected area, a video of the intrusion).

In various embodiments, some or all of the following information is communicated upon an intrusion being detected: the name of the intruder, the name of the person monitoring the protected area, whether the protected area is currently active, how long the protected area has been active, if anyone is in the protected area, and/or how many people are in the protected area. In various embodiments, the information described above is communicated at varying points in time: in real time when the intrusion is detected, at set intervals (e.g., hourly), at the end of the day, at the end of the week, and/or only upon request. In various embodiments, if the intrusion persists (e.g., longer than a threshold period of time) the alert and/or notification is escalated (e.g., starting from a personal notification to the intruder and changing into a loud alarm for everyone to hear).

In various embodiments, keep out zone system 10 generates a barrier alarm 70, such as from an element of the barrier (e.g., portable electronic monitoring device 40), and/or keep out zone system 10 generates a personal alarm 72 via one or more personal devices 80 associated with a worker (e.g., the intruder, a person working in protected area 20). In various embodiments the barrier alarm 70 and/or the personal alarm 72 can be a light signal from one or more illuminating devices, a sound (e.g., a horn), an object physically moving, a light on a hard hat, sound on a hard hat or vest, a haptic (e.g., physical movement) of a hard hat or device on the wrist, a signal in a heads-up display, and/or a haptic, sound, or visual effect on a smart phone. Referring to FIGS. 6-7, in various embodiments the personal devices 80 that generates personal alarm 72 include a device on a wrist of the wearer (e.g., a watch or smart device), a smartphone, a hard hat, eye protection, hearing protection, an ID badge, and/or a device clipped to the worker's wrist, belt, or vest.

Figure 8:
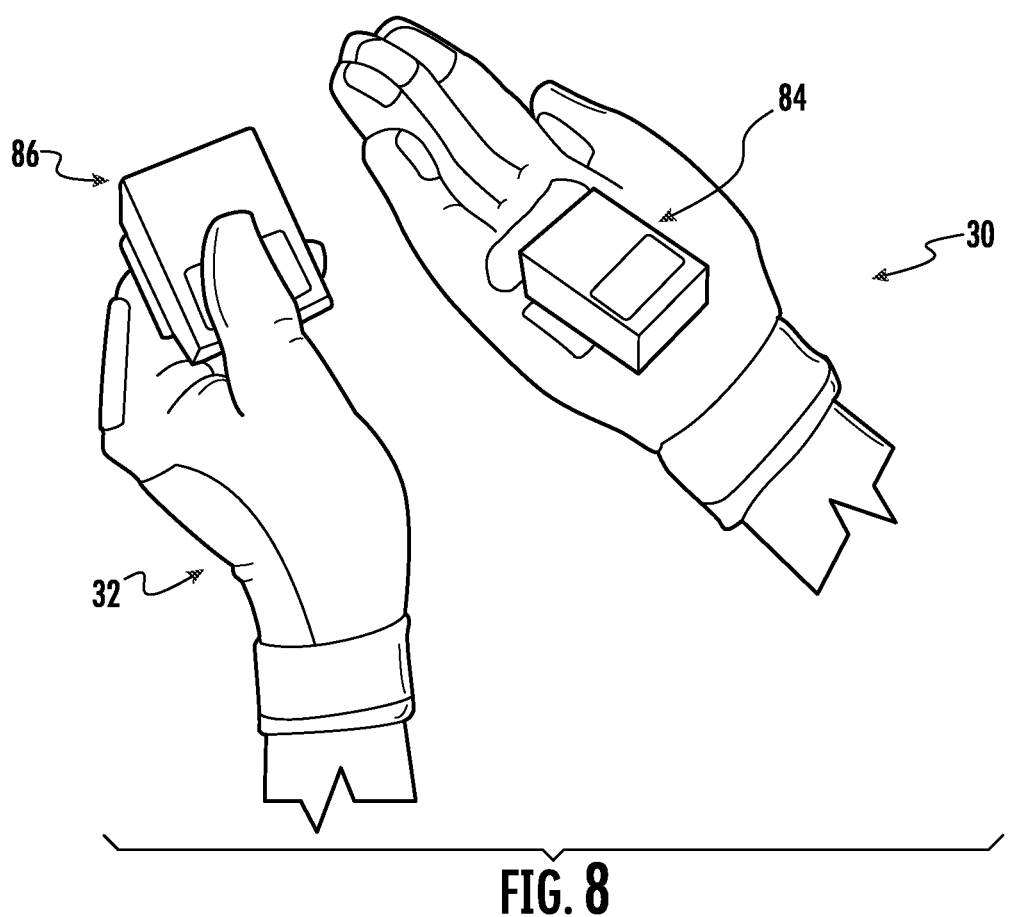
FIG. 8 depicts personal devices that receive input from the safety monitoring system of FIG. 1, according to an exemplary embodiment.
Figure 9:
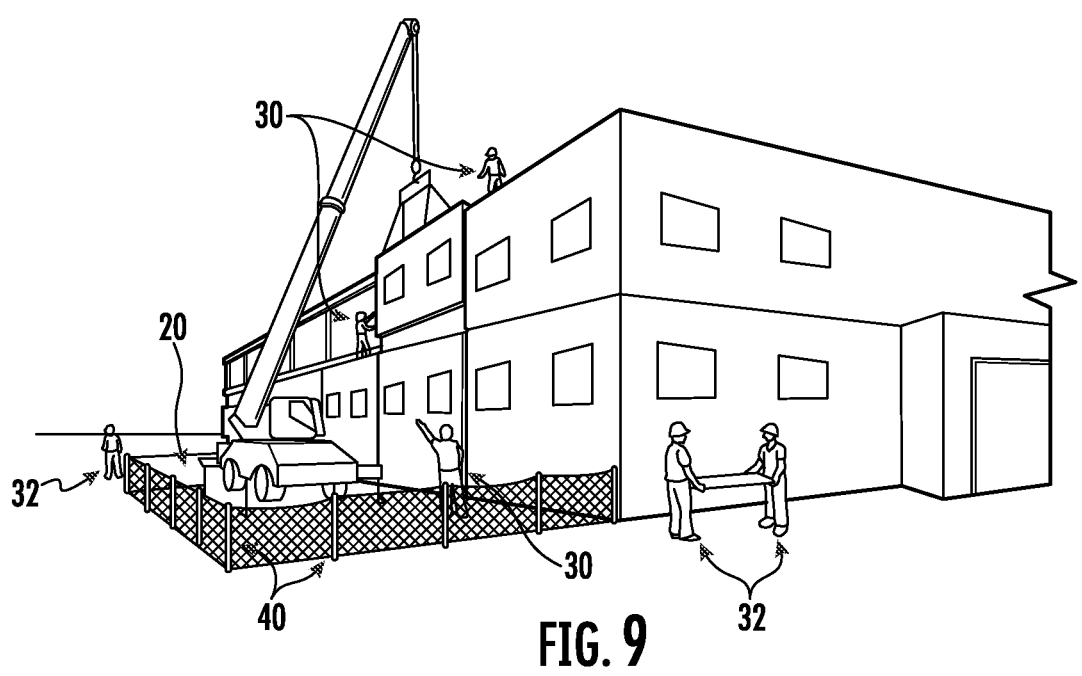
FIG. 9 depicts the safety monitoring system of FIG. 1 using the personal devices of FIG. 8, according to an exemplary embodiment.

Referring to FIGS. 8-9, keep out zone system 10 is configurable to monitor multiple groups of individuals and treat the groups differently. For example, a first group of people may have elevated privileges or access rights compared to a second group of people. In a specific embodiment, a first group of individuals 30 obtain a personal device 84 associated with a first set of access rights, and a second group of individuals 32 obtain a personal device 86 associated a second set of access rights.

In one example, individuals 30 are permitted to enter protected area 20 and individuals 32 are not permitted to enter protected area 20. In various embodiments, if individual 30 enters protected area 20 the keep out zone system 10 is configured to generate a first alarm and/or notification, and if individual 32 enters protected area 20 the keep out zone system 10 is configured to generate a second alarm and/or notification different than the first alarm.

When individual 30 enters protected area 20, an alert is sent to a personal device, such as personal device 84, that individual 30 is within the protected area 20. This notification increases the situational awareness of individual 30 with respect to the dangers of protected area 20 (e.g., a crane moving large objects within protected area 20). In contrast, when individual 32 enters protected area 20, an alarm is triggered and/or an alert is sent to a personal device, such as personal device 86, that individual 32 is within the protected area 20. This alarm and/or notification increases the situational awareness of individual 32 and the individuals 30 working within protected area 20 that there is an issue (e.g., an unauthorized individual 32 is in a dangerous and/or protected area).

Figure 10:
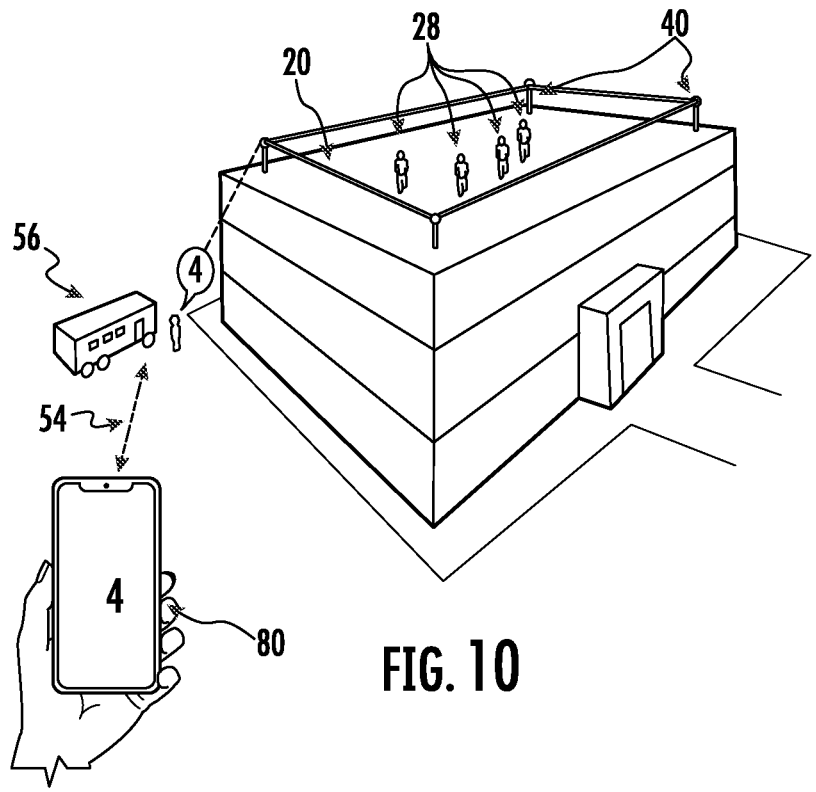
FIG. 10 depicts the safety monitoring system of FIG. 1, according to an exemplary embodiment.
Figure 11:
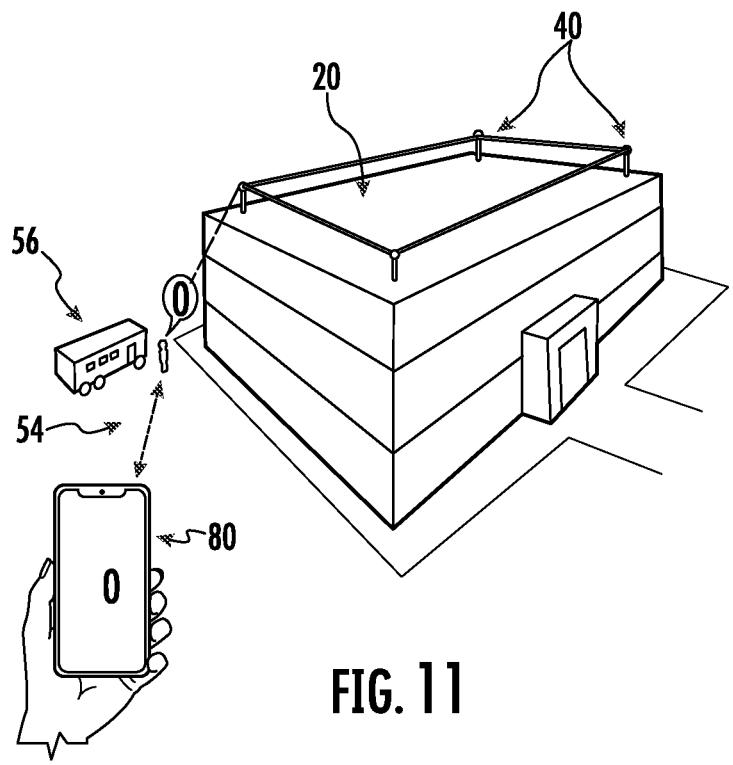
FIG. 11 depicts the safety monitoring system of FIG. 1, according to an exemplary embodiment.

Referring to FIGS. 10-11, various aspects of keep out zone system 10 monitoring protected area 20 are shown. In various embodiments, portable electronic monitoring devices 40 of keep out zone system 10 monitor the number and/or location of individuals 28 within protected area 20. At least some of that information is communicated from portable electronic monitoring devices 40, such as to monitoring station 56. In various embodiments, monitoring station 56 sends a communication, shown as electronic signal 54, to a personal device 80. As one example, monitoring station 56 sends electronic signal 54 to a personal device 80 indicating a number of people within protected area 20.

Figure 12:
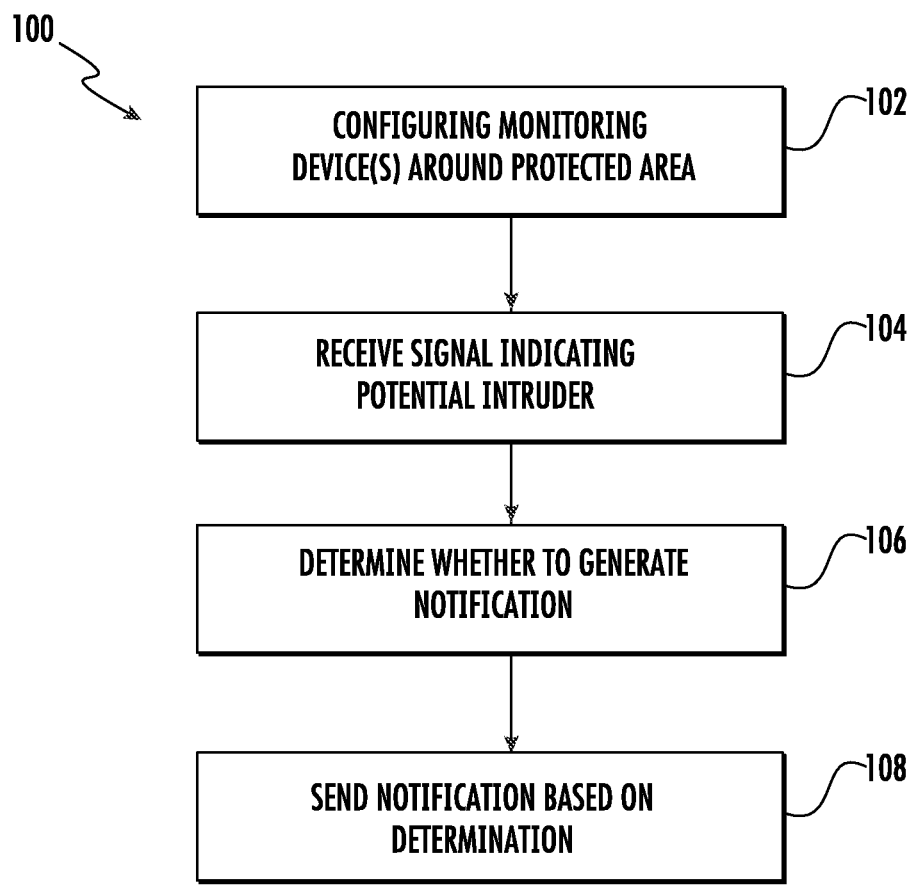
FIG. 12 depicts an exemplary method of using the safety monitoring system of FIG. 1, according to an exemplary embodiment.

Referring to FIG. 12, various aspects of one or more of the exemplary methods of utilizing keep out zone system 10 are described herein. In this exemplary process 100, one or more portable electronic monitoring devices 40 are configured around a protected area 20 (step 102). A signal is generated that indicates a potential intruder within or near the protected area 20 (step 104). For example, a monitoring unit within a portable electronic monitoring device 40 detects an interrupted laser signal, and sends a signal to an analysis unit within the portable electronic monitoring device 40. Subsequently, it is determined whether to generate a notification and/or alarm (step 106). For example, if the signal interruption was too brief, portable electronic monitoring device 40 may determine that the signal interruption is not consistent with an intruder. Optionally an alarm and/or notification is sent in response to determining the signal interruption indicates a potential intruder to protected area 20 (step 108).

Referring to FIGS. 13-31, various aspects of keep out zone system 110 are shown. In particular, in various embodiments keep out zone system 110 includes monitoring devices that monitor a length and/or tension of safety equipment (e.g., caution tape, flag line, safety chain). Keep out zone system 110 is substantially the same as keep out zone system 10 except for the differences discussed herein.

Figure 13:
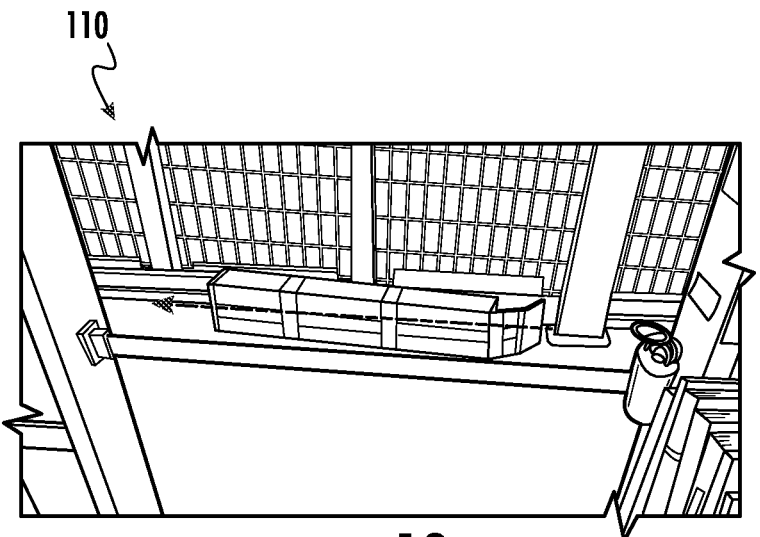
Figure 14:
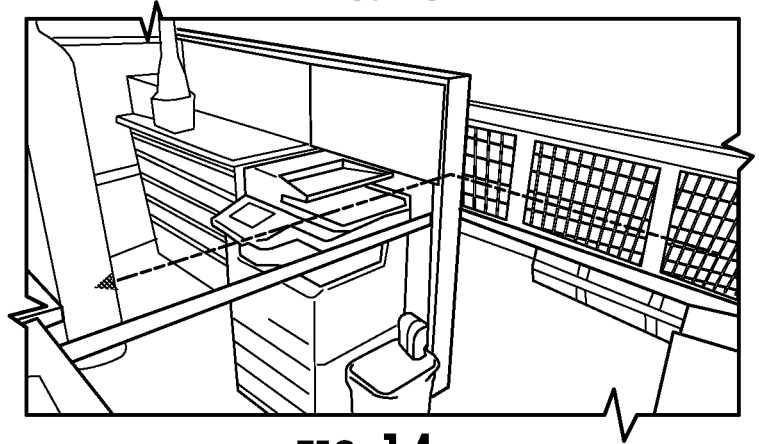
Figure 15:
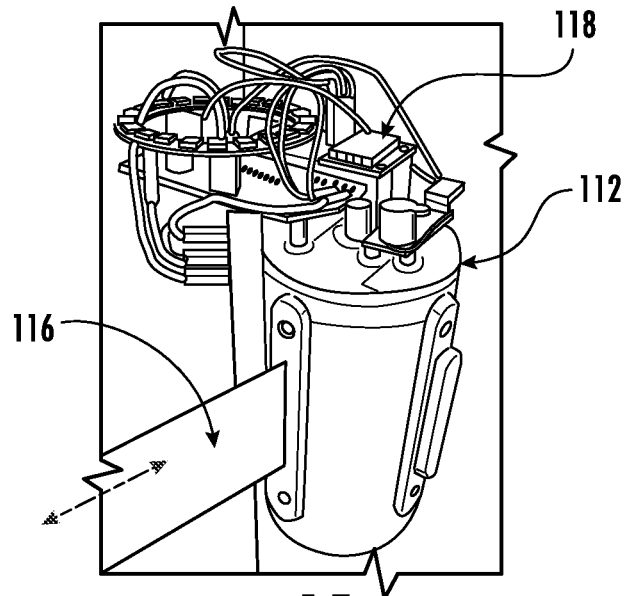

Keep out zone system 110 includes an elongate structure, shown as caution tape in FIGS. 13-15, that extend between one or more coupling structures. In various alternative embodiments, the elongate structure is a flag line, or a chain, such as a safety chain.

Keep out zone system 110 includes one or more sensors. The sensors are configured to identify changes in conditions, such as a change in length of the caution tape, a change in tension of the caution tape, a change in orientation (e.g., if the sensor is knocked over) via an accelerometer 118 and/or gyroscope, and/or a change in location via touch sensor technology. In various embodiments, an intrusion to the protected area is detected as a result of a device including an accelerometer 118 receiving a signal from the accelerometer 118 (e.g., the signal indicating that the device was dropped or knocked over).

It is contemplated herein that one and/or all aspects and/or components in keep out zone system 110 may be used with keep out zone system 10 (e.g., the elongate structure, such as caution tape, the accelerometer). For example, the elongate structure may be used with keep out zone system 10, including keep out zone system 10 including a device that monitors a length and/or a tension of the elongate structure.

For example, keep out zone system 110 includes first device 112, elongate structure 116 extending from first device 112. First device 112 includes a monitoring device 114 that monitors a length and/or tension of elongate structure 116. First device 112 includes an accelerometer 118 configured to detect movement of the first device 112, such as if first device 112 was dropped or fell over.

Referring to FIGS. 13-15, the caution tape can be extended across openings, such as doorways, to control access to the area inside the opening. In use, the caution tape can be extended around (wrapper partially around) other objects, such as a pole, to make more complex zones.

In various embodiments the coupling structure includes a reel that the caution tape is wound around. In use, the caution tape is extended and retracted from the coupling structure. In various embodiments, the coupling structure includes an notification generating element, shown as an audible alarm generator and/or a light generator in FIGS. 13-15. When one or more of the sensors in the coupling structure detects a possible intruder and/or issue, the notification generating element generates an alarm. In various embodiments the caution tape can be removed from the coupling structure and another elongate element can be inserted into the coupling structure and used.

Referring to FIGS. 16-18, in various embodiments the coupling structure includes a user interface. Users can interact with the interface to perform various functions, such as setting a new length of the caution tape, arming the sensors and alarms, and/or disarming the sensors and alarms. Referring to FIG. 16, the elongate structure (e.g., caution tape) extends from an anchor point (left side) to the device on the right side.

Figure 19:
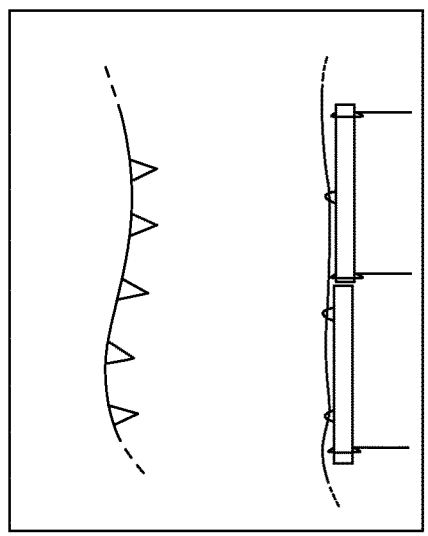
Figure 20:
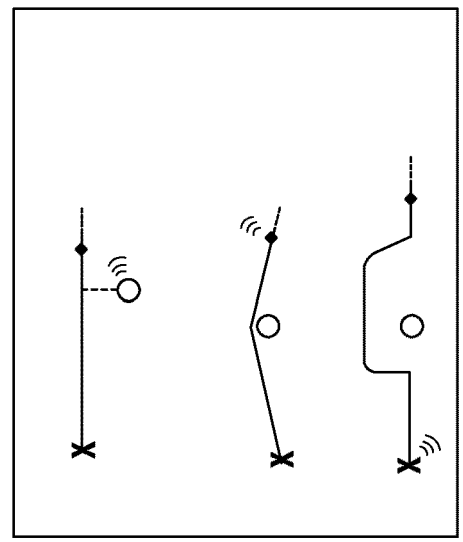
Figure 21:
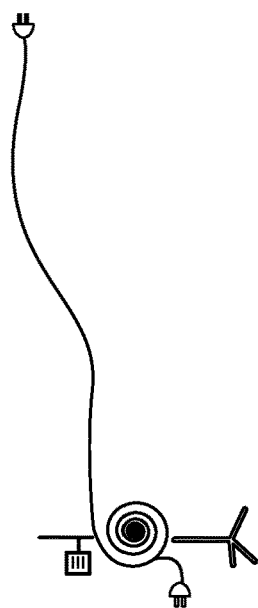
Figure 22:
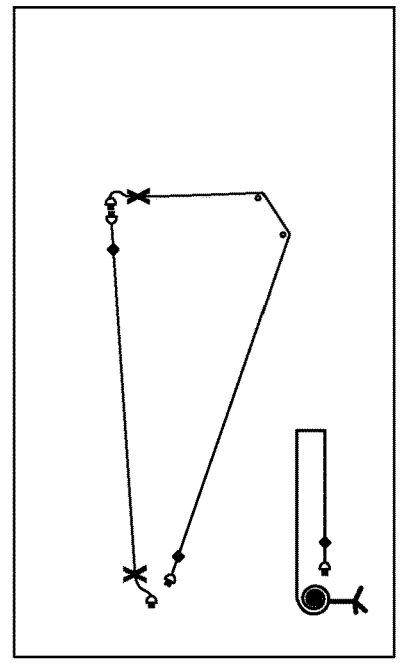
Figure 23:
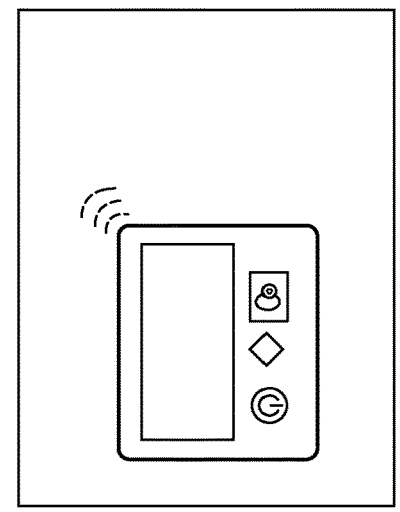

Referring to FIGS. 19-23, the user interface of the coupling structure is configured to receive commands to adjust a length of the caution tape, and to pair the user interface with an electronic device (e.g., a personal electronic device, such as a cell phone and/or alarm, associated with the owner of the area being protected). In various embodiments the elongate structure, shown as a radio-signal transmitting wire, extends in two distinct directions from the coupling structure, such as two opposing directions. In various embodiments, the elongate structure includes a power receiving element, shown as a plug, at either end of the elongate structure. In various embodiments an elongate structure extending from a first coupling structure can be daisy-chained to an elongate structure extending from a second coupling structure. Referring to FIG. 19, in various embodiments the monitoring device includes a plug, a wire spool with retractor, and a control box (e.g., user interface). Referring to FIG. 20, in various embodiments the wire can be turned into a flag line by attaching flags (upper figure in FIG. 20) and/or attached to structures, such as 2×4s (lower figure in FIG. 20). Referring to FIG. 23, the alarm may be tripped as a person approaches a radio-signal emitting wire (upper image), if tension in the wire/cape changes (middle image), and/or if the length of the wire/tape is changed (lower image).

A sensor monitors the elongate structure(s) and triggers an alarm if one or more conditions are satisfied. A first condition that may trigger an alarm is if an object approaches within a predetermined distance from the elongate structure. A second condition that may trigger an alarm is if the elongate structure is pulled (e.g., made more taut), thereby tripping the tension-monitoring sensor. A third condition that may trigger an alarm is the elongate structure being lengthened.

Referring to FIG. 24, in various embodiments a single sensor monitors two or more aspects of the elongate structure. For example, a single sensor monitors both the tension of the elongate structure (e.g., via a force exerted by the tape on the wheel in the middle of the image on the right) and/or the length of the elongate structure (e.g., via whether the middle wheel turns).

Figure 25:
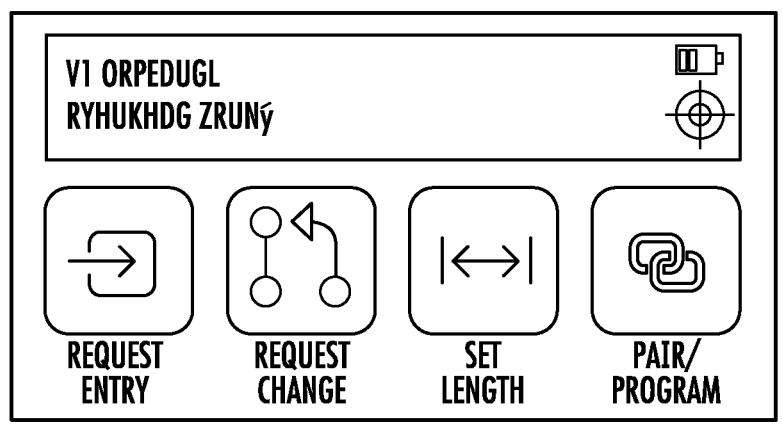

Referring to FIG. 25, in various embodiments a user interface is configured to communicate various data and to receive a variety of commands from users. For example, the user interface identifies the owner of the zone being protected, indicates the power supply and/or level (e.g., battery level), identifies whether the control box is ready to pair with an electronic device, includes an interface button to pair the control box with an electronic device (e.g., a personal cell phone), includes an interface button to set a length of the elongate structure, includes an interface button to change the configuration (e.g., length) of the elongate structure without triggering an alarm, and includes an interface button to request permission to enter the protected area without triggering an alarm.

Figure 26:
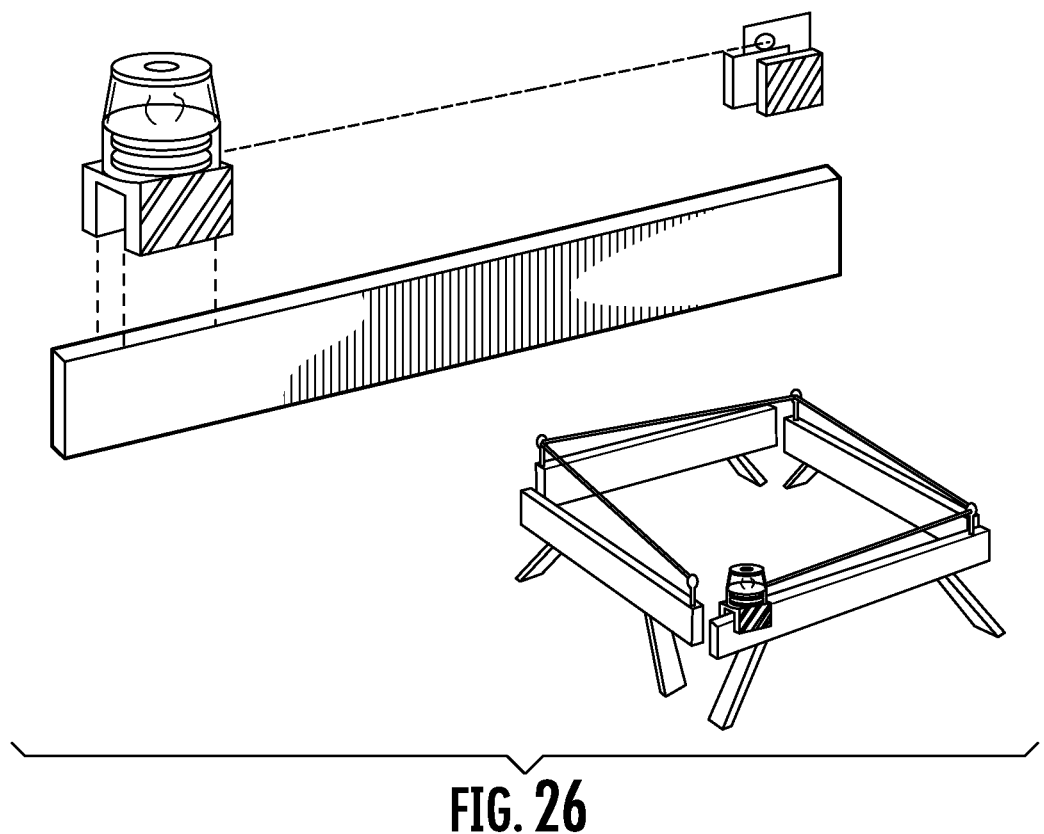

Referring to FIG. 26, in various embodiments the elongate structure is a wire that extends around the protected area and plugs into the coupling structure from which the elongate structure extends (e.g., into an outlet on the coupling structure).

Figure 27:
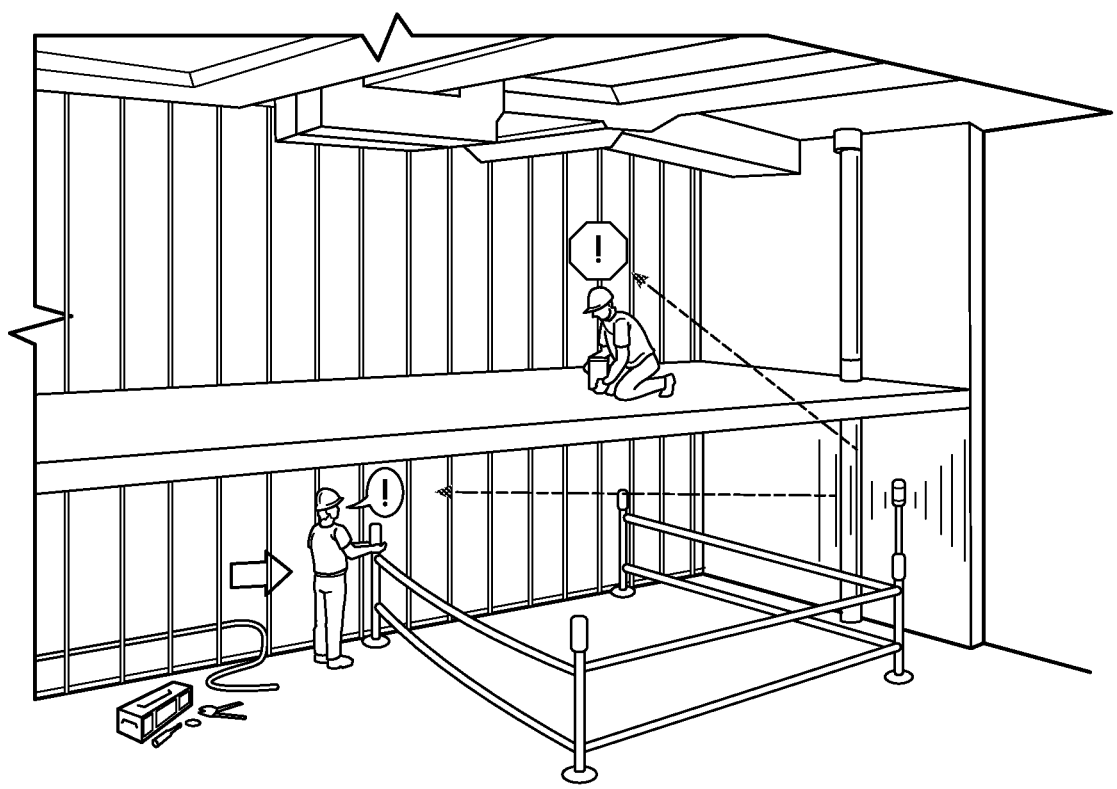

Referring to FIG. 27, in various embodiments the intruder (the person on the left) causing the intrusion receives a visual and/or an audible alert when the intrusion is detected. The worker that set up the zone (the person above) has a receiver device that receives a notification that something changed.

Referring to FIG. 28, the keep out zone system 110 is configured to permit one or more methods for users to access the protected area without triggering an alarm. For example, the user may enter a code, such as a 4-digit code (image on the left), to enter the protected area without triggering the arm (e.g., the keep out zone system 110 is temporarily disabled, such as for ten seconds, while the user transits the elongate structure to enter the protected area). As another example, the user have an electronic device (e.g., passive or powered) that is detected by the keep out zone system 110 (images in the center and on the right). In response to detecting the electronic device, the keep out zone system 110 permits the user to enter the protected area (e.g., by temporarily disabling the sensors and/or alarms).

Figure 29:
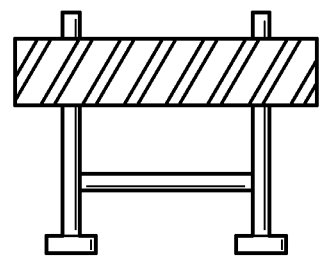
Figure 30:
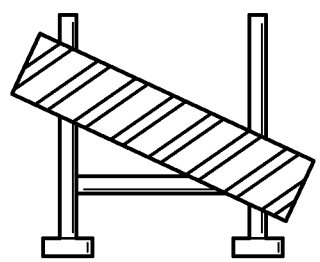
Figure 31:
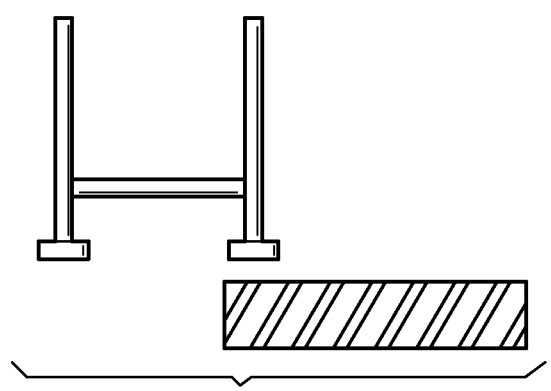

Referring to FIGS. 29-31, various aspects of barriers are shown. Referring to FIG. 29, a properly setup barrier can be sufficient at protecting against hazards, particularly compared to barriers that are knocked down (FIG. 30-31) or broken.

Referring to FIGS. 32-37, various aspects of keep out zone system 210 are shown. In various embodiments, keep out zone system 210 includes multiple modes to improve situational awareness of people near and/or inside the protected area. Keep out zone system 210 is substantially the same as keep out zone system 10 or keep out zone system 110 except for the differences discussed herein.

In many situations, the hazard zone is below the workers performing a task (e.g., FIG. 32). The hazard zone is used to define the possible fall zone where there is the highest risk of being struck by falling objects.

Figure 32:
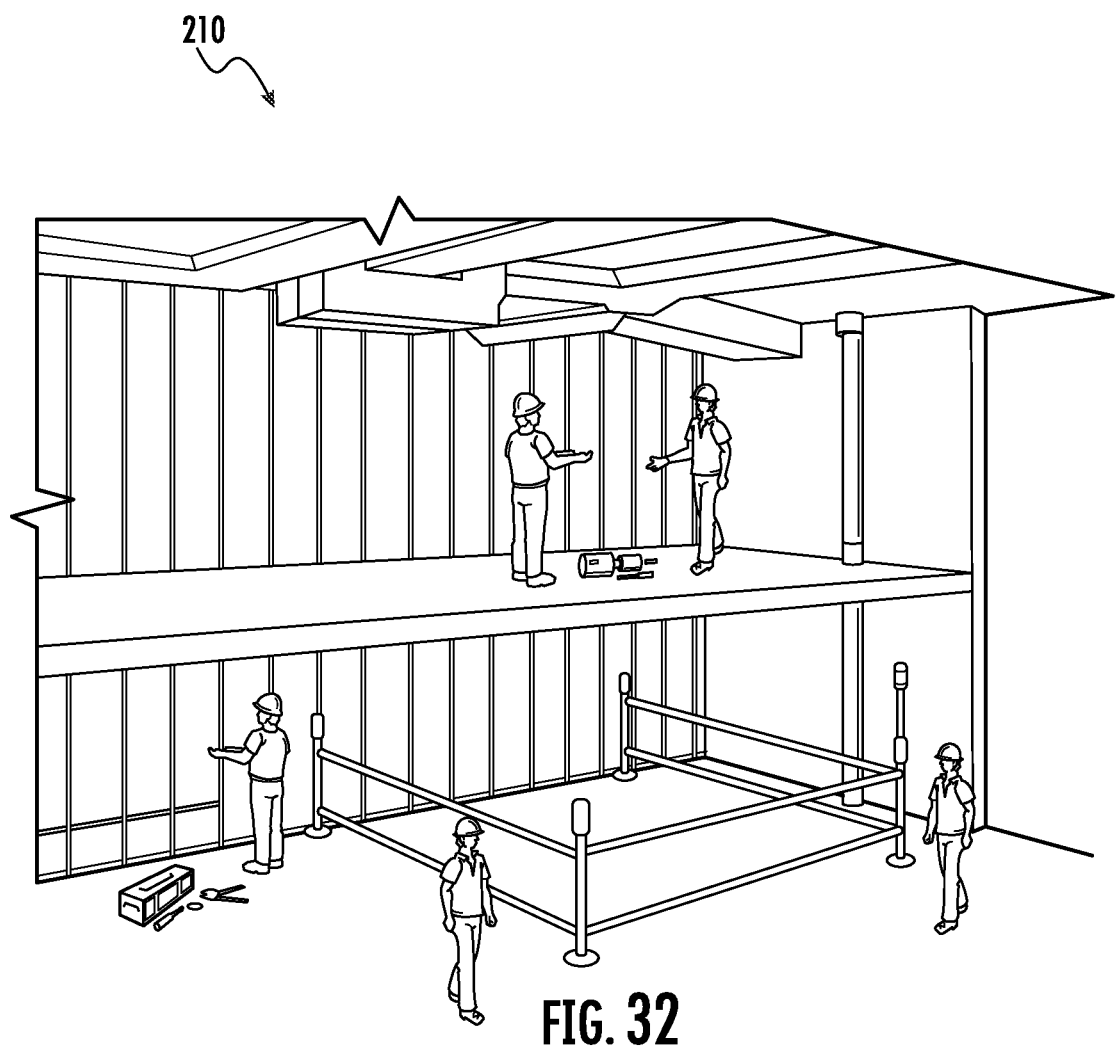
FIGS. 32-37 depict various aspects of the safety monitoring system of FIG. 1, according to an exemplary embodiment.
Figure 33:
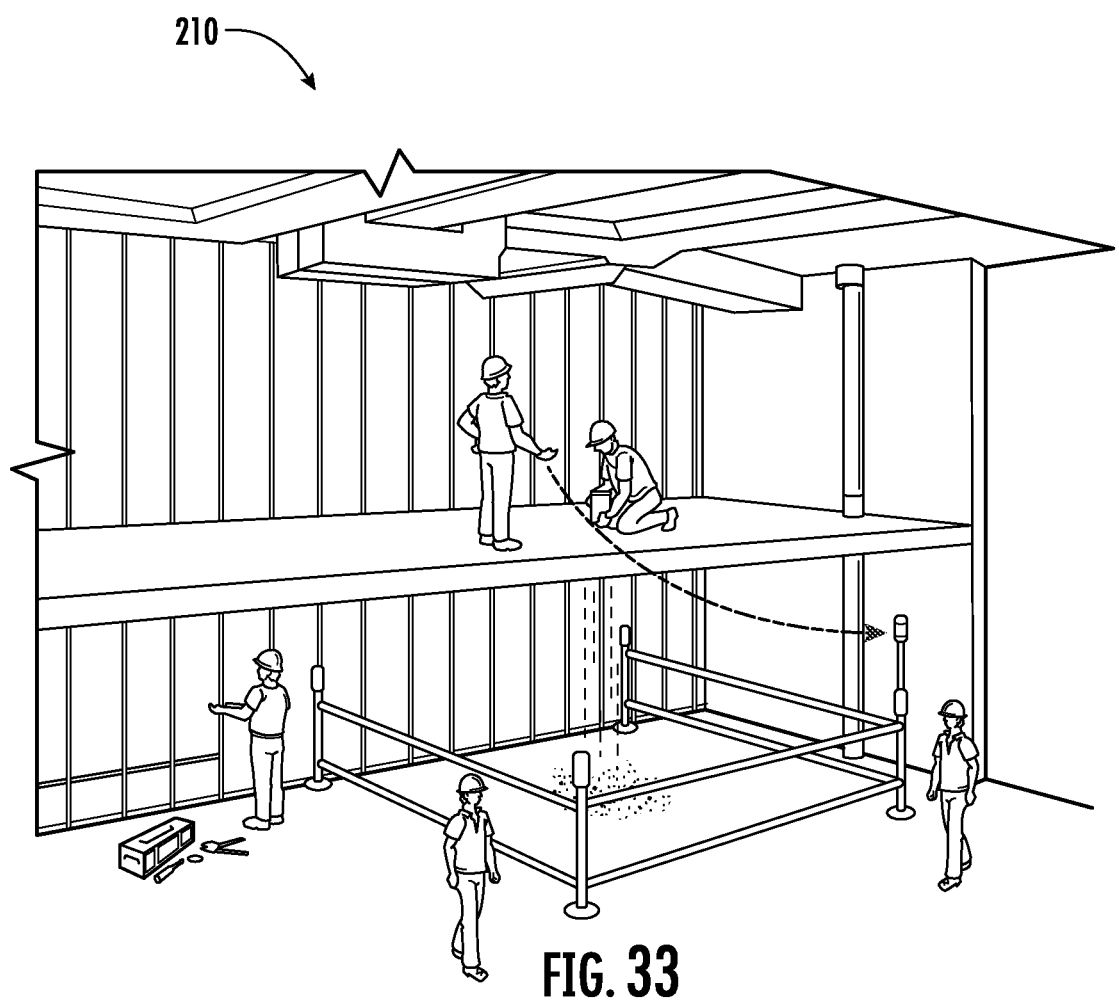
Figure 34:
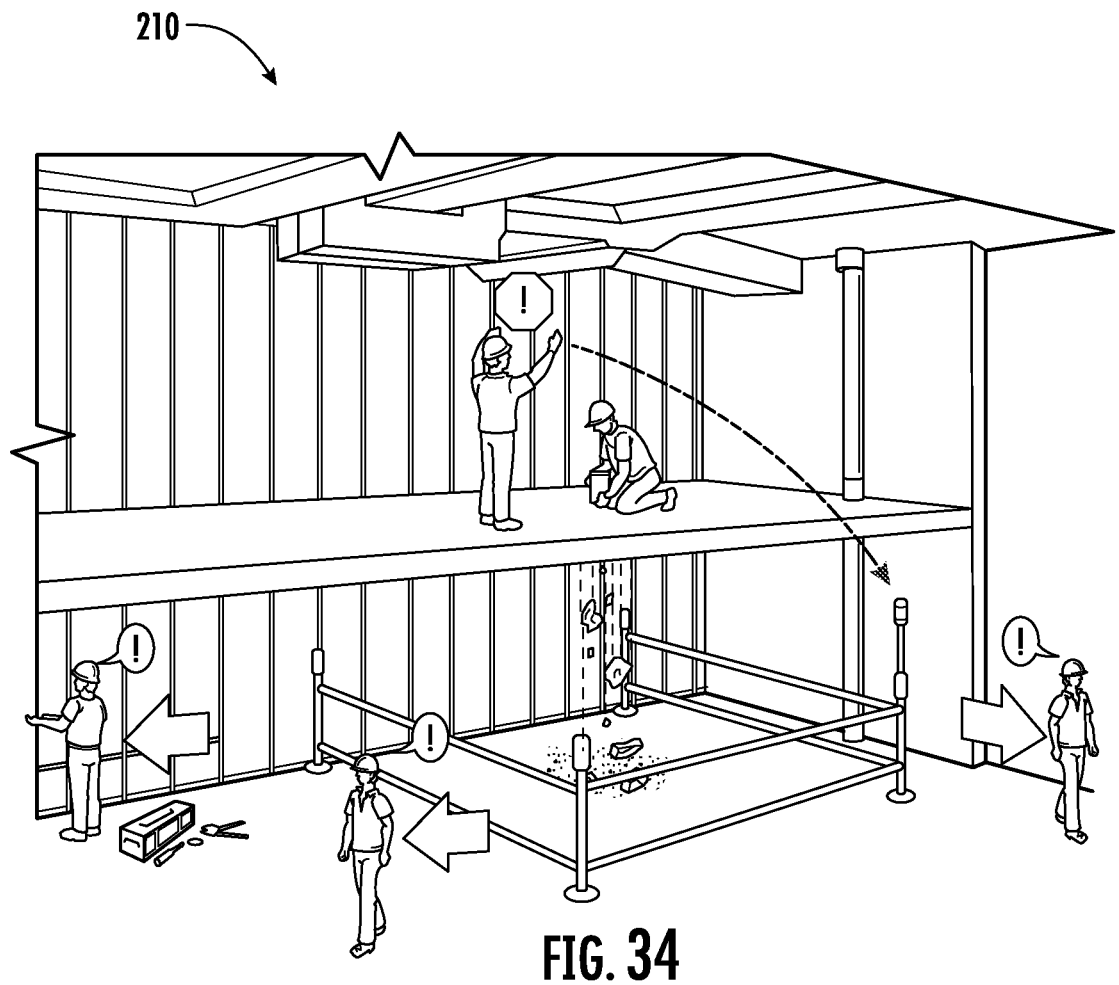
Figure 35:
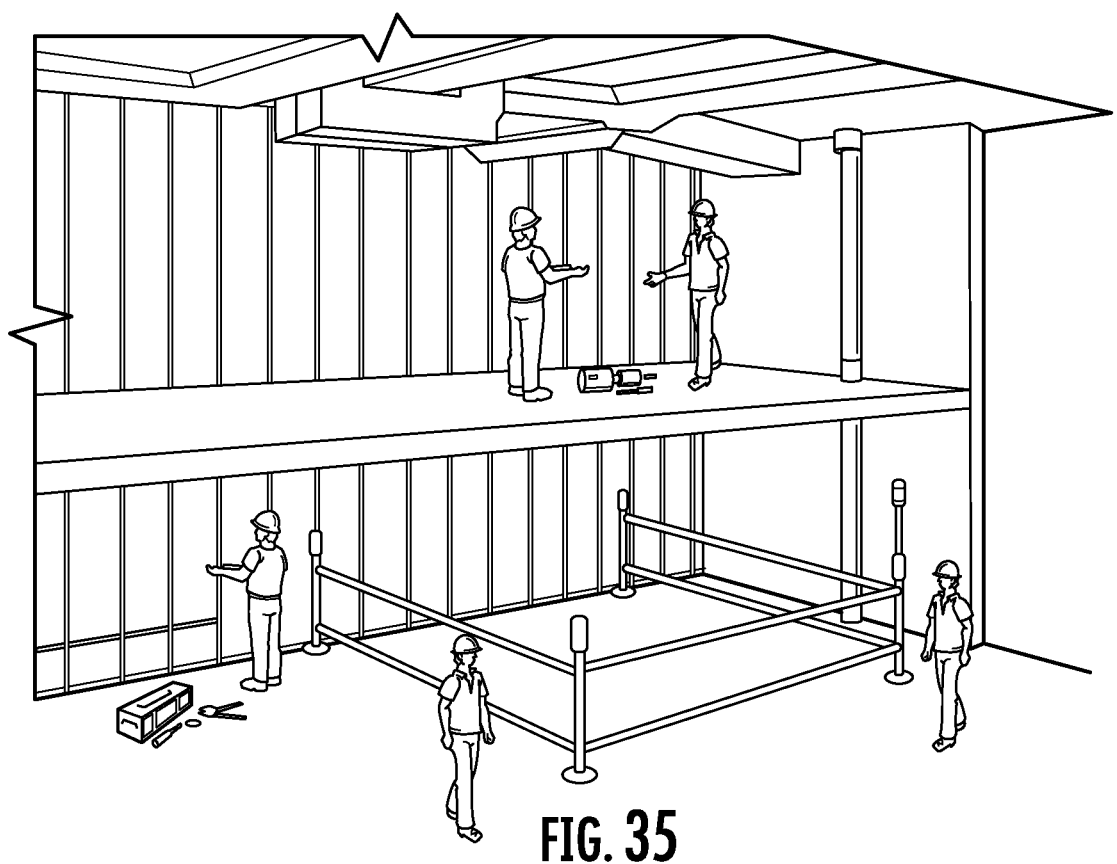
Figure 36:
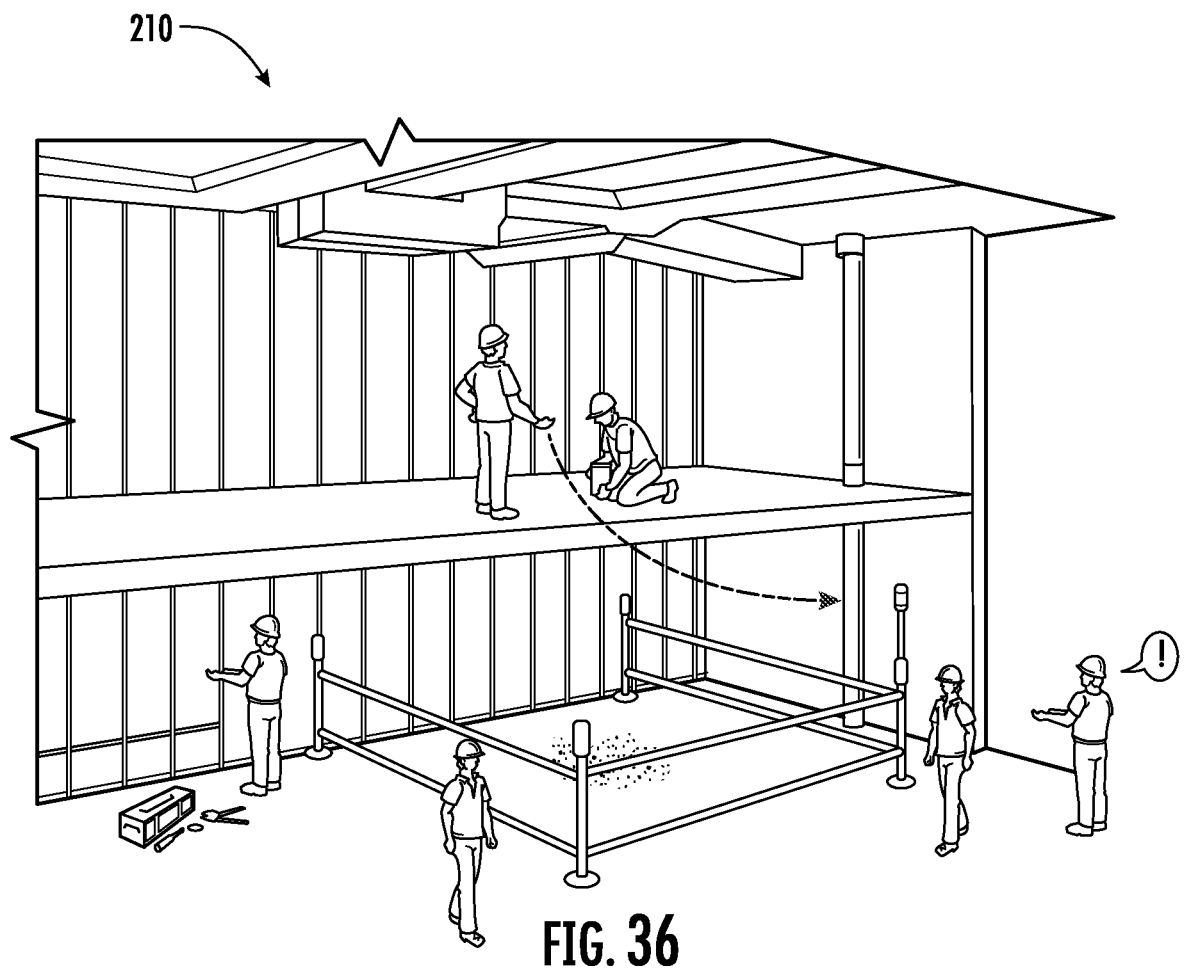
Figure 37:
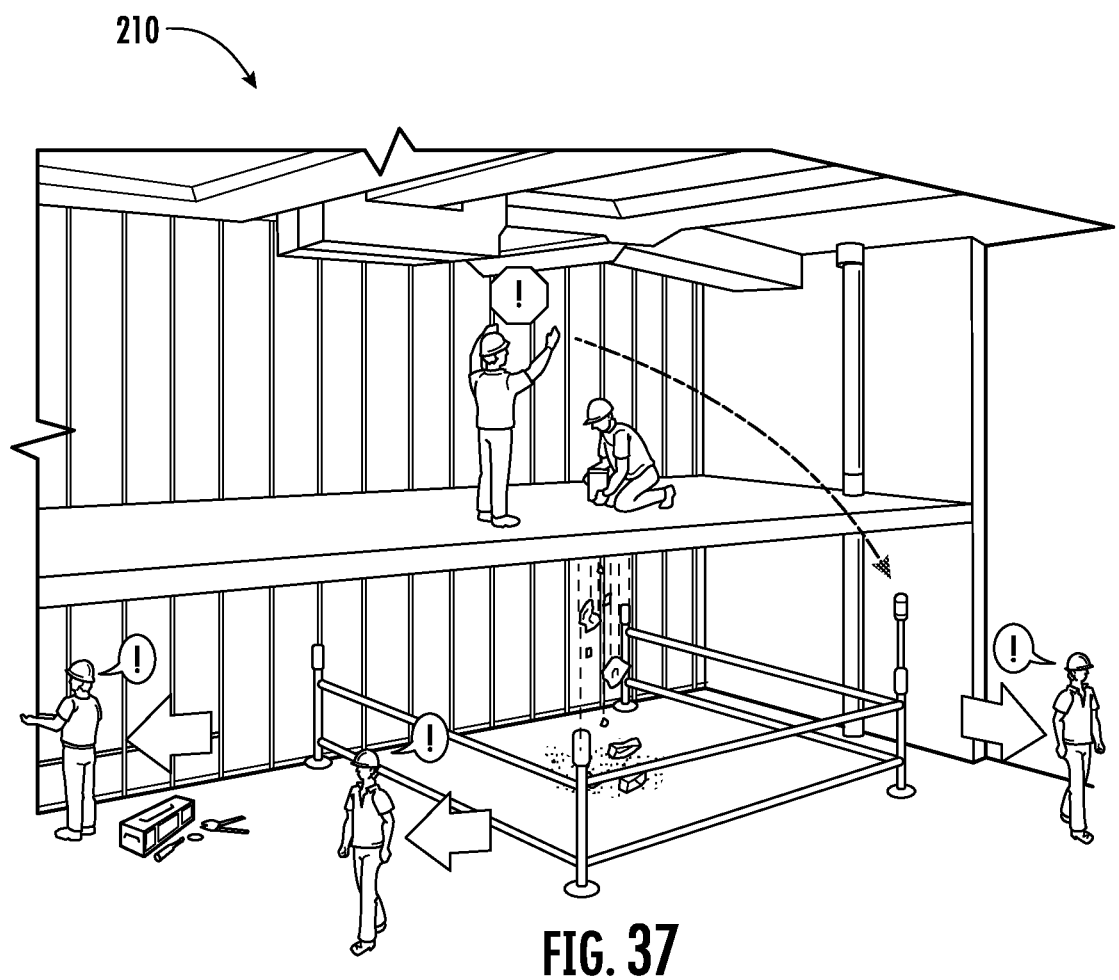

Referring to FIGS. 32 and/or 35, in a first mode ("Static" or "Dormant") no alerts and/or signals are transmitted. Referring to FIGS. 33 and/or 36, in a second mode ("Active"), such as just before work starts, a mildly alarming signal is generated (e.g., a light slowly pulsing like a heartbeat). Referring to FIGS. 34 and/or 37, in a third mode ("Alarm"), such as just before a dangerous situation begins (e.g., just before heavy objects start falling), a very alarming signal is generated (e.g., fast flashing lights and/or a loud signal). Using a remote controller, workers performing the work can remotely adjust the mode of the keep out zone system 210 consistent with the level of activity being performed by the workers. The modification of modes improves the situational awareness of the workers near the protected area by alerting them to the developing dangers within the protected area.

In a specific embodiment, the keep out zone system 210 includes one or more devices that monitor a protected area. The devices are configured to receive commands from a remote user and to send an alarm to the user in response to a trigger. The devices begin operations in a first mode. In response to receiving a first command, such as from the remote user, the devices begin operating in a second mode. The second mode includes an increased level of notifications compared to the first mode, such as by increasing a state of an audio alarm (e.g., initiating an audio sound) and/or increasing a state of a visual alarm (e.g., initiating a visual alarm such as a pulsing light, increasing the brightness and/or pulsing frequency and/or rotational speed of a light). For example, the remote user may trigger the second mode when the remote user is about to start performing work that may be dangerous to people in the protected area.

In response to receiving a second command, such as from the remote user, the devices begin operating in a third mode. The third mode includes an increased level of notifications compared to the second mode, such as by increasing a state of an audio alarm and/or increasing a state of a visual alarm. For example, the remote user may trigger the second mode when the remote user is about to start performing work that may imminently cause danger in the protected area (e.g., actual falling debris).

In various embodiments, the remote user receives a notification when a sensor determines that a person may have entered the protected area. This notification can indicate to the remote user to stop performing their work until the trespasser is removed from the protected area.

Referring to FIGS. 38-45, various aspects of a safety monitoring system, shown as keep out zone system 310, are shown. Keep out zone system 310 is substantially the same as keep out zone system 10, keep out zone system 110, or keep out zone system 210 except for the differences discussed herein. Keep out zone system 310 includes a monitoring device, shown as protected device 320, and a personal device 330.

In an exemplary embodiment, keep out zone system 310 is configured to increase the safety of a user when performing work, such as electrical work. In such an embodiment, keep out zone system 310 includes a device, shown as protected device 320. In this specific example, the user performs work on an electrical circuit that includes a step such as disabling the desired electrical circuit(s), such as at an electrical fuse box. Protected device 320 is configured to lock the electrical fuse box and/or alert the user if the electrical fuse box is accessed. In use, the user places the protected device 320 to lock the electrical fuse box and generate an alert if the electrical fuse box is accessed. The user then leaves the electrical fuse box to perform the desired work. If a second person approaches the electrical fuse box and/or tries to access the electrical fuse box, the protected device 320 generates one or more alerts (FIG. 39). The protected device 320 generates the one or more alerts based on data received from one or more data collection devices (e.g., capacitive sensor, accelerometer) that provide an indication of proximity of a person to the fuse box and/or of the attempted access to the fuse box.

In various embodiments, the protected device 320 issues an alert (e.g., haptic, visual, auditory) to alert the second person approaching the protected device 320 that there is a safety issue. In various embodiments, the protected device 320 transmits a message (e.g., wirelessly, such as via radio) to the personal device 330, and the personal device 330 issues an alert (e.g., haptic, visual, auditory) to the user, thereby enabling the user to stop touching the electrical circuitry. In various embodiments, the protected device 320 issues an alert locally and the personal device 330 also issues an alert.

Figure 42:
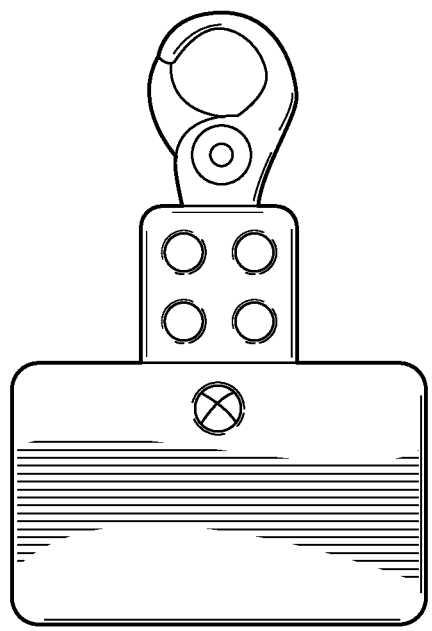
Figure 43:
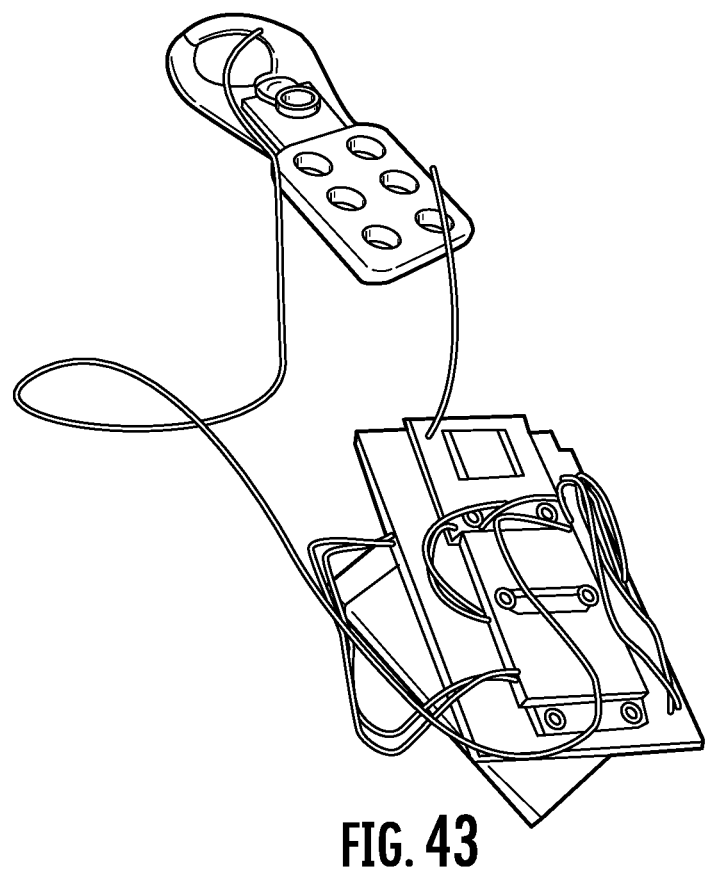

Referring to FIGS. 42-43, in various embodiments the protected device 320 includes a battery, an accelerometer, a capacitive sensor, and/or an RF module. In various embodiments, the RF module continuously sends a keepalive signal to a receiver module, thereby providing assurances to the remote user that the protected device 320 is still monitoring for approaching users. In various embodiments, the lock itself has an active use status light when recently in the range of a receiver module. This is a further indication to individuals who might cut the lock to leave it alone. In various embodiments, the accelerometer and capacitive sensor can be used as inputs into a basic embedded, offline machine learning model (trained in development on relevant field scenarios) to reduce nuisance alarms. In various embodiments, when a triggering event occurs an alert signal is sent to the receiver. In various embodiments, an alert can also be generated by the lock itself (haptic, visual, or auditory), signaling to the individual handling the lock to leave it alone.

Figure 44:
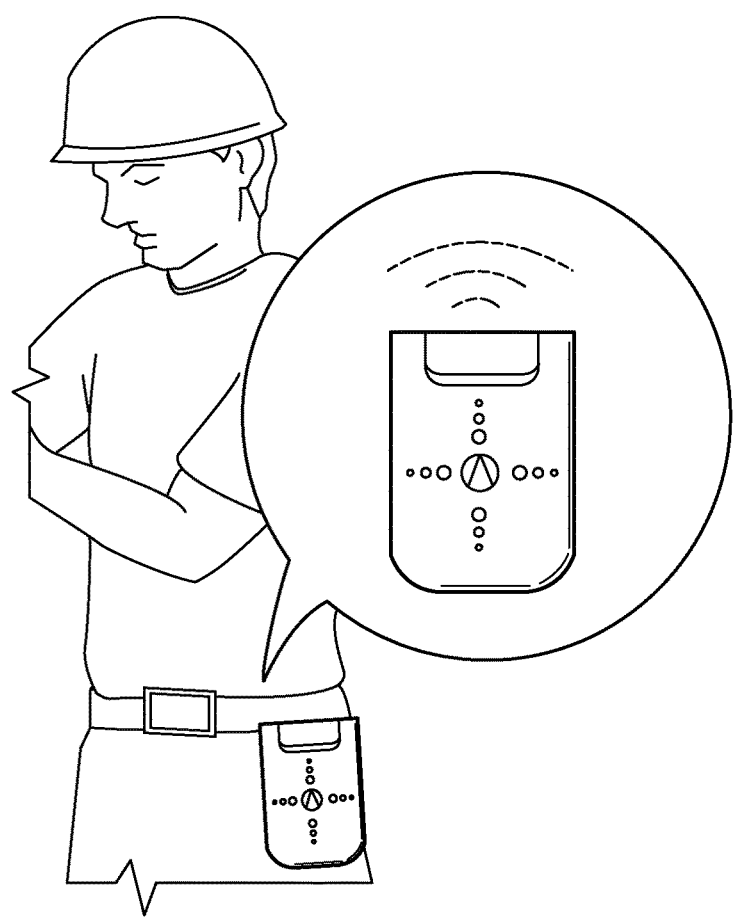
Figure 45:
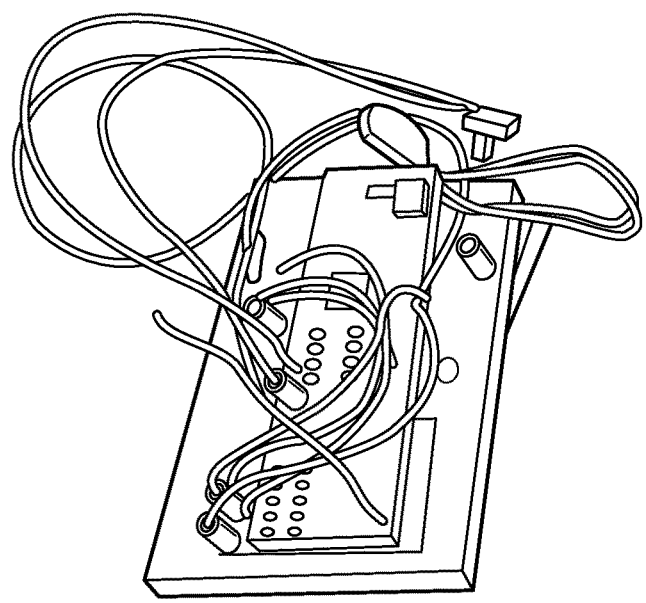
Figure 46:
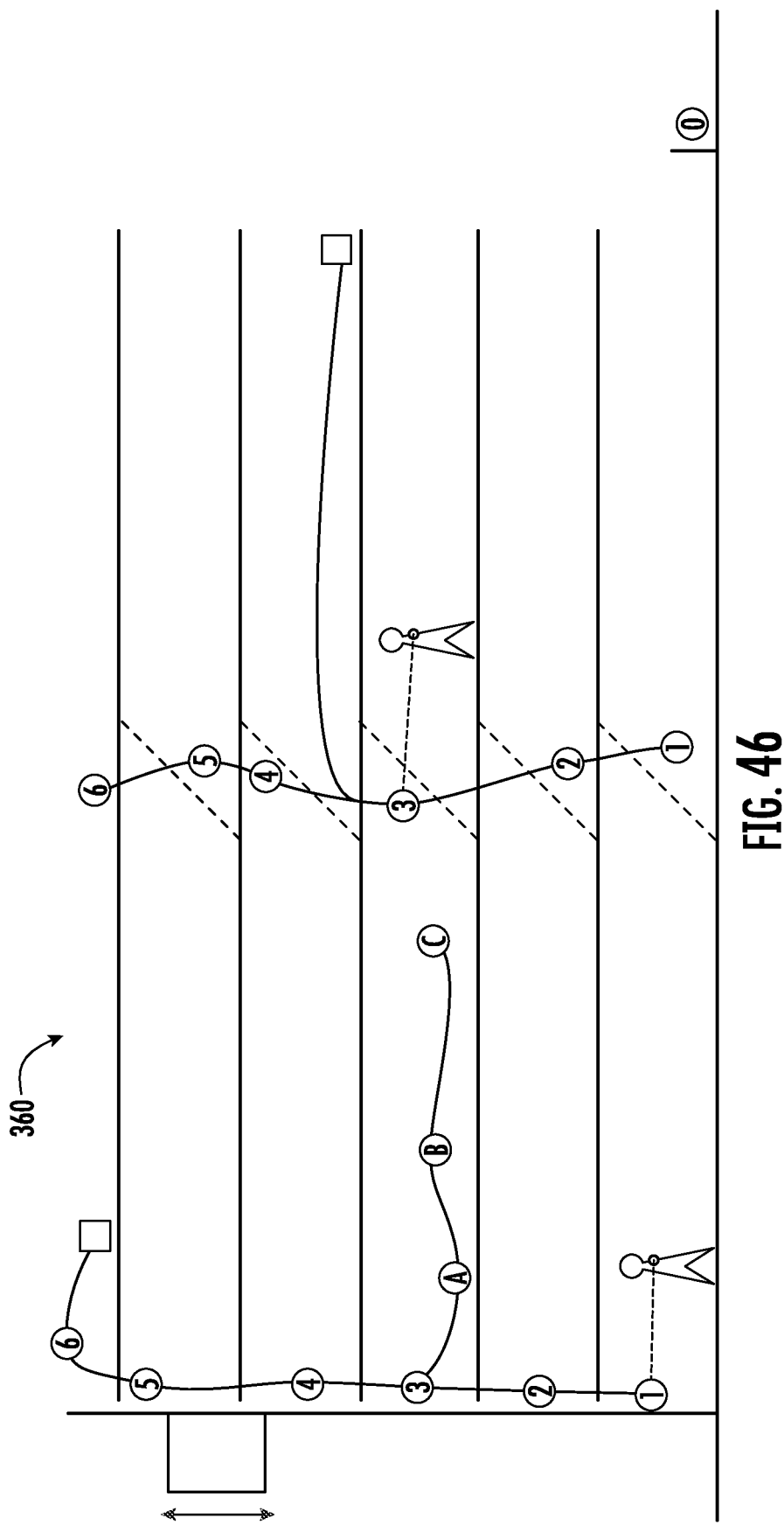
Figure 47:
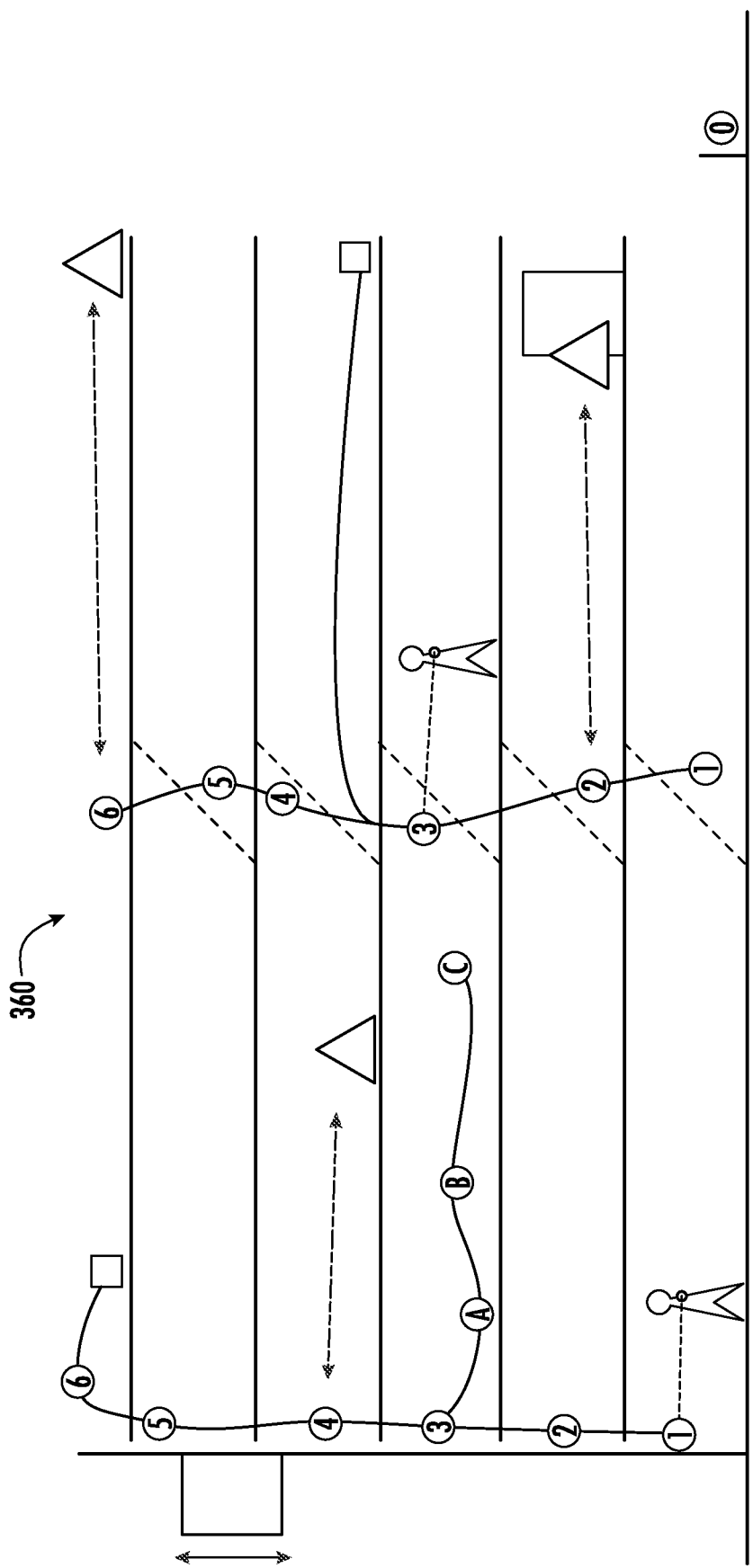

Referring to FIGS. 44-45, in various embodiments a receiver module consists of a battery, an RF module, and a notification source (haptic, visual, or auditory). When out of range of the lock, or when a triggering event occurs at the lock, the receiver will alert the user via its notification source. Different notification types can be given for each scenario.

Referring to FIGS. 46-83, various aspects of keep out zone system 360 are shown. The keep out zone system(s) shown are substantially the same as keep out zone system 10, keep out zone system 110, keep out zone system 210, or keep out zone system 310 except for the differences discussed herein.

Figure 50:
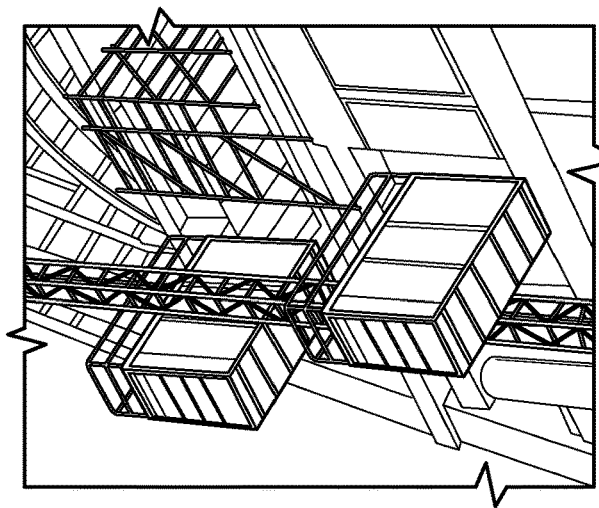
Figure 49:
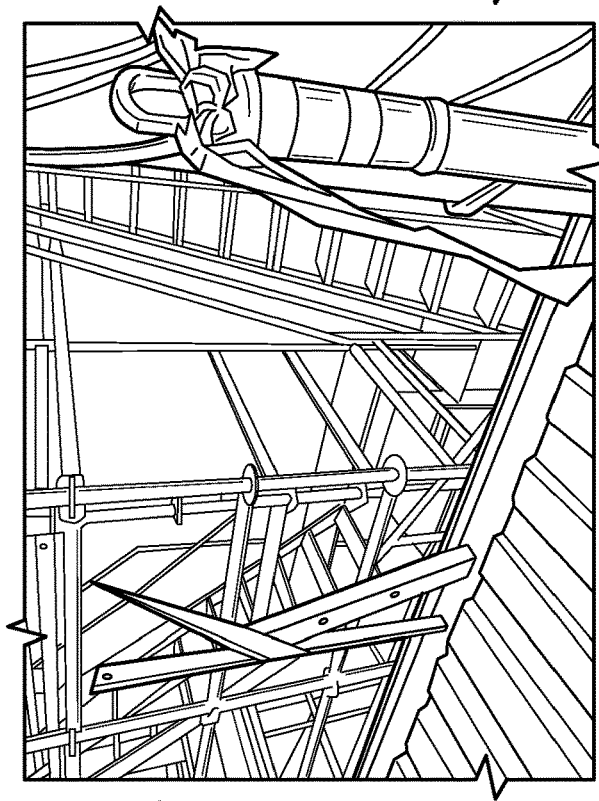
Figure 48:
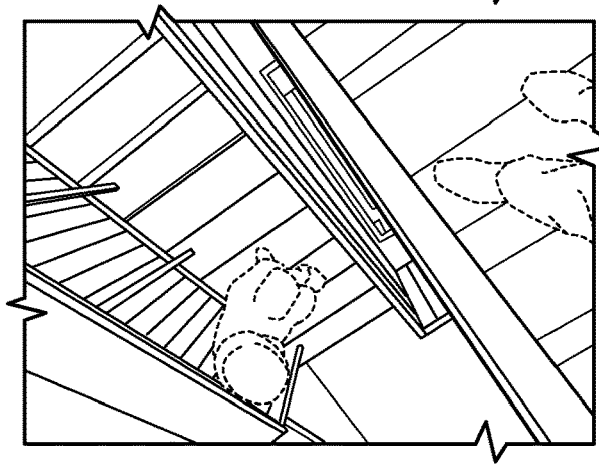

Referring to FIGS. 46-51, the keep out zone system 360 includes one or more monitoring devices that monitor when people and/or devices enter the protected area(s) being monitored. For example, the keep out zone system includes a plurality of monitoring devices in electrical communication with each other. The monitoring devices are arranged at locations of entry and exit for one or more protected areas, such as at elevators (FIG. 48), hoists (FIG. 49), and/or stairways (FIG. 50). In various embodiments workers wear an electronic device, such as a trade tag. When the trade tag approaches and/or transits past one or more monitoring devices, the monitoring devices identify the user and the protected area (e.g., floor 3) that the user entered or exited. In this way, the keep out zone system continuously updates one or more data values that indicate how many people are in each of the protected areas (e.g., the floors of a building). In various embodiments, the monitoring devices communicate, either wirelessly or via wired communications, to a central device what users and/or trade tags the monitoring devices have detected.

Figure 51:
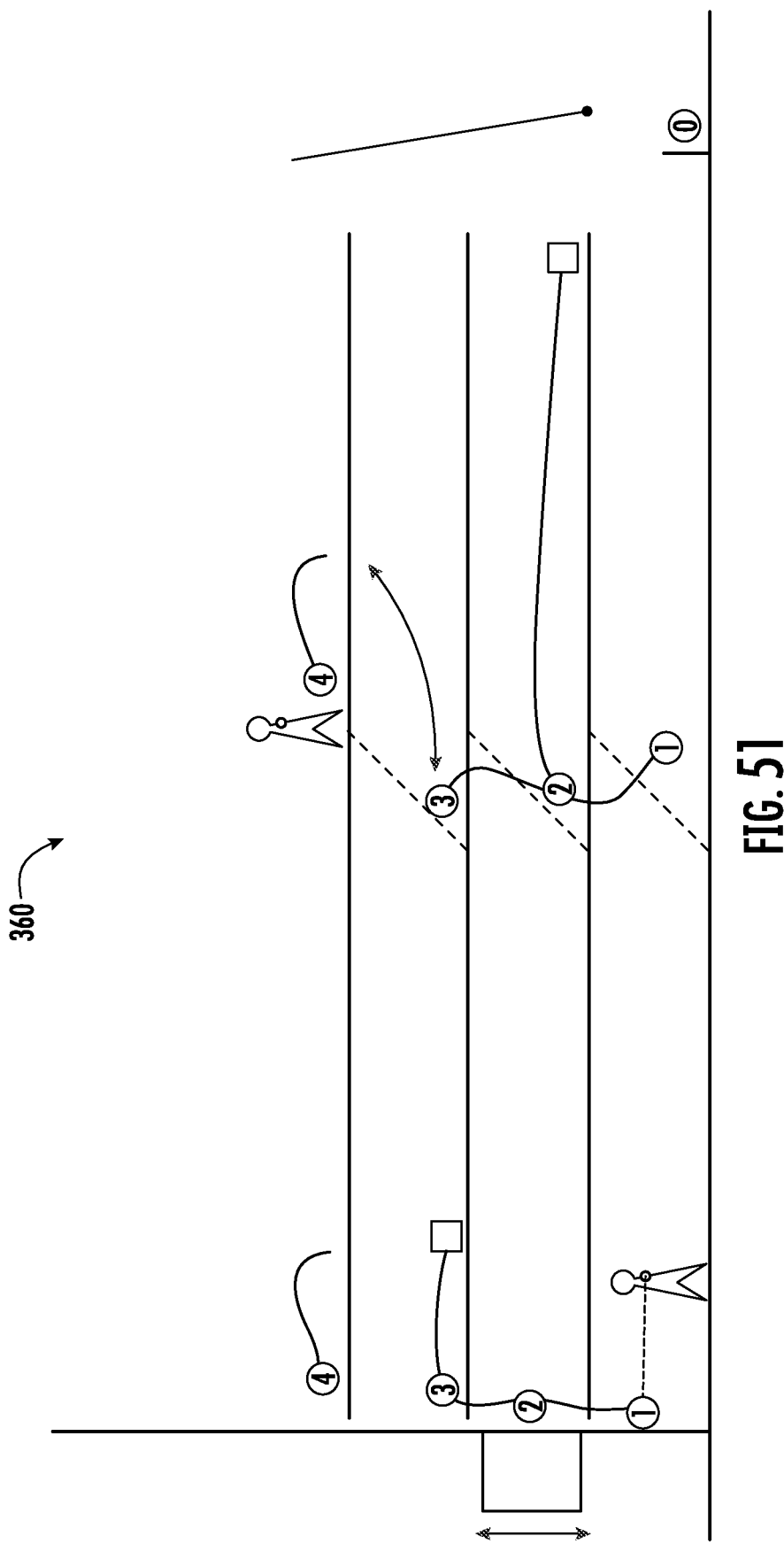

Referring to FIG. 51, in various embodiments the monitoring devices are daisy chained to other monitoring devices. In this way, a plurality of monitoring devices (such as a line of monitoring devices) can be extended to match the expanding size and/or height of the building being constructed. In various embodiments, the construction site entrance (e.g., far right on FIG. 51) is monitored for an added layer of protection and security.

Figure 52:
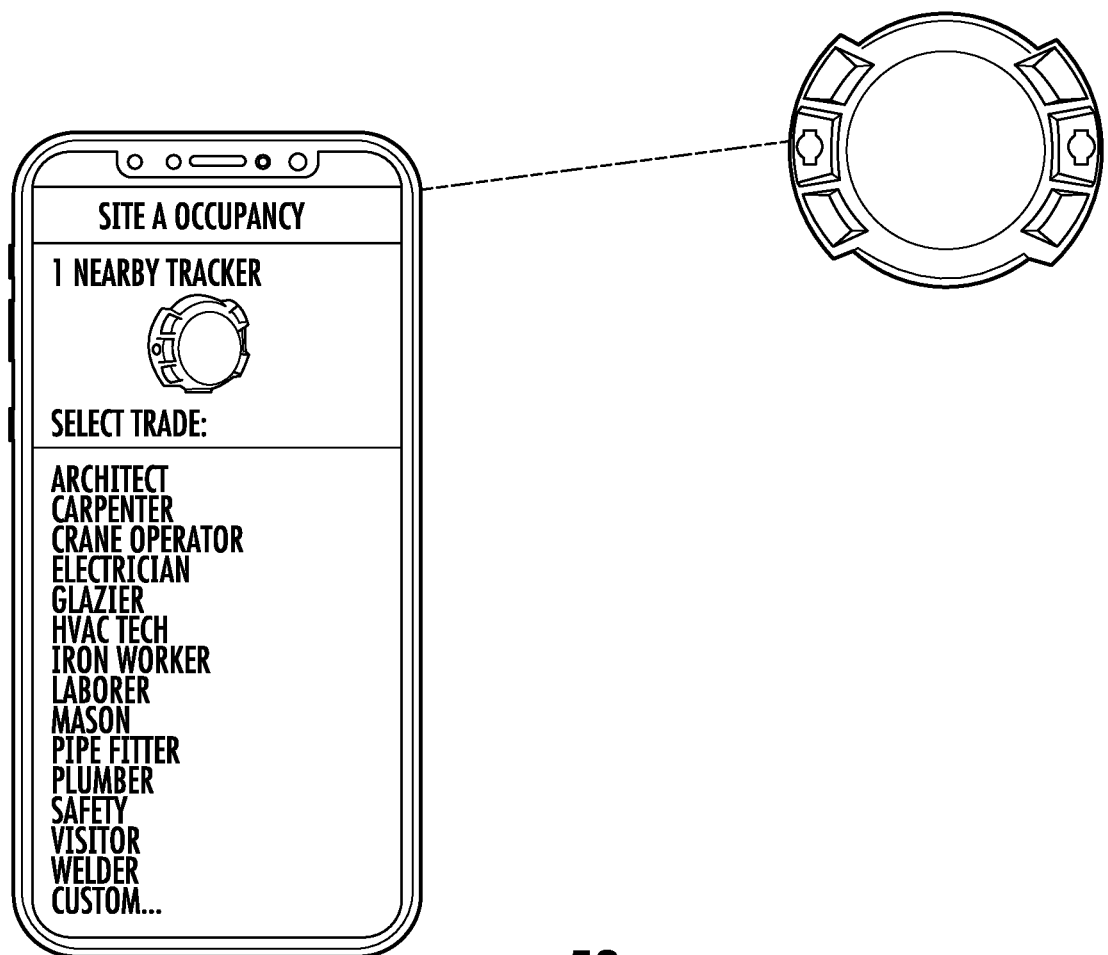
Figure 55:
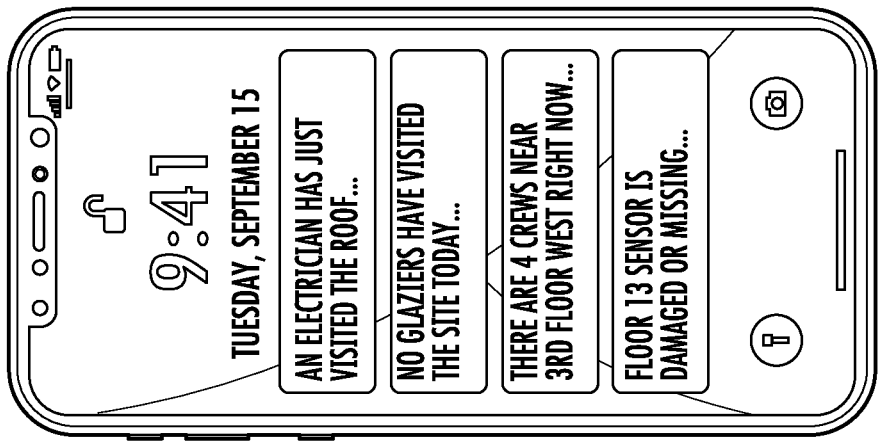
Figure 54:
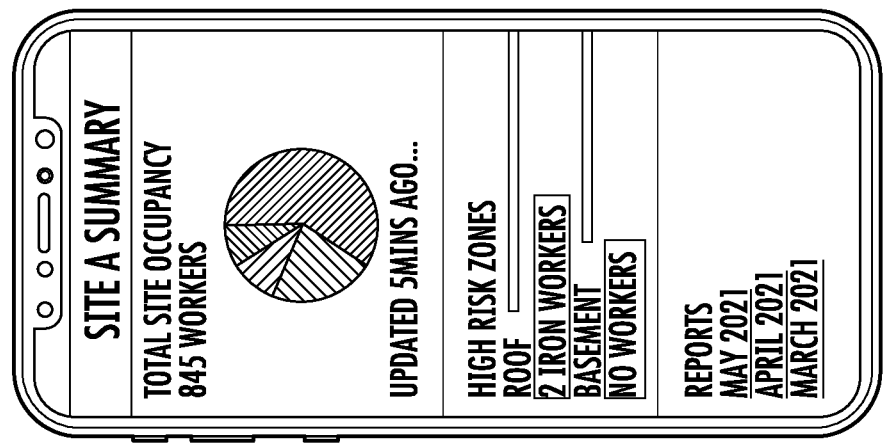
Figure 53:
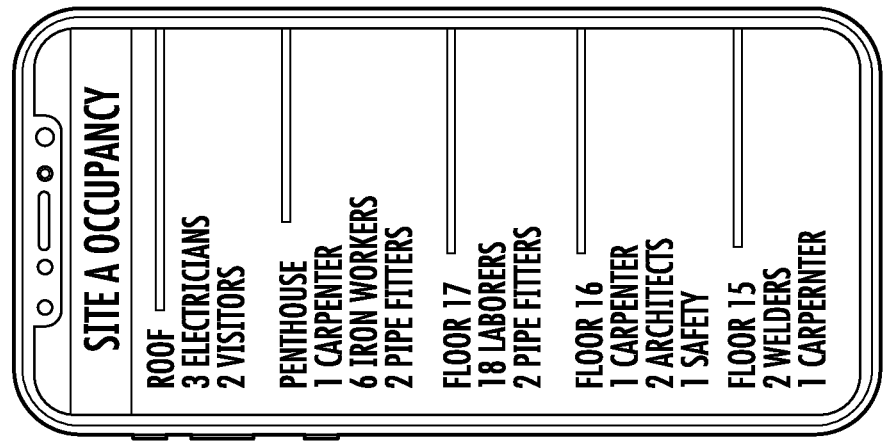
Figure 56:
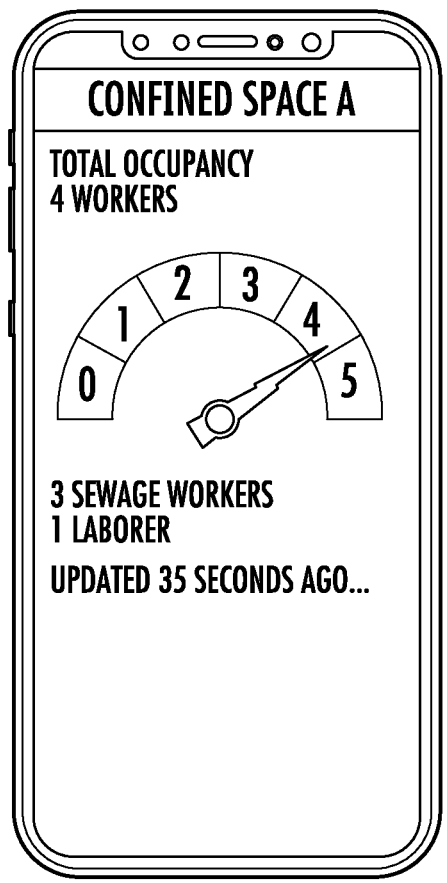
Figure 57:
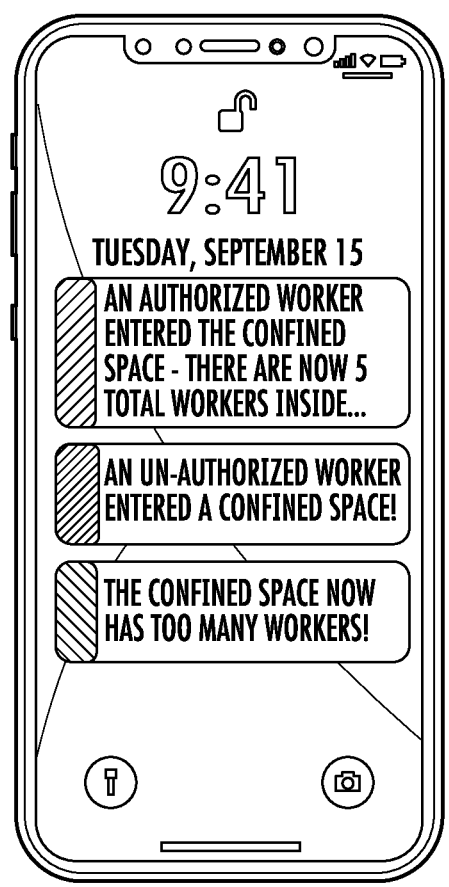
Figure 58:
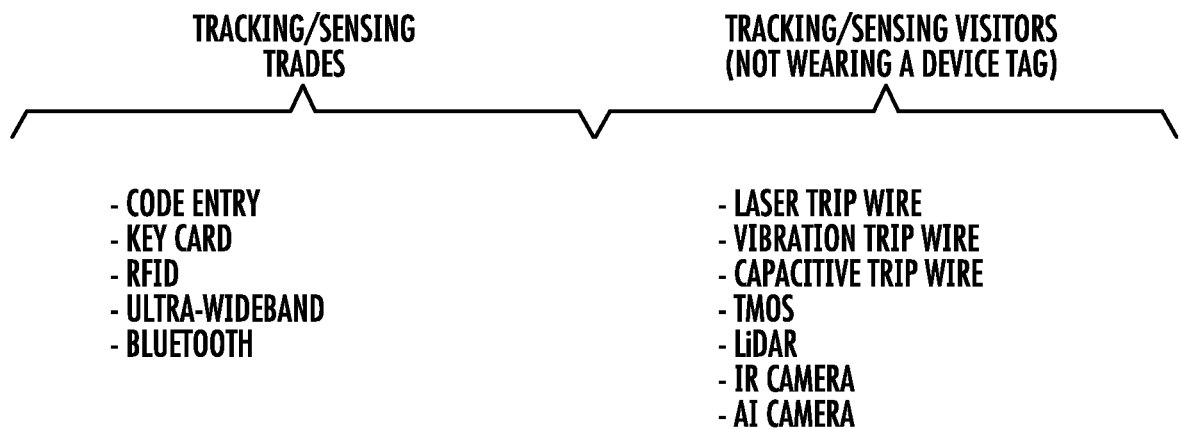
Figure 60:
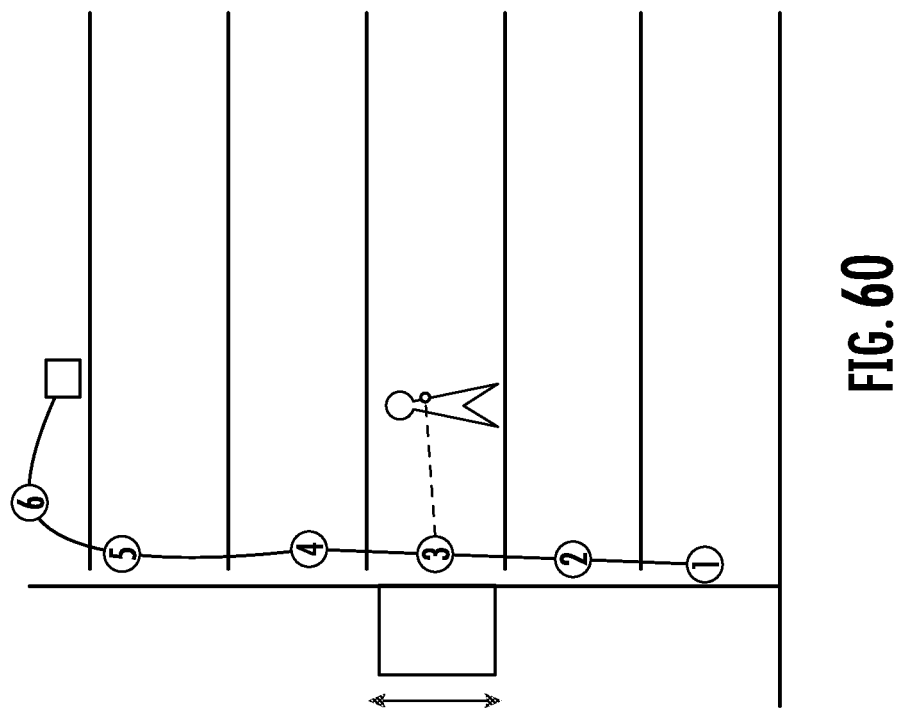
Figure 59:
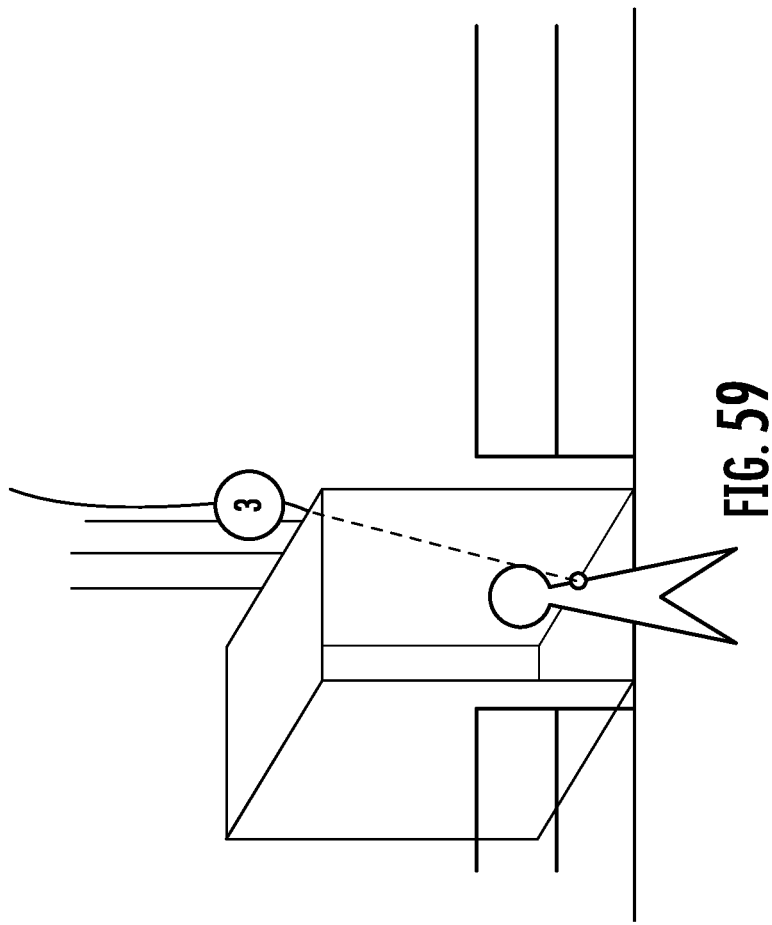
Figure 61:
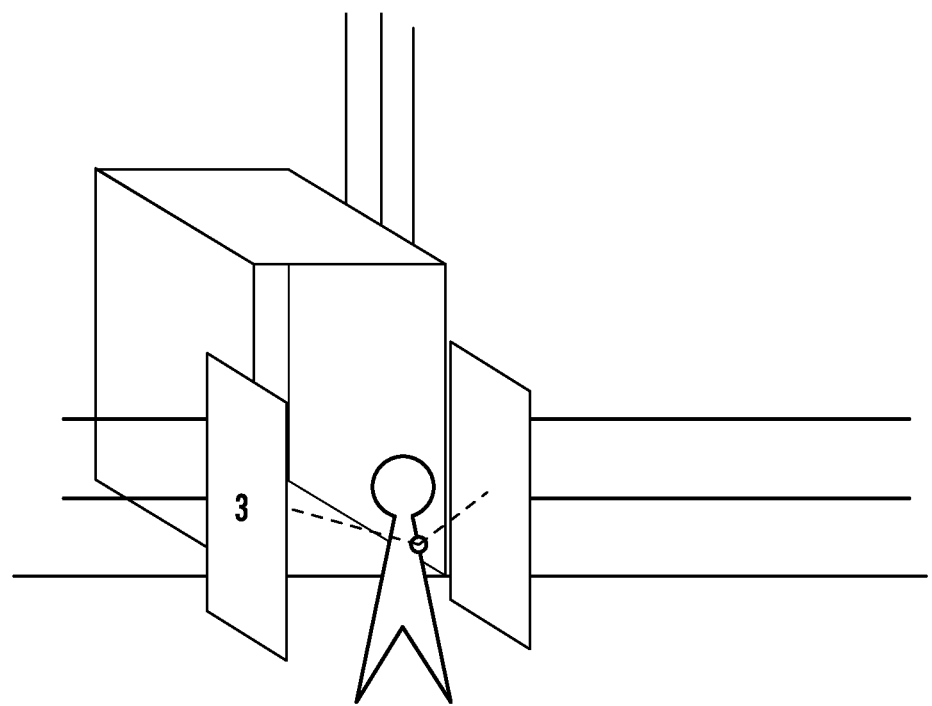
Figure 62:
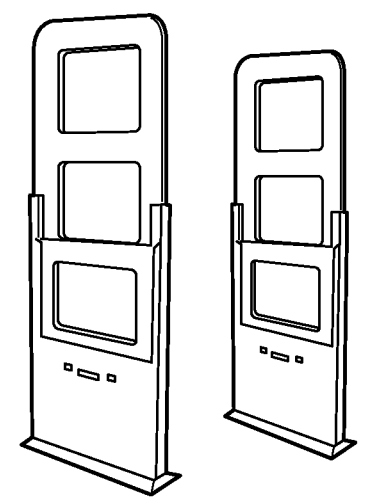
Figure 63:
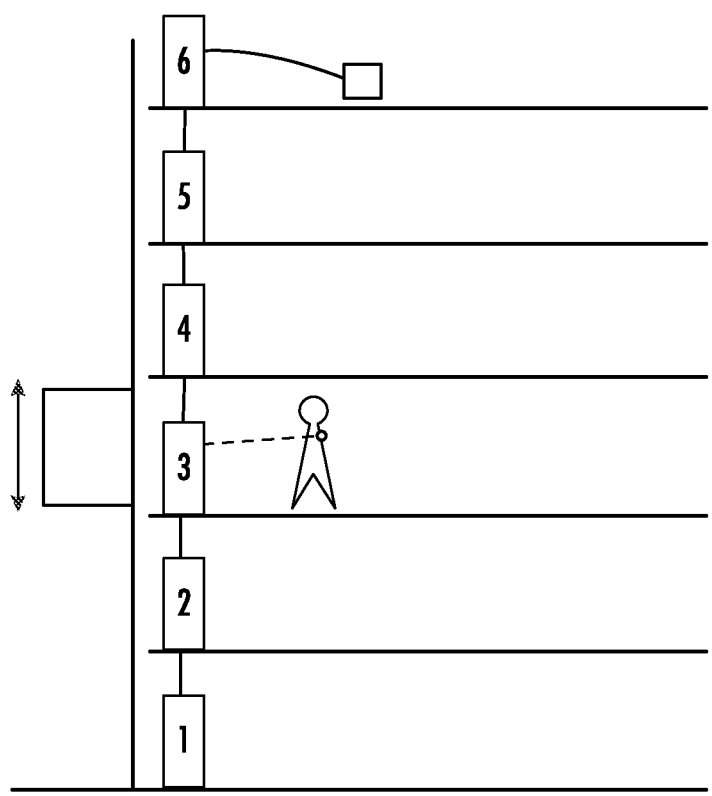
Figure 65:
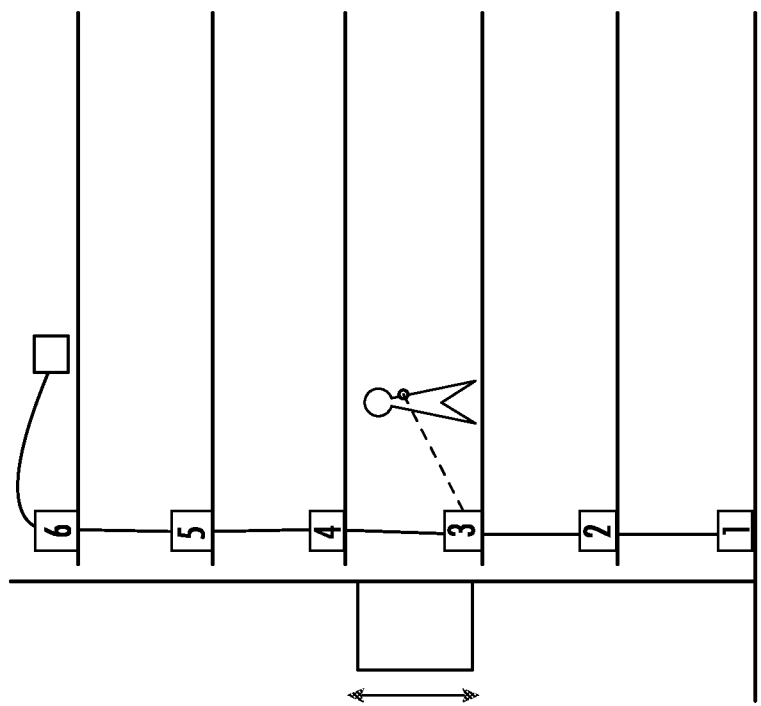
Figure 64:
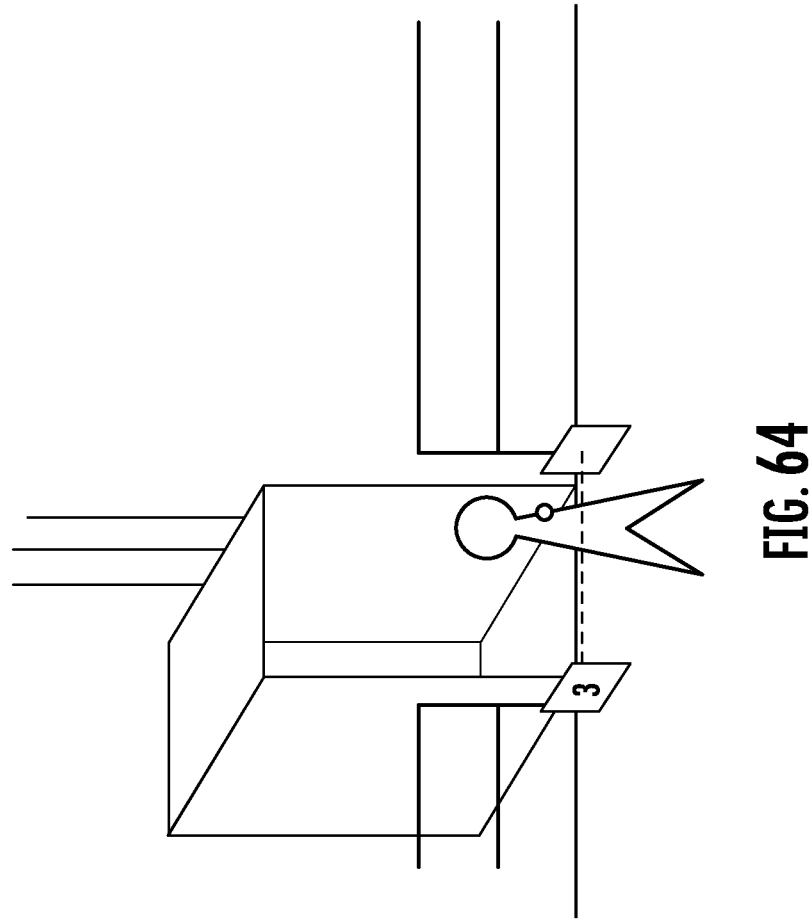
Figure 66:
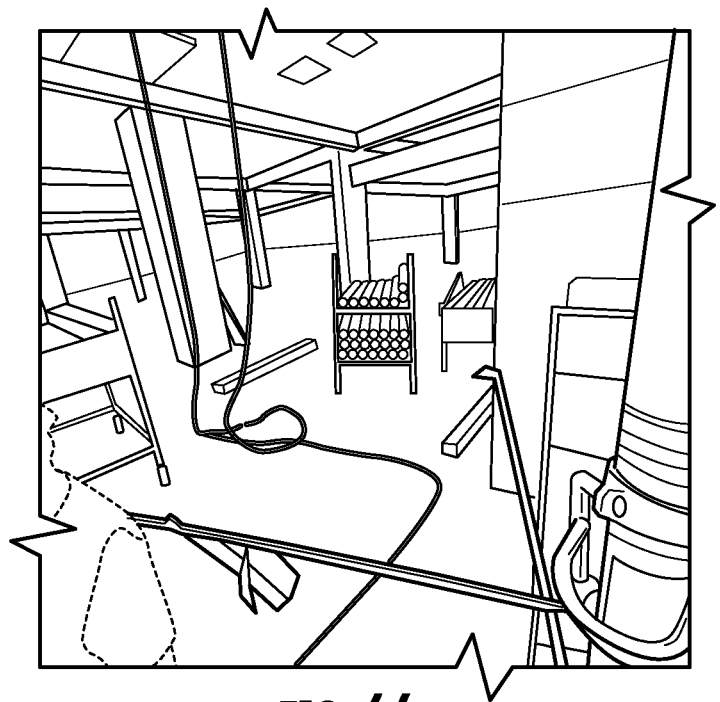
Figure 67:
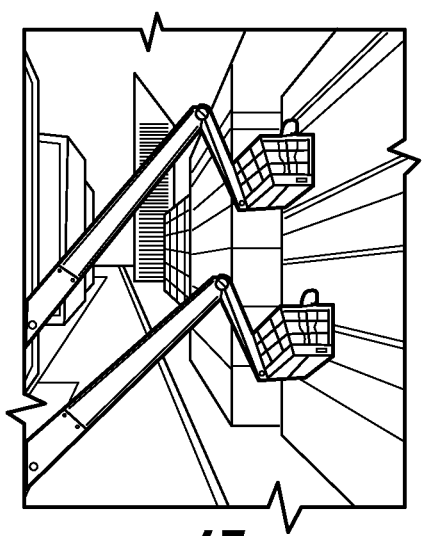
Figure 68:
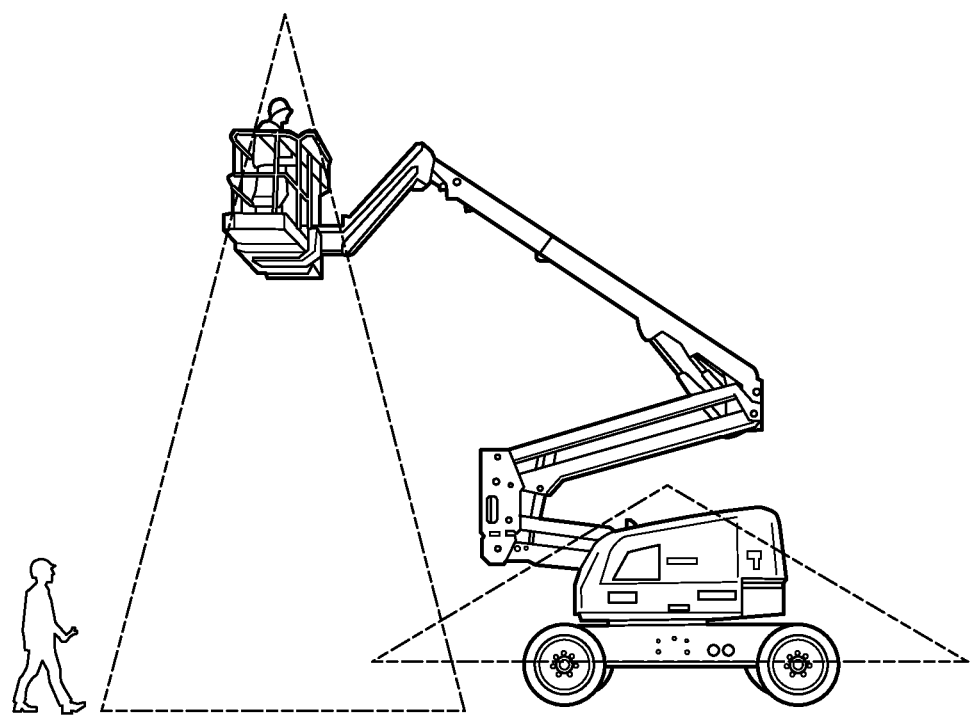
Figure 69:
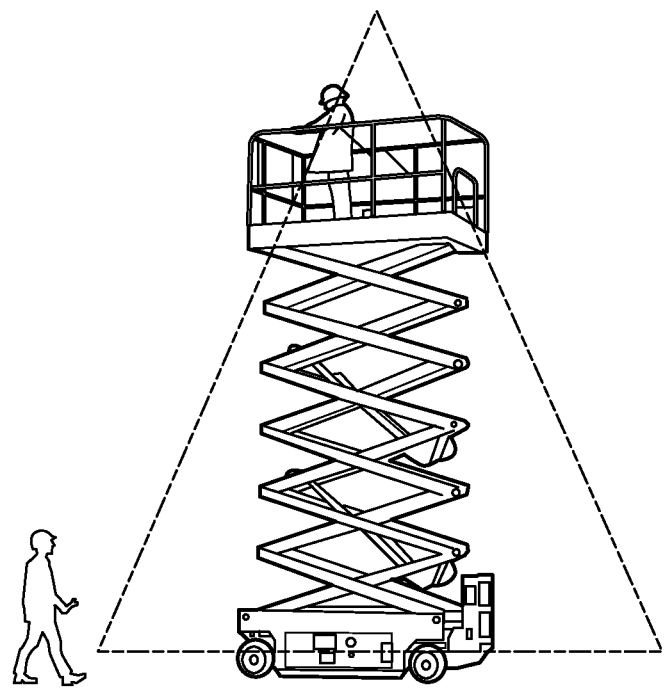
Figure 70:
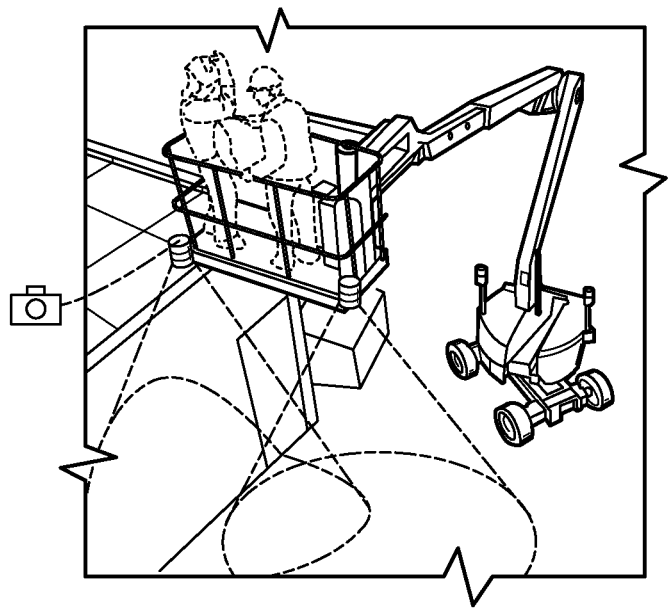
Figure 71:
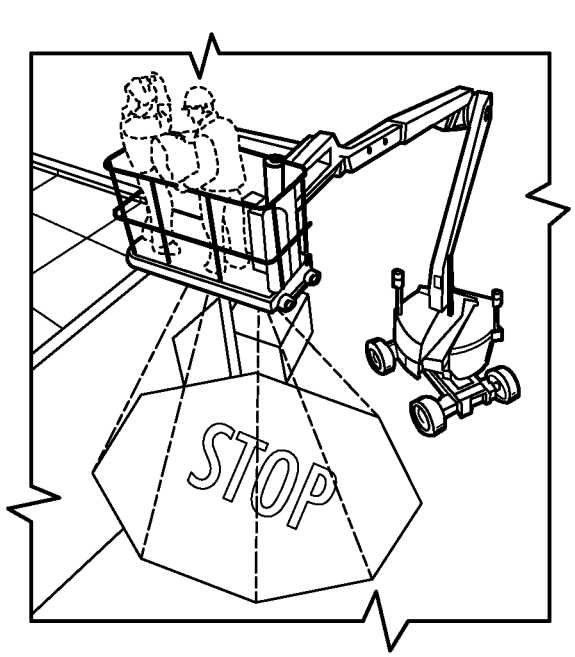
Figure 72:
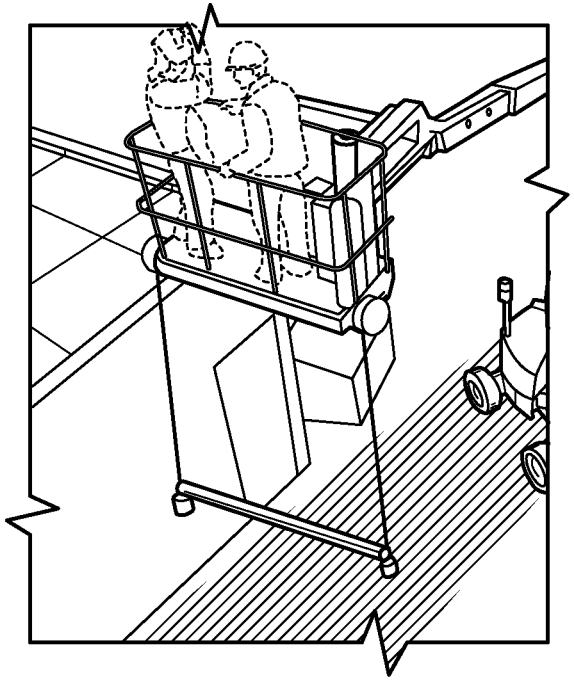

Referring to FIG. 52, in various embodiments the keep out zone system includes electronic tracking devices. When a new workers enters the construction site, the worker selects an electronic tracking device and the electronic tracking device is configured to correspond to the worker (e.g., by selecting the trade of the worker, by entering the name of the worker). In various embodiments the electronic tracking devices are configured to attach to one or more devices associated with the worker, such as a helmet, clothing, and/or a wearable such as a watch.

Referring to FIGS. 53-57, a central system receives data from the one or more monitoring devices. The central system is configured to generate reports, such as real-time reports (e.g., a visual display that dynamically updates as conditions change). The reports indicate various aspects of the data collected by the monitoring devices, such as the trades of the people in various locations. In this way, a person in charge of safety for the construction site may quickly detect if a person is in unsafe area (e.g., if a carpenter is on a floor where only ironworkers are permitted, the report indicates this information to the safety person, who may trigger an alarm). A person in charge of safety can also see if too many people have entered a given area (e.g., five people have entered an area where only four people can safely work at the same time). The central system is also configured to generate alerts, such as alerts to a personal device of a user (e.g., a cell phone), regarding status updates that correspond to the data being collected by the monitoring devices.

Referring to FIGS. 58-65, various structures and methods for tracking/sensing are provided. In various embodiments, the keep out zone system monitors people using code entry (e.g., the user entering a four-digit code), a key card that the user uses to interact with the system, a radio frequency identification (RFID), a system that uses ultra-wideband for detection, and/or a system that uses Bluetooth to detect a nearby user. In various embodiments, the keep out zone system monitors people not wearing a tag such as via a laser trip wire (e.g., a laser projected across an area through which users will pass to enter the safety area), a vibration trip wire to detect vibrations indicating a person or object is moving nearby, a capacitive trip wire to detect a person or object moving nearby, TMOS, a light detection and ranging system (LiDAR), an infrared (IR) camera, and/or a camera that analyzes the captured picture, such as via artificial intelligence (AI). In various embodiments, a communications element, such as a connectivity antenna, is coupled to a line of monitoring devices, and the communications element sends signals including data collected by the monitoring devices. Referring to FIGS. 61-65, users may carry identifying components (e.g., tags) that have low and/or long life batteries and/or users may carry identifying components, such as tags, that do not have a battery.

Figure 73:
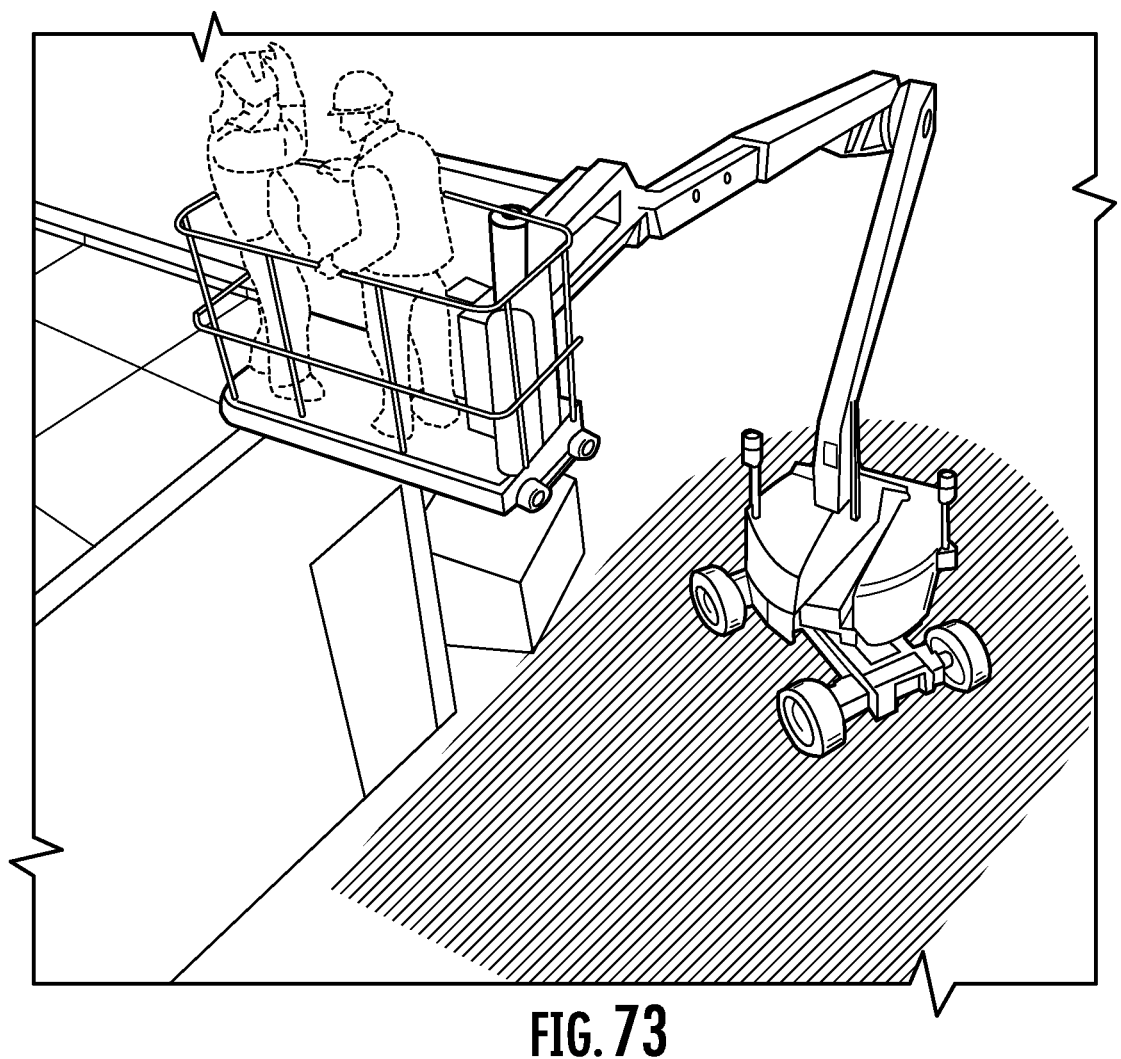
Figure 74:
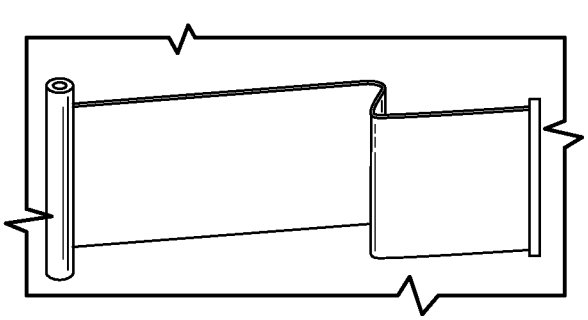
Figure 75:
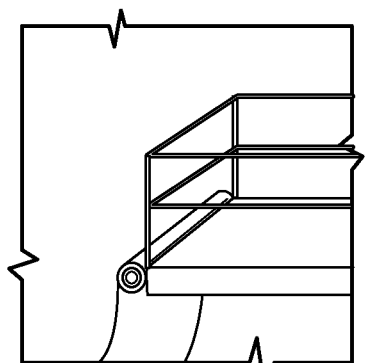
Figure 76:
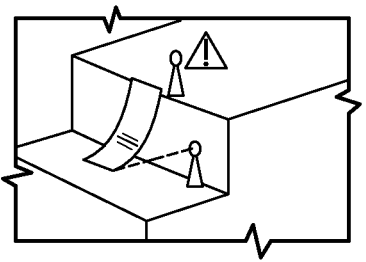
Figure 77:
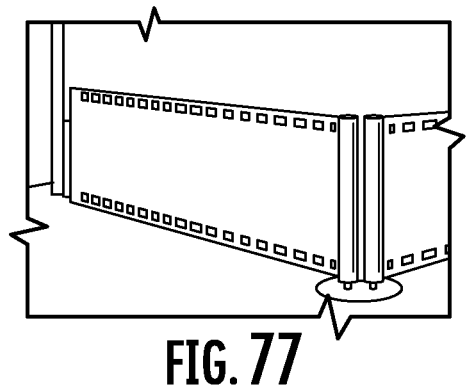
Figure 78:
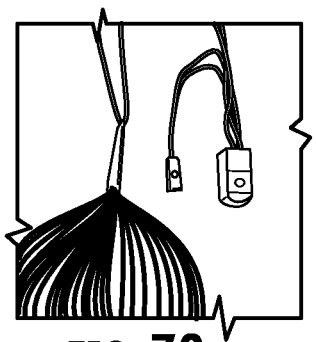
Figure 79:
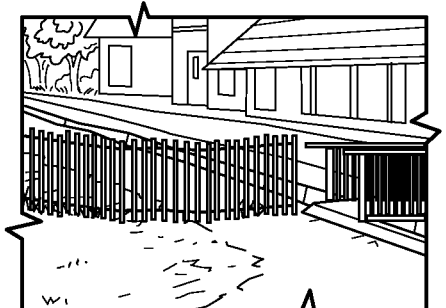
Figure 80:
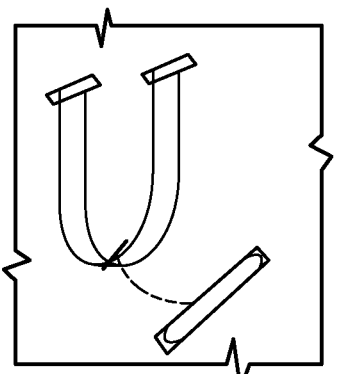
Figure 83:
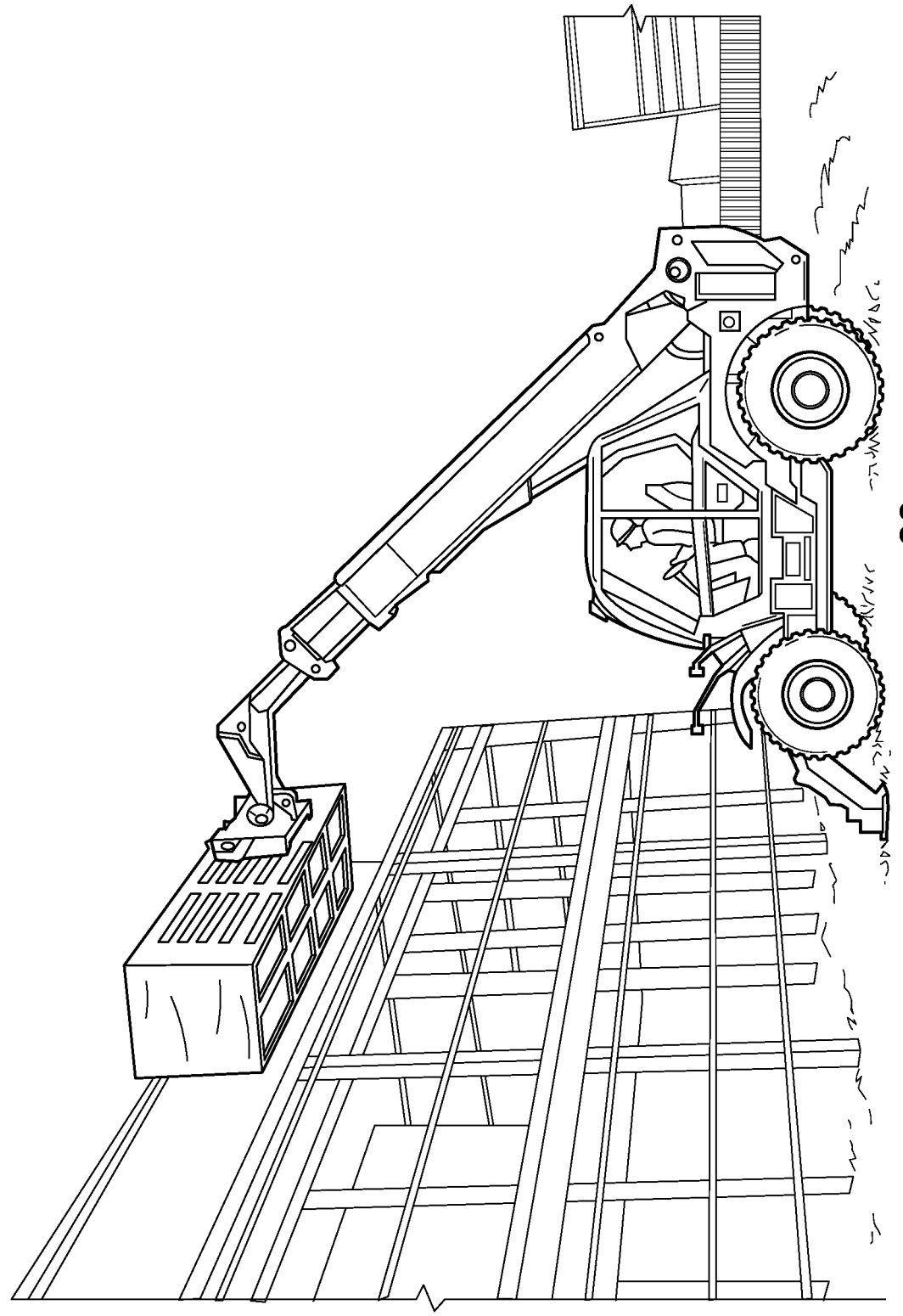
Figure 84:
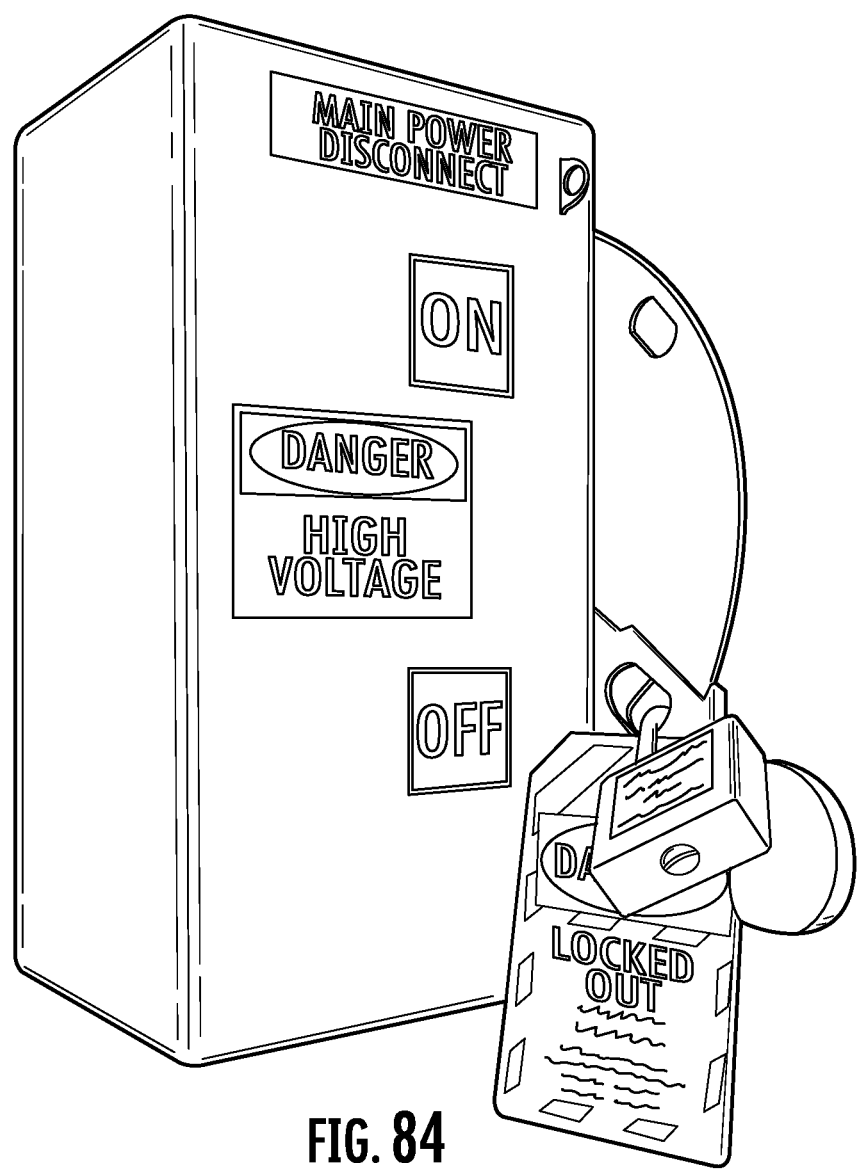
FIGS. 84-97 provide details regarding various aspects and embodiments related to smart tags and/or smart locks for a safety monitoring system.
Figure 85:
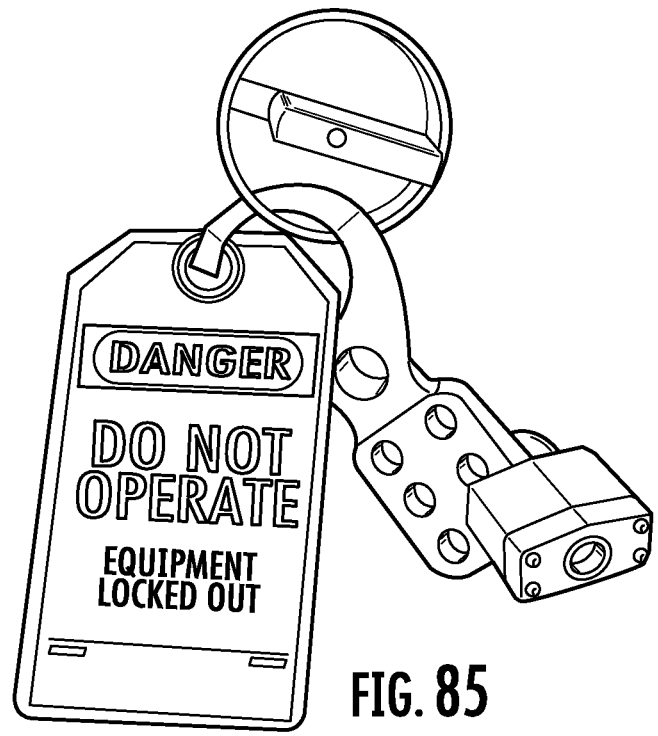
Figure 86:
Figure 87:
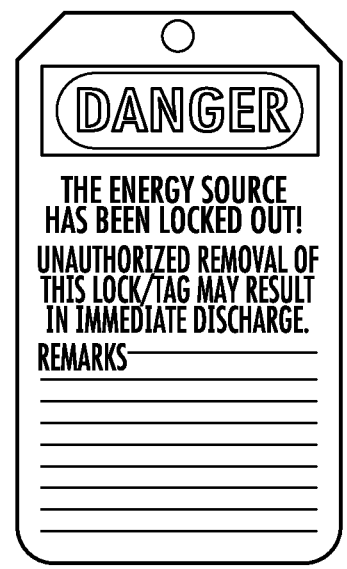
Figure 91:
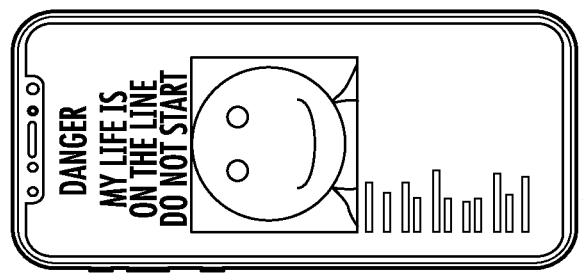
Figure 90:
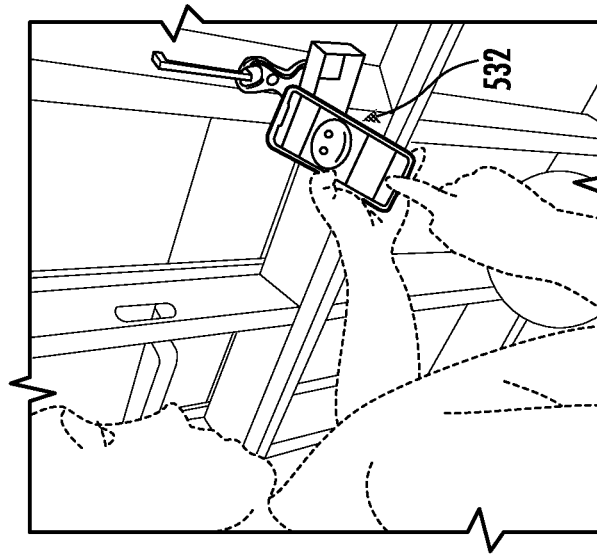
Figure 89:
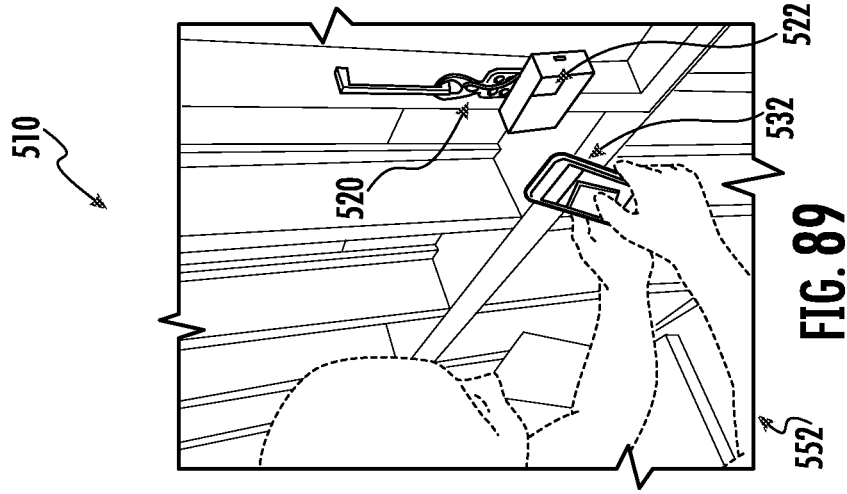
Figure 88:
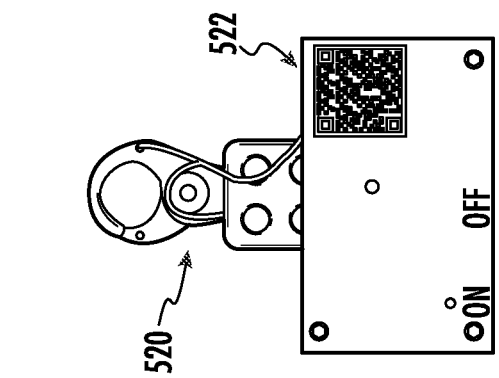

Referring to FIGS. 66-73, a protective system configured to reduce injuries and damage for elevated work platforms is described. In various embodiments, the system includes a sensor that senses below a platform supporting an elevated user (see left-most image in FIGS. 70-72). The sensor can include a camera, LiDAR, a LASER, a sensor that uses ultra-wideband (UWB), and/or a sensor that hangs beneath the platform and detects nearby objects and/or movement approaching the sensor. When the sensor detects a person or object in or near the safety area (e.g., approaching the safety area, such as a protected area), a warning signal is sent to one or more people. The signal may be sent to the people on the platform, the person approaching the safety area, and/or a management or safety person monitoring the safety area or construction site. In various embodiments, the system projects an image below the platform that warns people of the danger, such as an image similar to a stop sign. Referring to FIG. 73, in various embodiments one or more sensors detect around the ground-based equipment supporting the platform, such as via one or more sensors on the platform and/or via one or more sensors on the ground-based equipment.

Referring to FIGS. 74-83, a protective curtain is described. In various embodiments, the curtain is extracted from an object, such as a cylinder, to be deployed around or at a safety area to be protected. In various embodiments, the curtain includes one or more lights (e.g., LED lights). In various embodiments, the light(s) shine on and illuminate the curtain (e.g., lights are at a top of the curtain and emit at least part of the illumination downward to the rest of the curtain).

In various embodiments, a curtain is extended beneath an elevated platform, such as a boom lift (see right-most images in FIGS. 74-80), thus providing the ability to dynamically adjust a vertical height of the curtain and associates sensors. Thus, as the height of the platform is adjusted while the workers in the platform are working on objects at different heights, the curtain may be correspondingly lengthened or shortened so that the curtain extends downward a predetermined distance from the ground. In various embodiments, the curtain includes a proximity and/or touch sensor, a laser sensor, an ultra-wideband sensor, an accelerometer sensor, a gyroscope sensor, and/or a TMOS sensor or system.

Referring to FIGS. 84-97, various aspects of keep out zone system 510 are shown. Keep out zone system 510 is substantially the same as keep out zone system 310 except for the differences discussed herein.

In various embodiments, a smart lockout/tagout is coupled to a device that is temporarily turned off and the lockout/tagout includes a QR code. The QR code provides the ability to identify how long the device has been turned off, who is performing work necessitating the device being turned off, how long before the work is complete, where to contact the person(s) doing the work, the name of the worker(s), the company, the trade, the phone number, and/or supervisor name and contact info.

Referring to FIGS. 88-91, a protection device 520 is coupled to an identifying element, shown as QR code 522. The protection device 520 is coupled to an object to be protected (e.g., a fuse box, gas and/or liquid pipe valves, pneumatic equipment, HVAC, machines, and/or equipment). When another person, shown as intruder 552, approaches the protection device 520, intruder 552 uses an electronic device, shown as personal electronic device 532 to interface with QR code 522, such as by scanning QR code 522. The personal electronic device 532 retrieves information based on the QR code 522, such as by contacting an address identified by the QR code 522. The retrieved information includes one or more of a name of a person, such as worker that placed the protection device 520, a company employing the worker, a trade for the worker, contact information for the worker such as a phone number, a backup contact person for the worker such as a supervisor, a start date/time of the placement of the protection device 520, a projected completion time, a name of the location for the protection device, and/or an address for the protection device. The personal electronic device 532 then communicates to intruder 552 the retrieved information, such as via a display on the personal electronic device 532 (for example, see right-most image in FIGS. 88-91).

Figure 92:
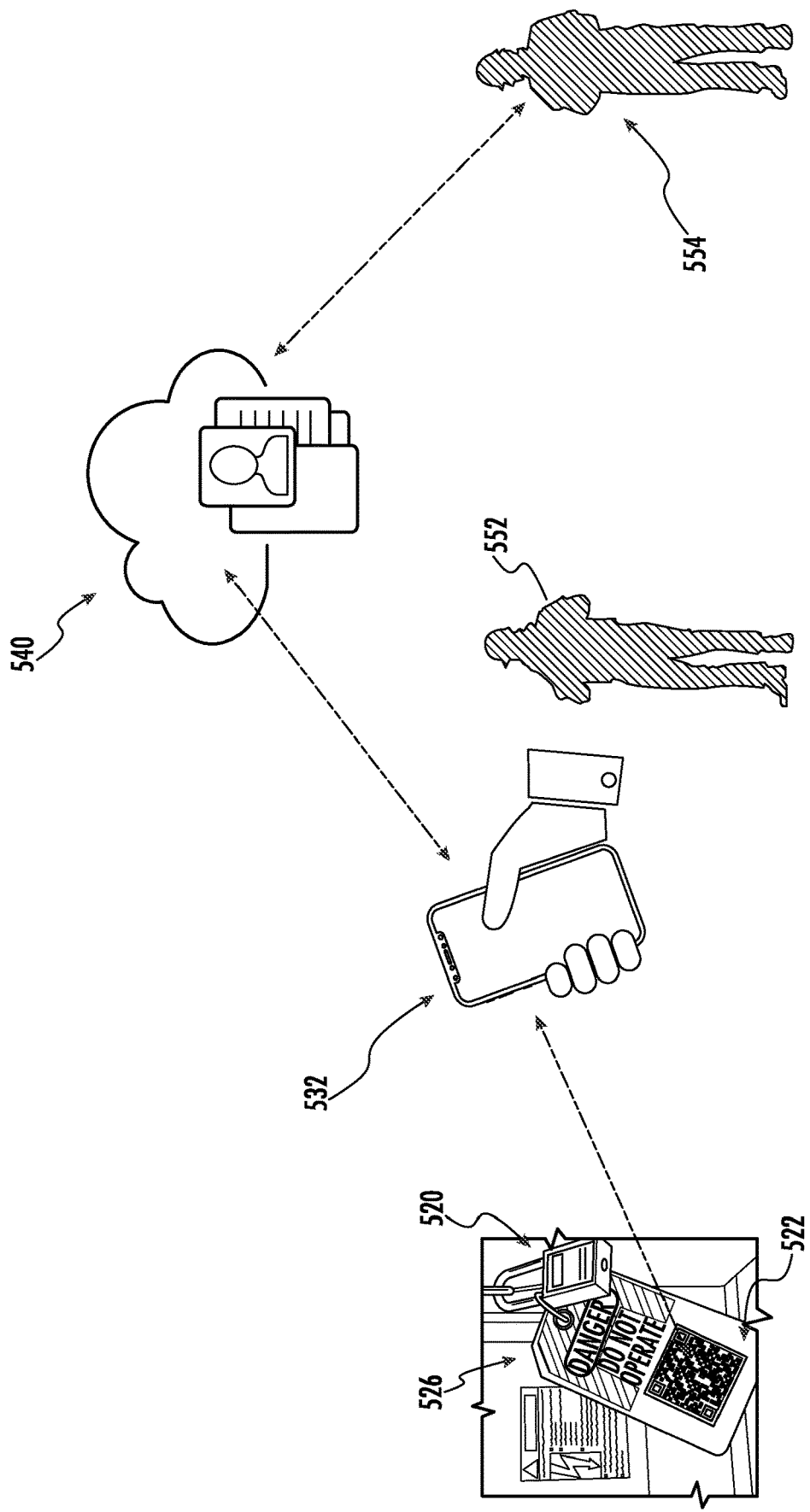

Referring to FIG. 92, in various embodiments QR code 522 is coupled to a communication medium, shown as tag 526. Intruder 552 uses personal electronic device 532 to retrieve the data in QR code 522, such as by scanning QR code 522. The personal electronic device 532 communicates with a central computing system, shown as central server 540, to retrieve information associated with QR code 522. In various embodiments, the central server 540 communicates information about the protection devices 520 and/or QR codes 522 to other people, such as safety manager 554 in charge of monitoring the construction site for dangers.

Figure 93:
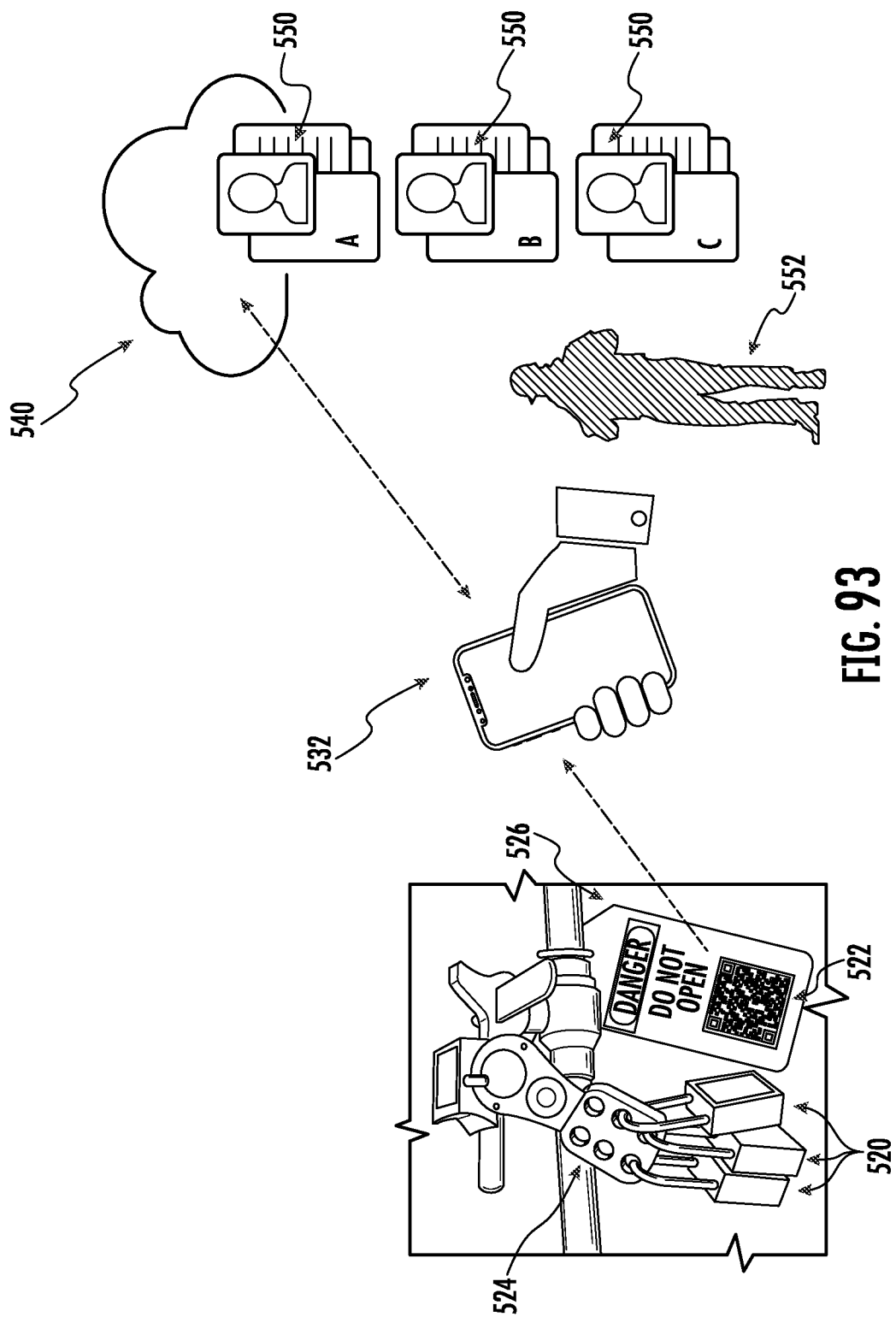

Referring to FIG. 93, in various embodiments a device that couples to multiple protection devices 520, shown as multiple-receptacle device 524, is shown. One or more protection devices 520 are coupled to the multiple-receptacle device 524, and a tag 526 with a QR code 522 is also coupled to the multiple-receptacle device 524. When personal electronic device 532 retrieves information from central server 540 based on QR code 522, the information identifies one or more of the people that placed the protection devices 520, shown as workers 550.

Figure 94:
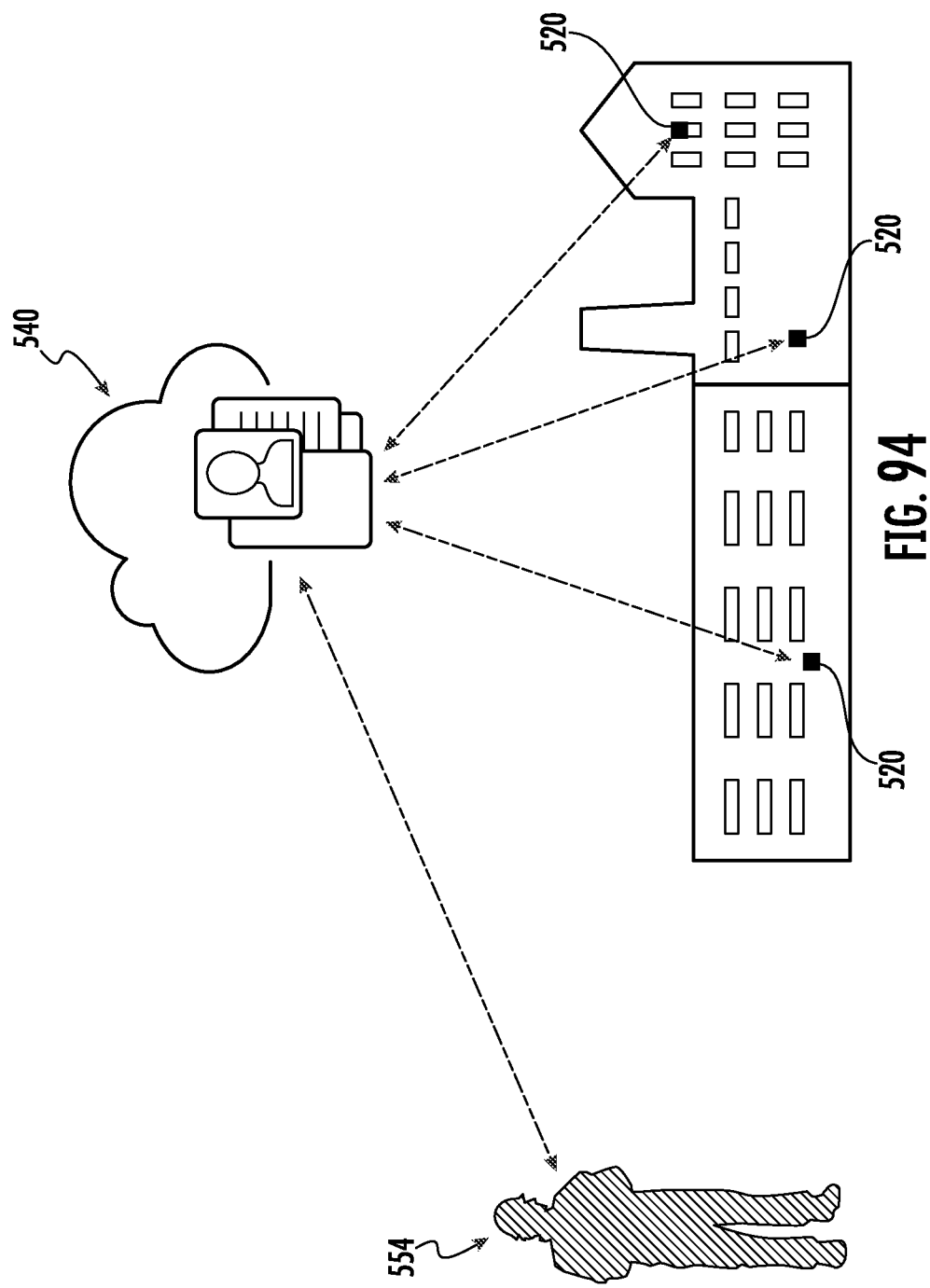
Figure 95:
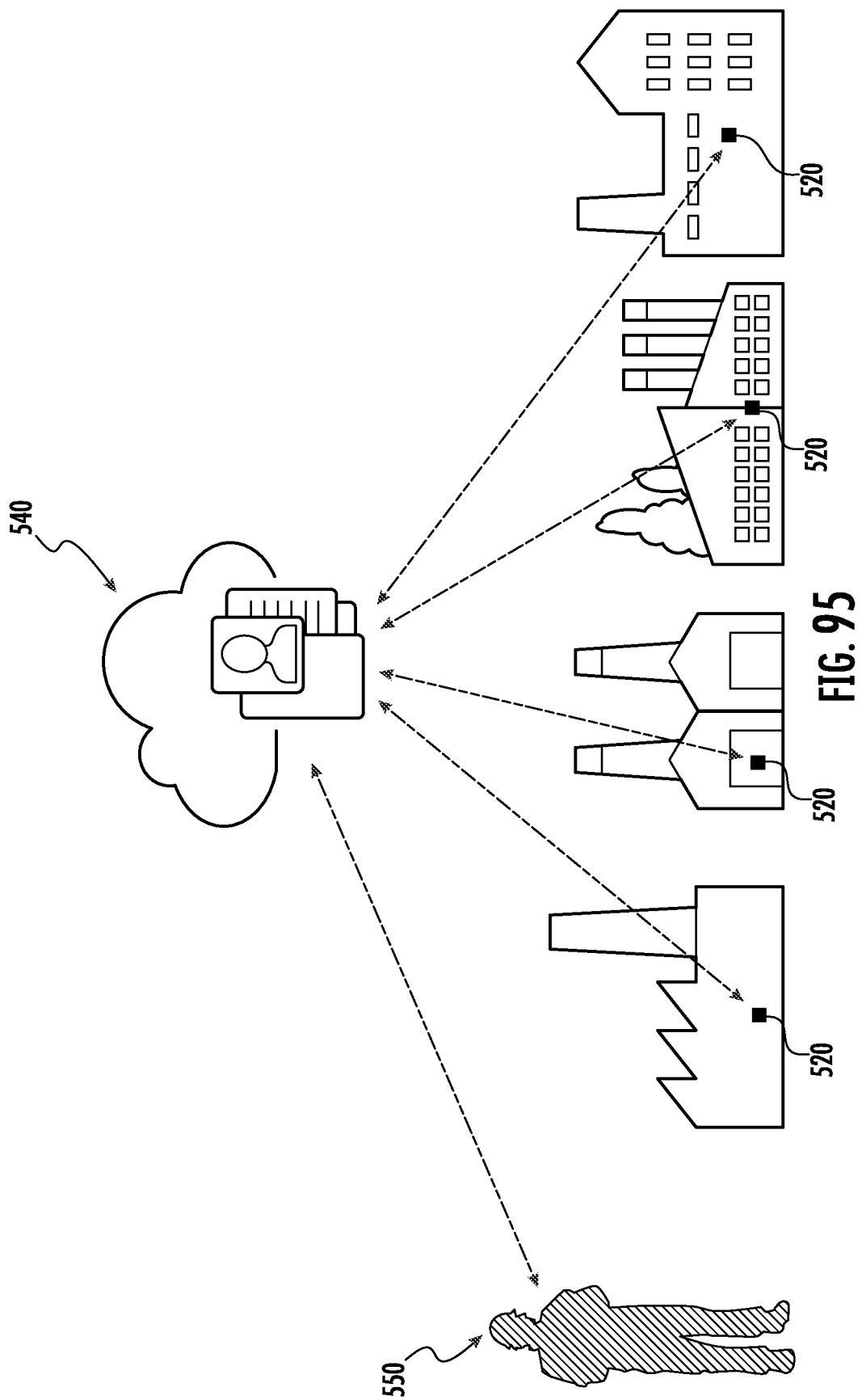

Referring to FIGS. 94-95, in various embodiments central server 540 monitors multiple protection devices 520 at one or more locations. The central server 540 is configured to communicate information about the protection devices 520 to various people, such as safety manager 554 and/or a worker 550 in charge of one or more of the protection devices 520. In various embodiments, the worker 550 can sort and see all active protection devices 520 in the field, all protection devices 520 at a single location, and/or all workers that have attached a protection devices 520 to a single protected device (e.g., a source of energy, such as a fuse box).

Figure 96:
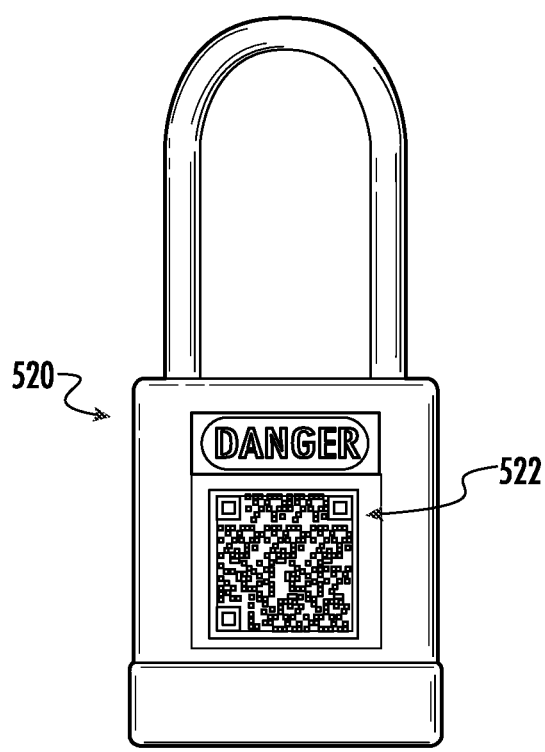
Figure 97:
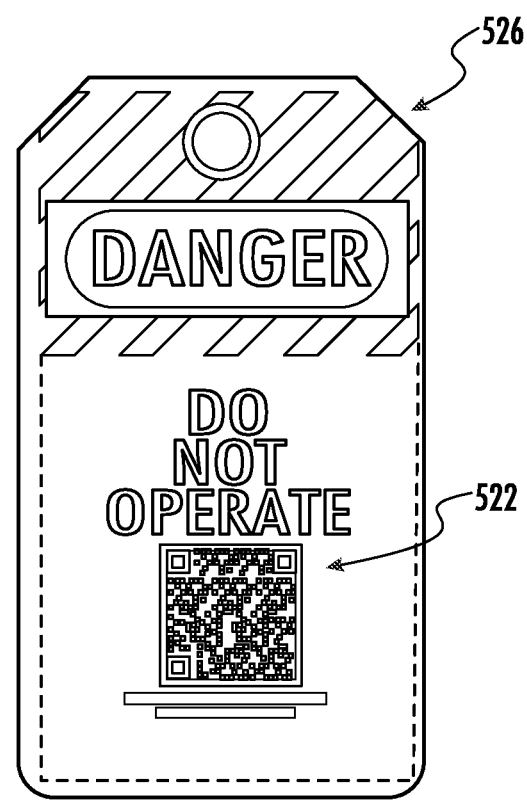

Referring to FIGS. 96-97, a QR code 522 is coupled to a protection device 520. Alternatively, or in combination with a QR code 522 coupled to a protection device 520, a QR code is coupled to a tag 526.

FIGS. 98-112 describe various embodiments of a keep out zone system 610 that includes whole site occupancy monitoring, hazard monitoring, and task zones, such as contractor or subcontractor task zones.

As background, on various worksites sub-contractors are required to consider a Jobsite Hazard Analysis (JHA) and develop a safety plan to address the risks noted in the JHA. When a general contractor is using various embodiments of a keep out zone system, the general contractor can constantly and remotely monitor the compliance of the sub-contractor with the safety plan. For example, the system can confirm to a general contractor that a smart zone has been set up, enabled, and is still active. As another example, the system can trigger an alarm if an unauthorized person enter a smart zone, and log the identity of the person, their employer, their job, and other aspects of that person.

Referring to FIG. 98, the responsibilities of the general contractor are shown in the left column, the responsibilities of the sub-contractor are shown in the right column, and analysis and plans are shown in the center column. Various embodiments of the keep out zone system described herein permit the general contractor to continuously and remotely monitor the worksite and the people on the worksite, and in particular whether the safety plan is being executed (see bottom two entries in the general contractor column). As a result, if non-compliance is detected, such as not setting up a smart zone or unauthorized people repeatedly entering smart zones, the general contractor can address the issue with the sub-contractor before the situation becomes more serious (e.g., before personal injury and/or damage).

Referring to FIGS. 99-100, various aspects of a monitoring device, shown as a smartzone field monitoring stand 620, are shown. In an exemplary use, a person, such as a general contractor, links the stand 620 to a specific JHA. Then, when the stand 620 is placed in the field, the general contractor can confirm the stand 620 is active, receive alerts if any dangerous conditions arise, and receive reports regarding the ongoing status of the smartzone the stand 620 is monitoring.

Figure 101:
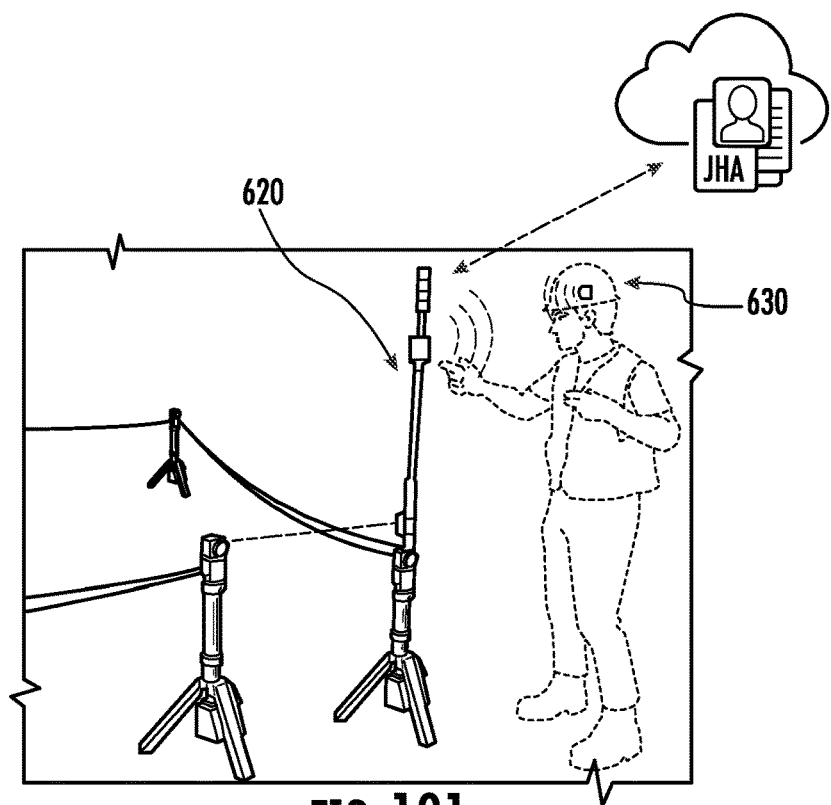
Figure 102:
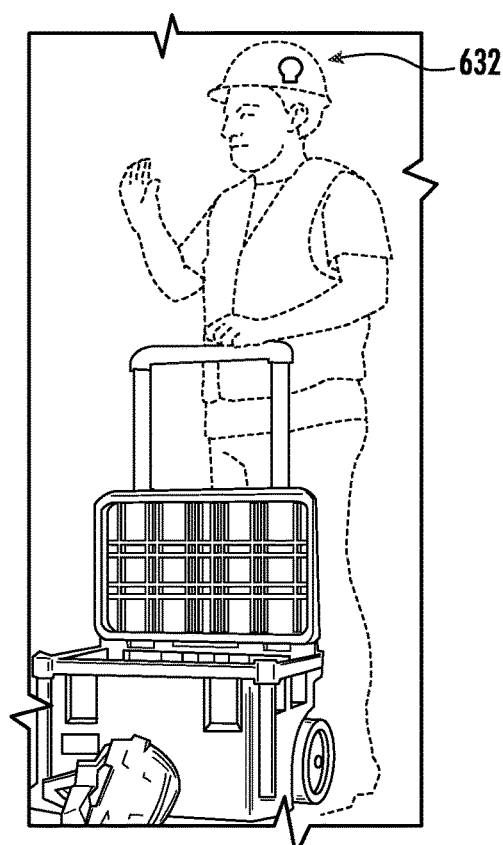

Referring to FIGS. 101-102, various aspects of people entering a smart zone are shown. Referring to FIG. 101, the smart zone, such as via a monitoring stand, identifies that the person approaching the smart zone is authorized to enter the smart zone. For example, the smart zone determines the identity and/or rights of the person by interacting with an electronic device 630 on the person, such as a puck attached to the person's helmet, that indicates the person is authorized to enter the zone. The stand 620 therefore permits the person to walk past the gate. Referring to FIG. 102, the smart zone, such as via a monitoring stand 620, identifies that an unauthorized person is approaching the smart zone and therefore triggers an alert. For example, the stand 620 identifies an electronic device 632 attached to the person. In various embodiments the alert is sent to the person entering the zone, to the people working in the smart zone, and/or to a person in charge of monitoring the smart zone(s).

Figure 103:
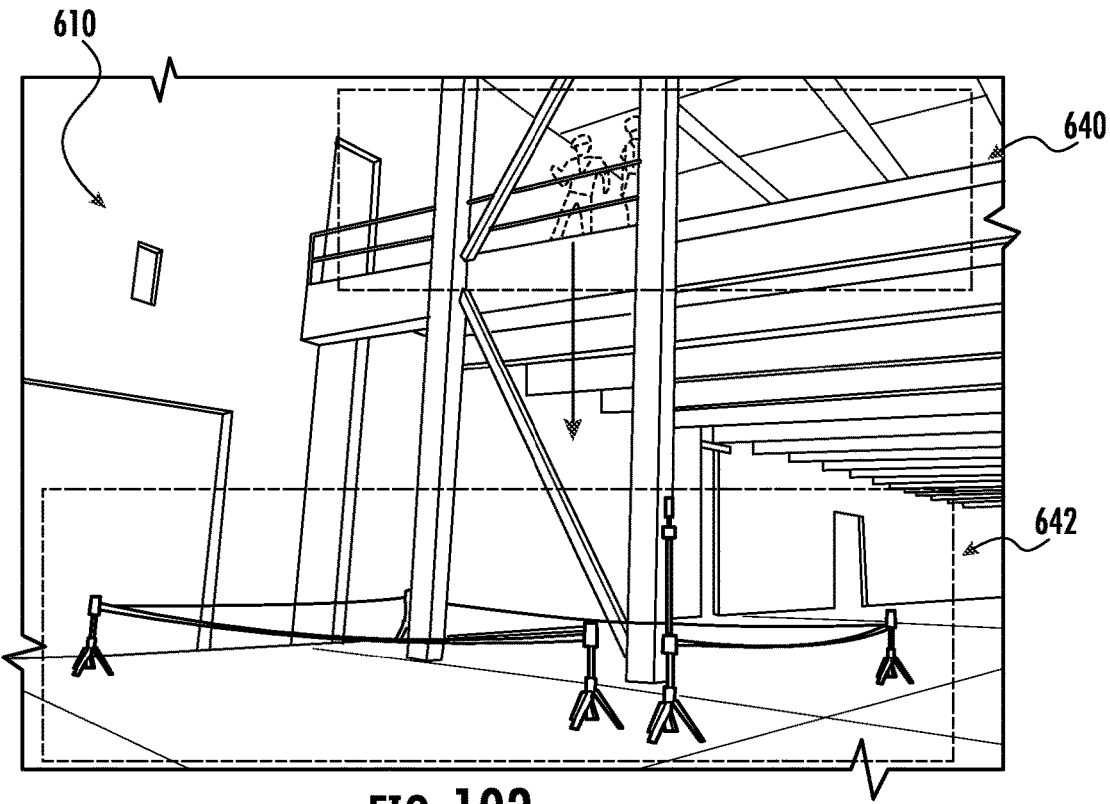
Figure 104:
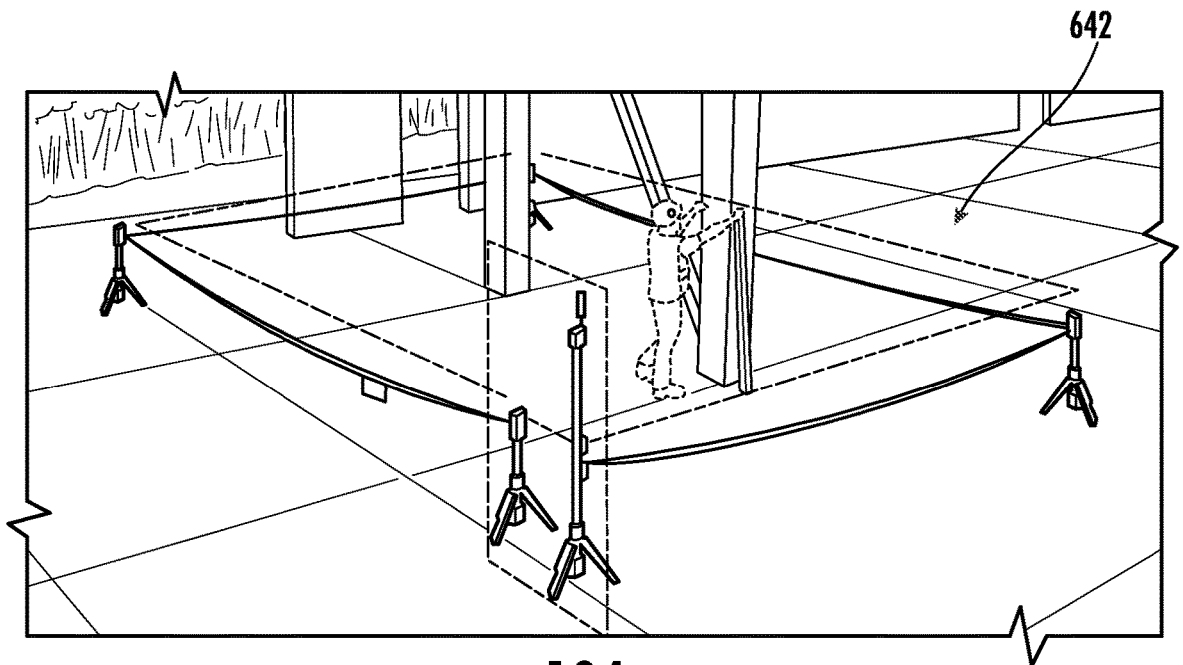
Figure 105:
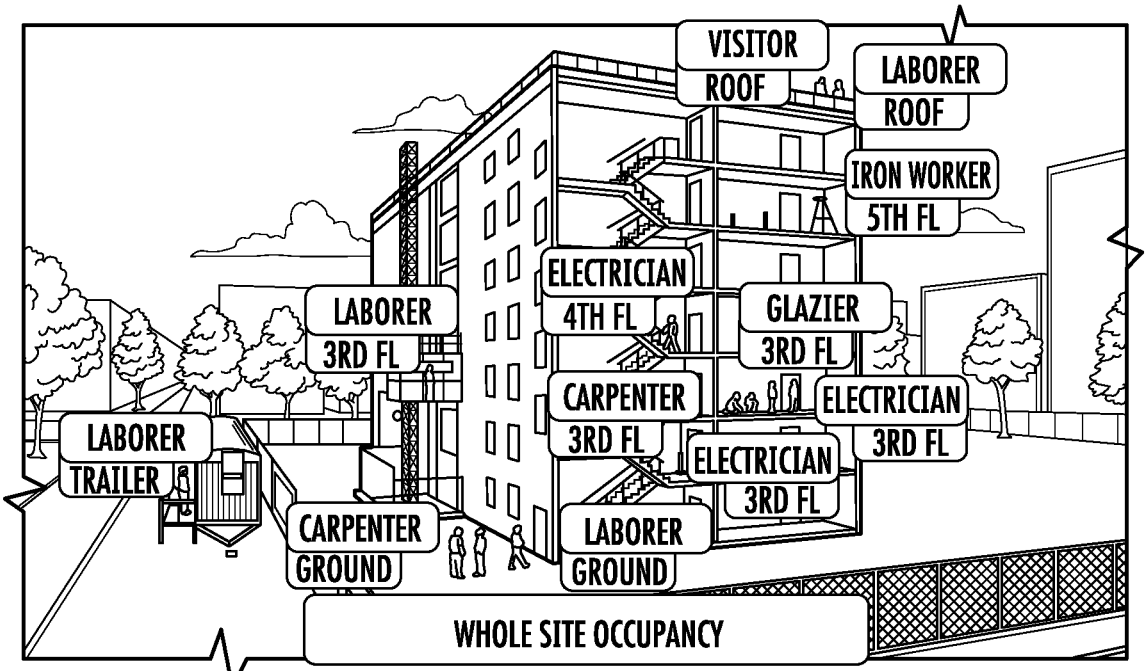
Figure 106:
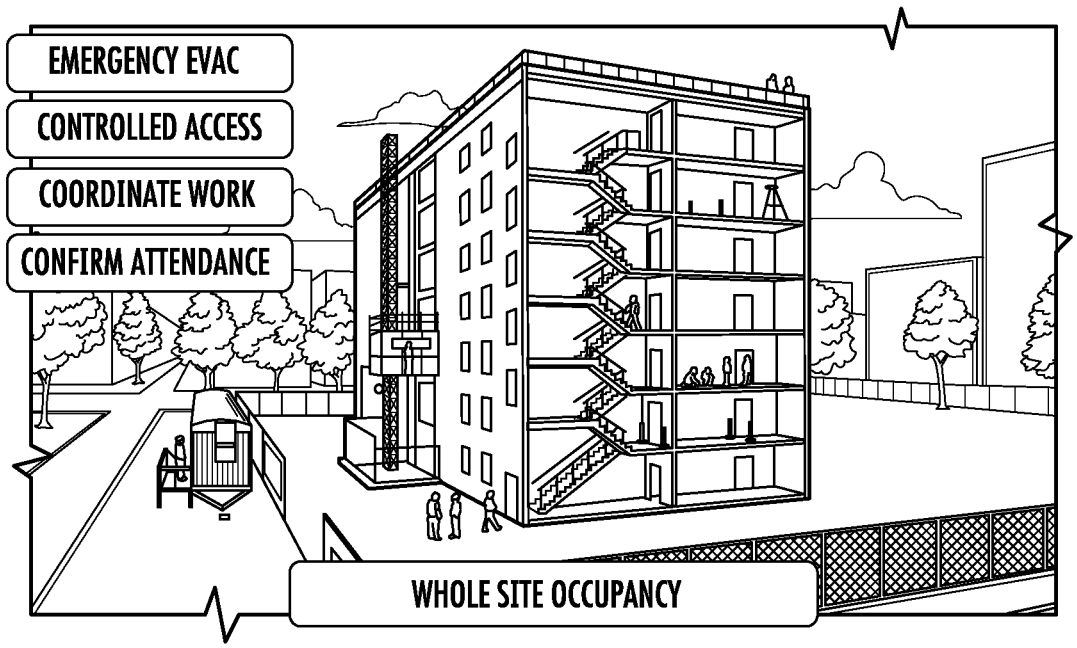
Figure 107:
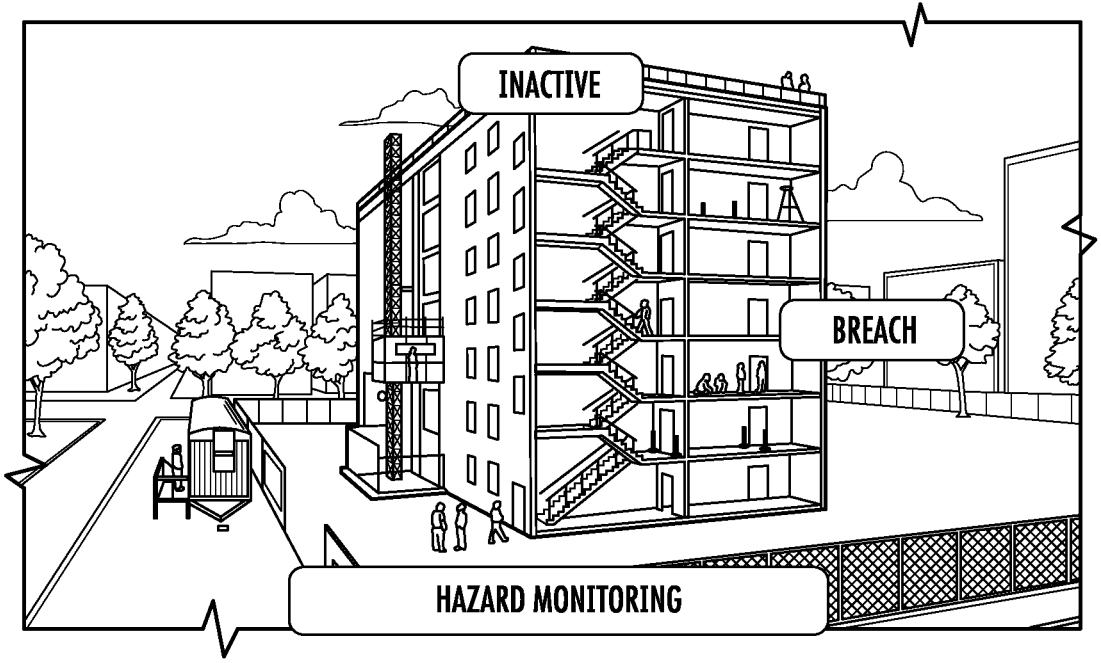
Figure 108:
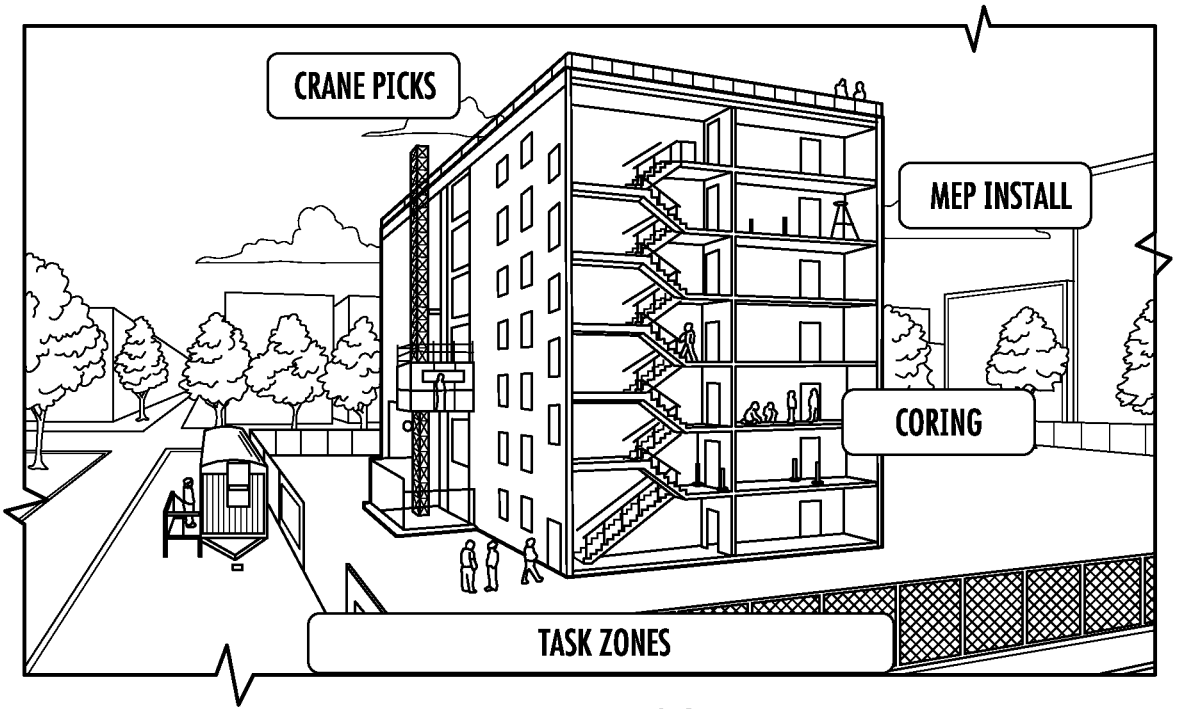
Figure 109:
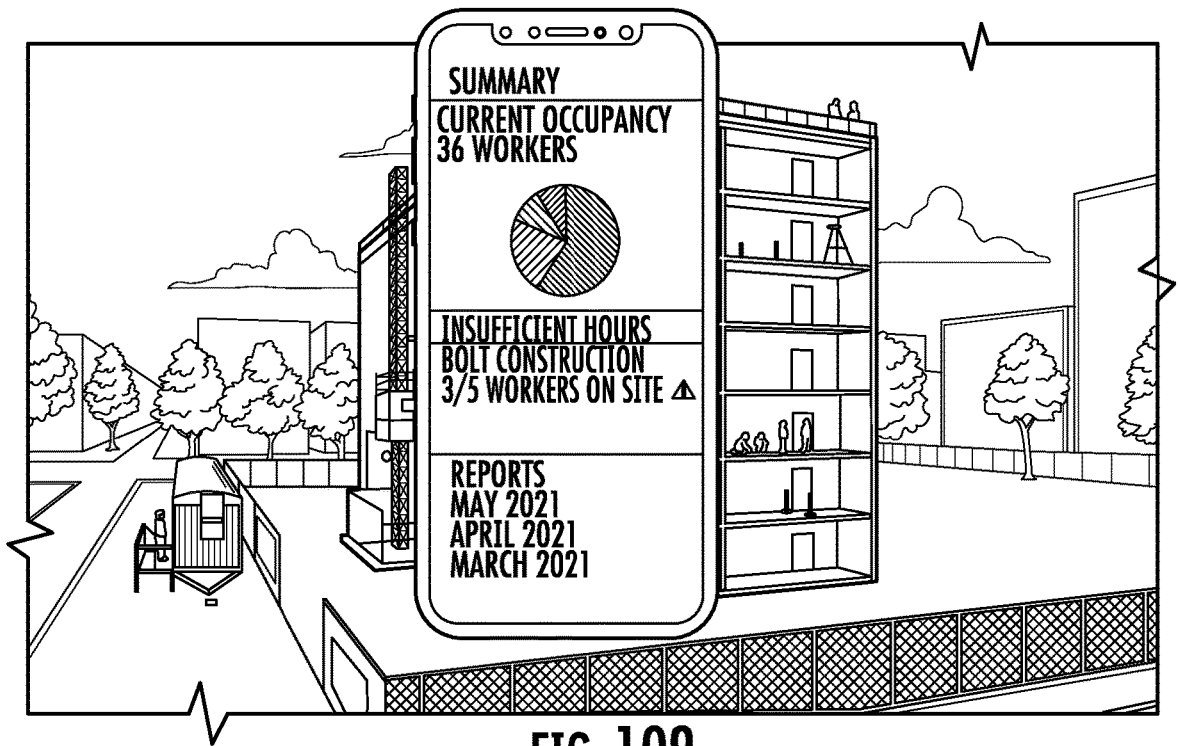
Figure 110:
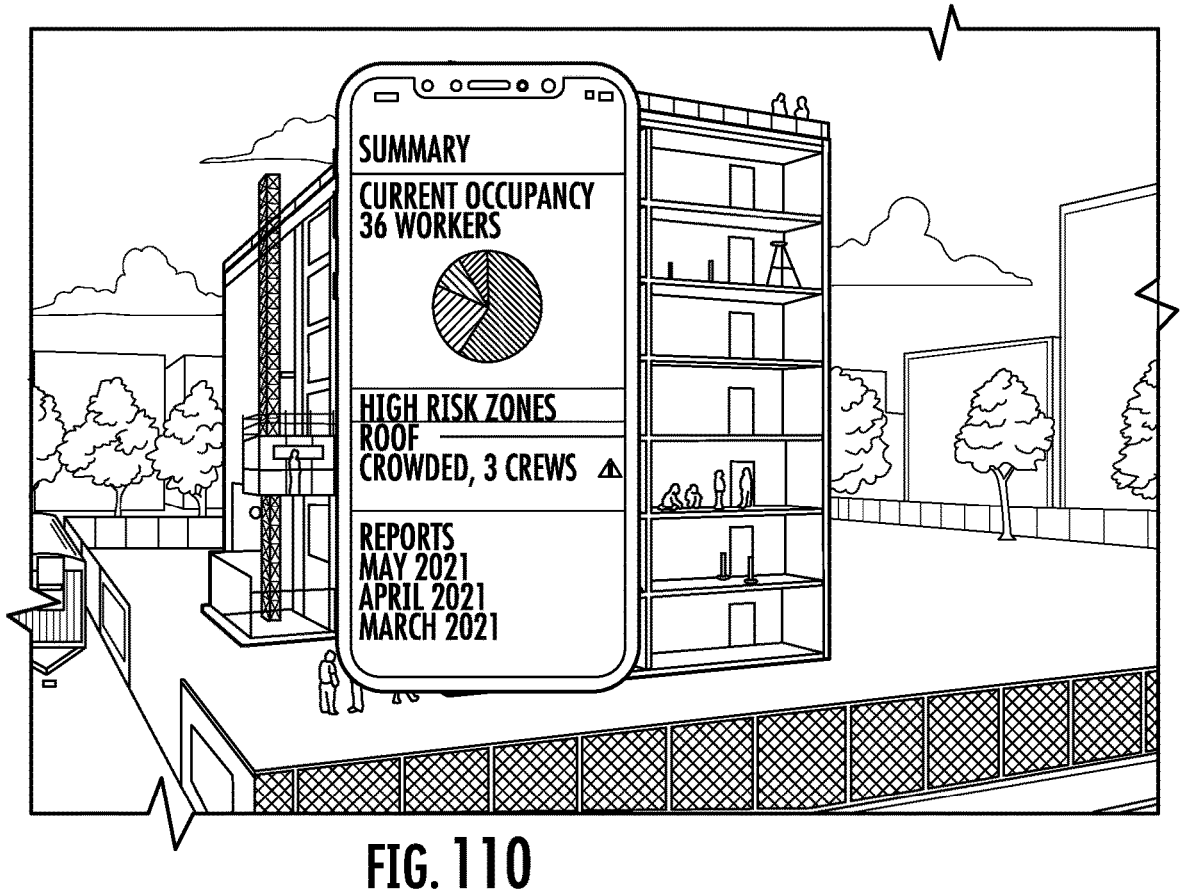
Figure 111:
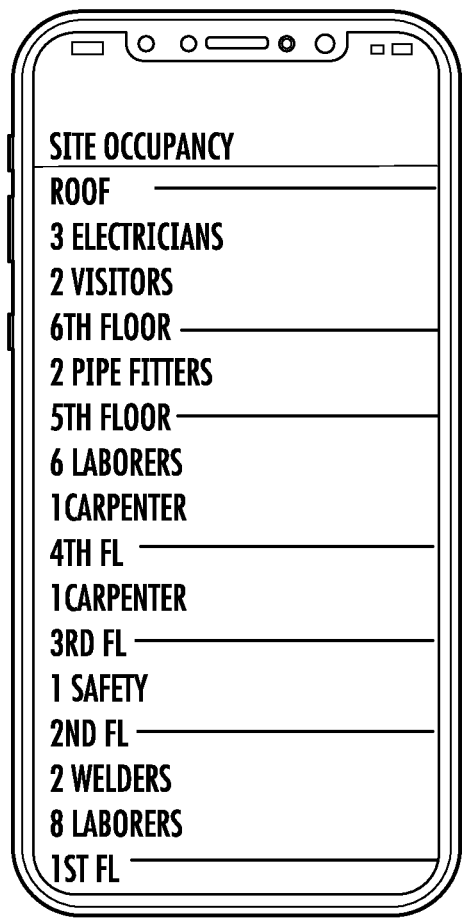
Figure 112:
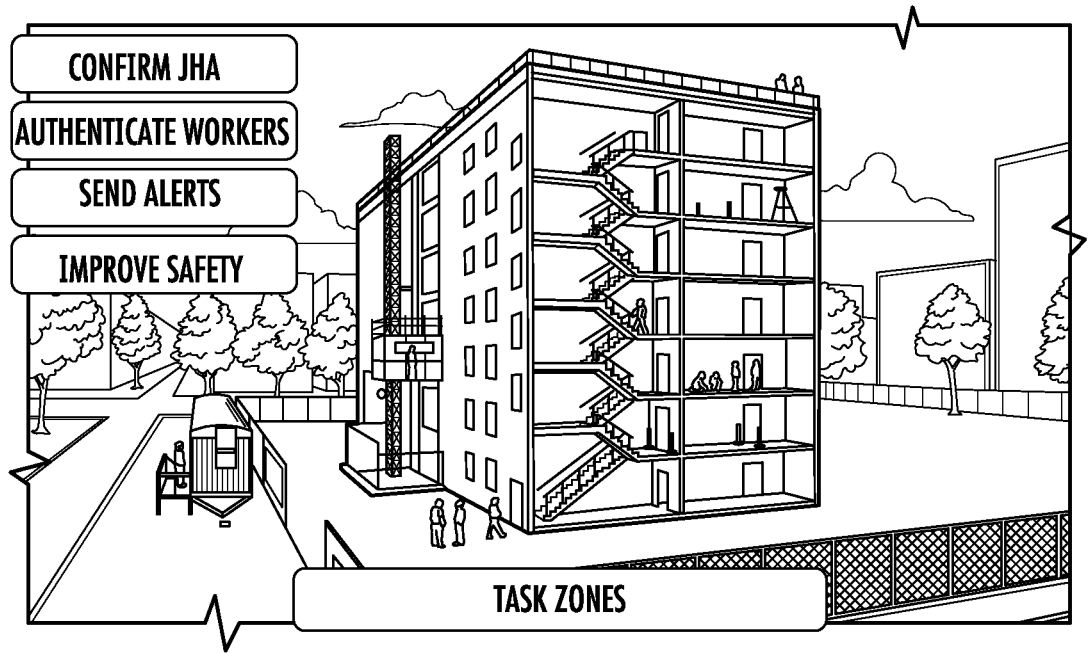
Figure 113:
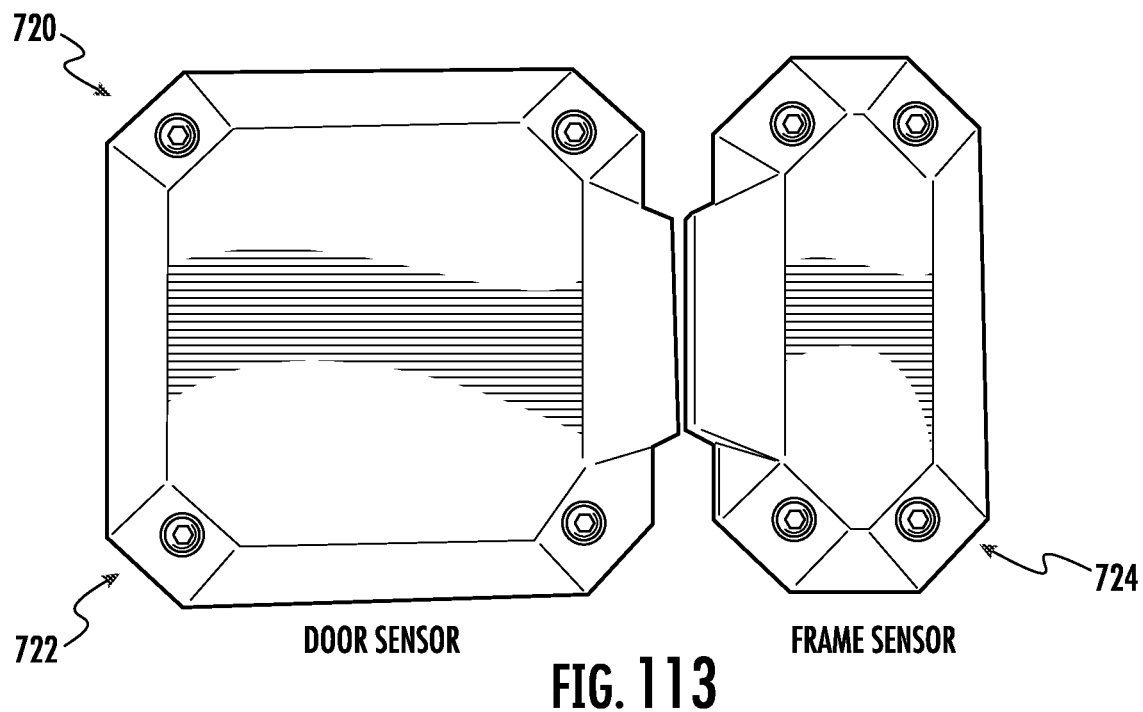
Figure 114:
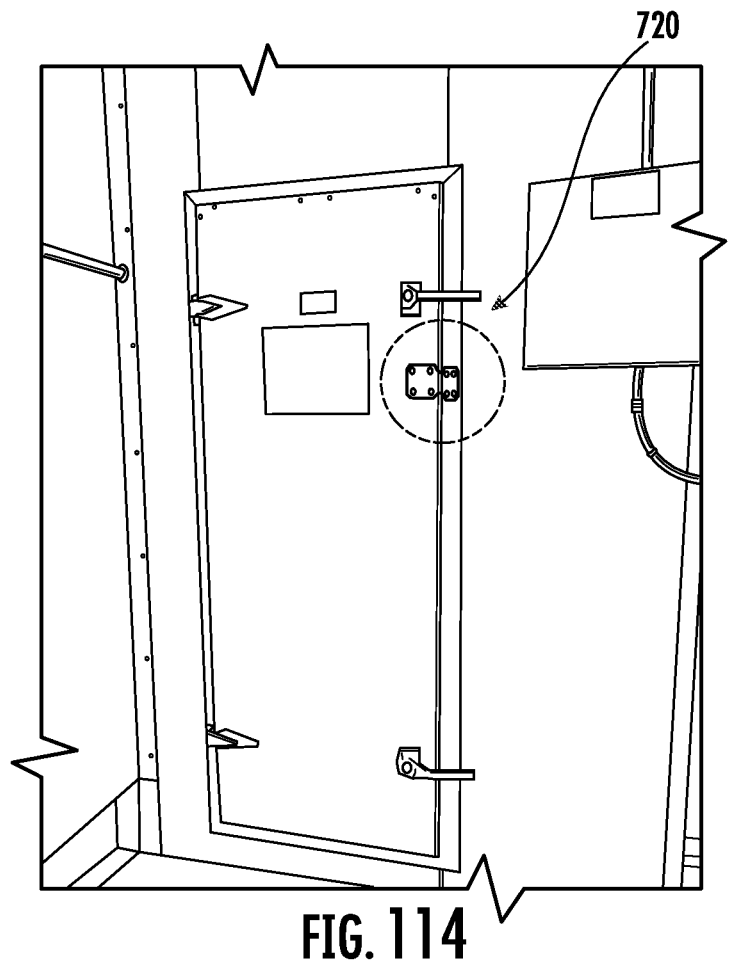
Figure 115:
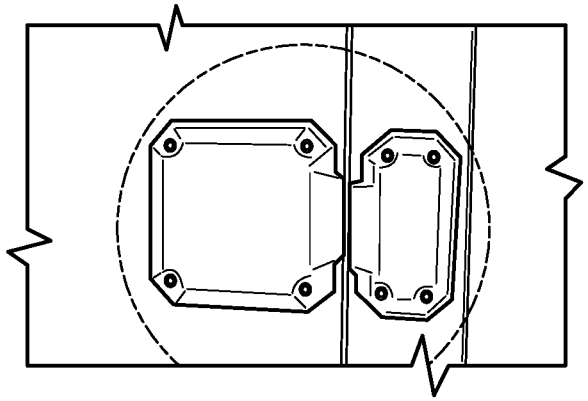
Figure 116:
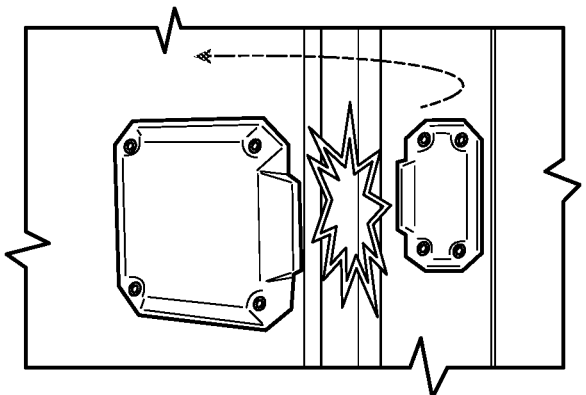
Figure 117:
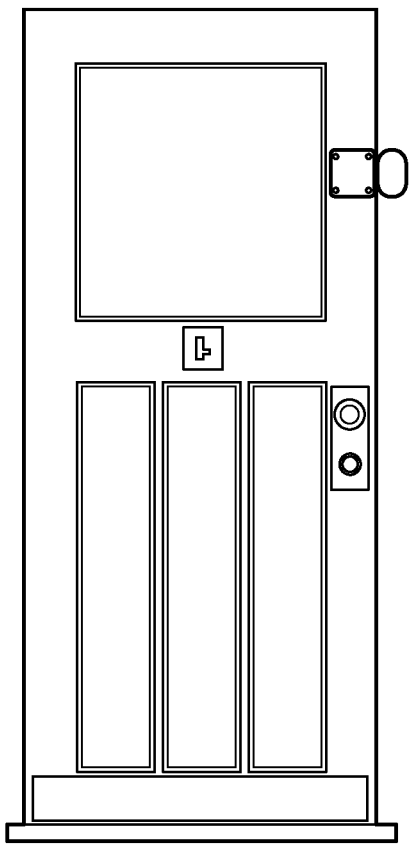

Referring to FIGS. 103-104, in various embodiments the smart zone system 610 is placed near an area where work is being performed. For example, working area 640 is above safety area 642 where the danger exists, such as from falling objects. Referring to FIG. 104, the smart zone may include a gate with a monitoring stand that identifies a person approaching the gate and determines whether the person is authorized to enter the safety area 642.

Referring to FIGS. 105-112, whole site occupancy monitoring enables the system to know how many worker are on site, the location of one or more of the workers (e.g., what floor, what location on a given floor, outside the building, in a trailer), and the trade of one of more of the workers. This can improve emergency responses (e.g., evacuations), controlling access to floors, coordinating work between different workers, and confirming attendance. In various embodiments, workers wear tags, such as smart tags, that include information identifying the trade and/or company information for the worker.

With hazard monitoring, the system can provide real time monitoring of various locations and provide real-time alerts (e.g., Clear, Breach, Inactive). With task zones, such as subcontractor task zones, the system can confirm that only appropriate people are in the respective task zones (e.g., at a task zone for MEP install, at a task zone below a coring, such as a floor coring), the system can also authenticate workers, send an alert when a breach is detected, notify a person such as a general contractor of changes in zone status for protected areas (e.g., Active, Inactive, Clear, Hazard/Crowded).

In various embodiments, the task zone is created by importing jobsite hazard analysis (JHA) data into one or more monitoring devices, thereby assigning the monitoring device(s) to the worker in that zone. The monitoring devices are then configured at or around the safety zone to be protected. After the zone has been setup properly, a signal may be sent, such as to the general contractor. In various embodiments, settings and permissions for a safety zone can be changed dynamically (e.g., during the lifetime of the safety zone).

In various embodiments the system provides a safety report, such as to a personal electronic device (e.g., cell phone). In addition to the safety issues otherwise described, the safety report may identify if there are insufficient people (e.g., only three workers onsite when five workers were expected). The safety report may also indicate if a zone is high risk (e.g., if three crews are in a single zone).

Referring to FIGS. 113-132, various aspects of a keep out zone system 710 that includes occupancy and safety area monitoring are shown. One of the benefits provided by the keep out zone system described herein is that the system constantly monitors various aspects of the worksite, such as doors that should be closed.

Referring to FIGS. 113-117, in various embodiments the keep out zone system 710 includes entranceway monitoring, such as door monitor. In a specific embodiment, a door monitor 720 includes two devices that interface with each other. The first device 722 is coupled to a moveable object, such as a door, and the second device 724 is coupled to a fixed object, such as a frame of the door. When the door is opened the devices detect that the devices have moved relative each other and/or that the distance between the devices has changed (e.g., increased). In various embodiments the devices detect movement via magnetic current, NFC, RFID, and/or wireless, such as radio frequency.

In various embodiments, when one or more of the devices detects that the door has been opened and/or moved, the one or more devices send an alert. In various embodiments, the alert is sent to a single person, such as a person in charge of the area behind the door and/or a person performing work behind the door. In various embodiments, the alarm is sent to multiple recipients, such as two or more stakeholder(s) monitoring the hazard.

Figure 118:
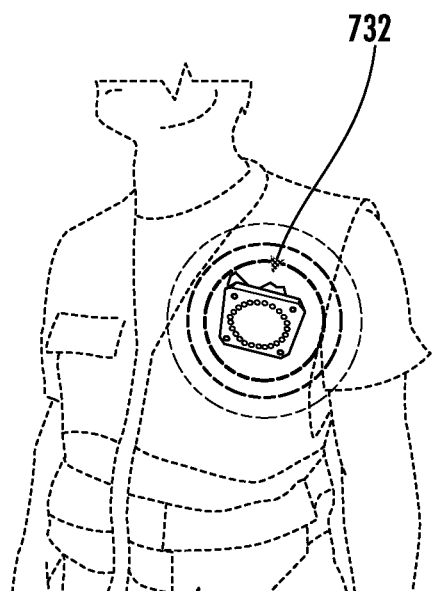
Figure 119:
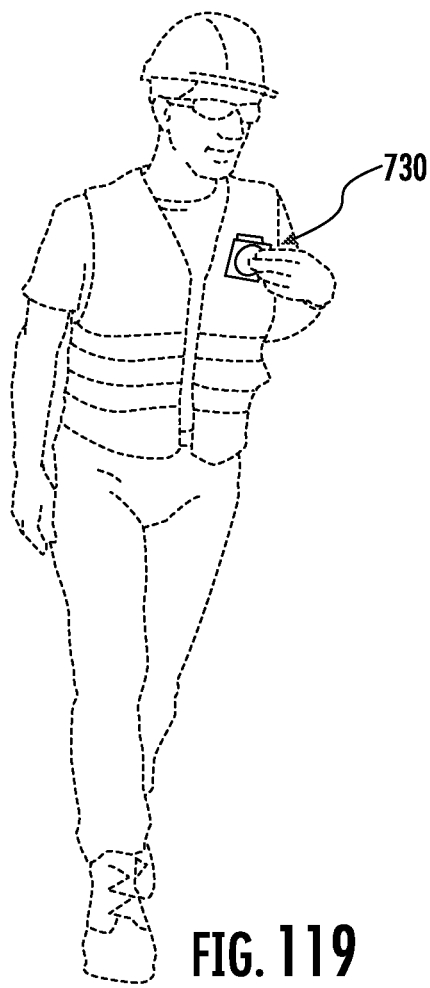
Figure 120:
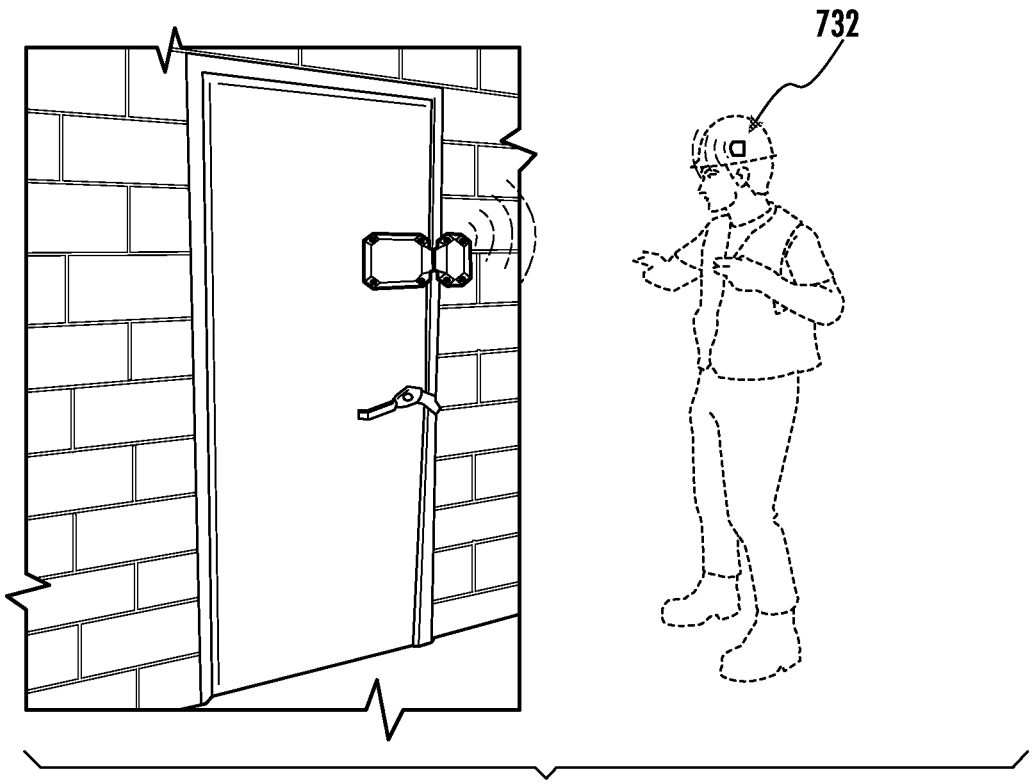

Referring to FIGS. 118-120, in various embodiments the keep out zone system authenticates certain workers and allows authenticated workers to open the door without triggering an alarm. In various embodiments the identity and/or access rights of the person are determined by interacting with an electronic device the person is carrying. For example, a certain class of workers (e.g., electricians) may be permitted to open the door, and if an electrician approaches the door the keep zone system identifies the person, determines whether the person is authorized to open the door, and does not trigger an alarm in response to the door being opened when the keep out zone system determines the person is authorized to enter the area. In various embodiments the person authorized to open the door is carrying electronic device 730 that identifies that person as having sufficient authorization, and the person not authorized to open the door is carrying electronic device 732 that identifies that person as not having sufficient authorization.

Figure 121:
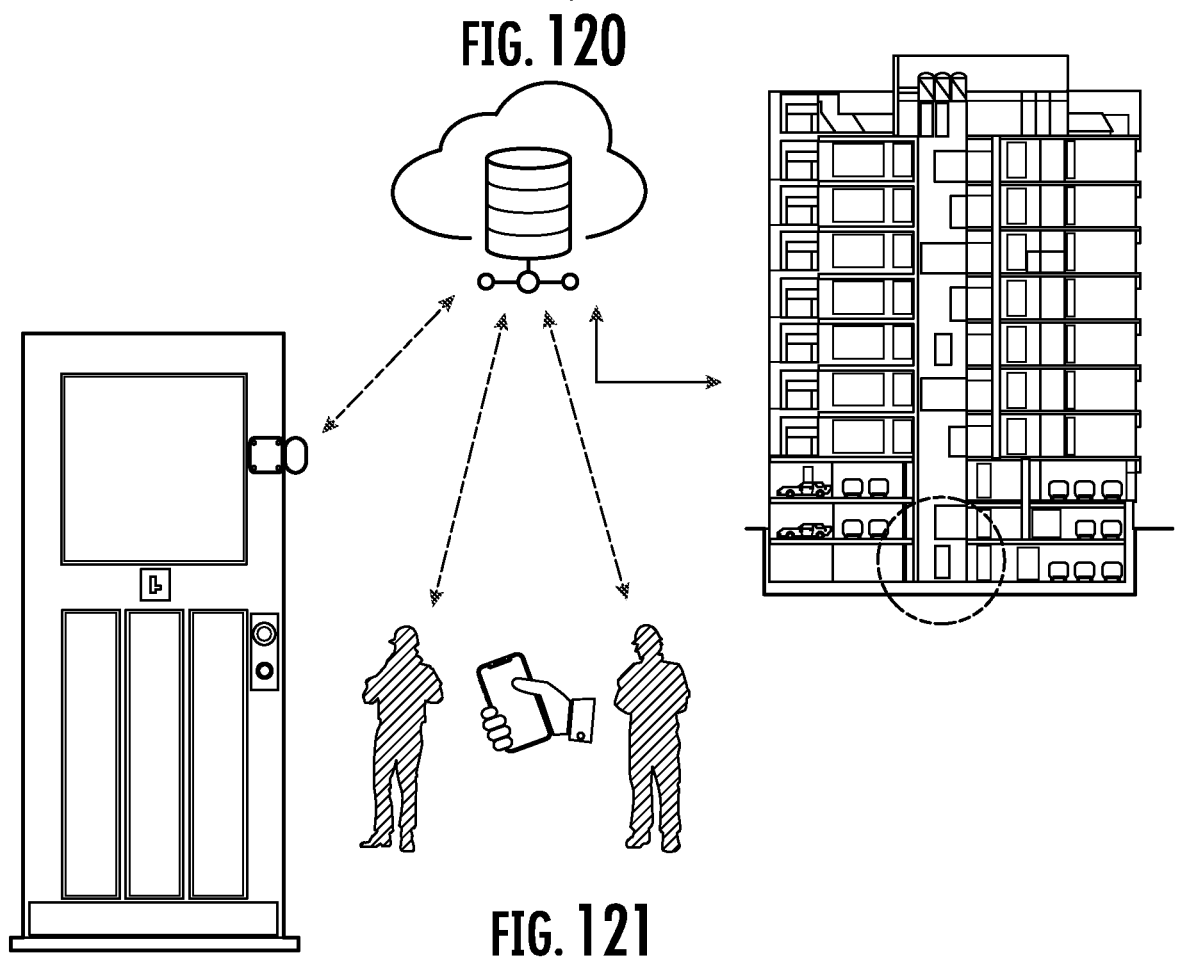

Referring to FIG. 121, in various embodiments the keep out zone system sends alerts to a central server, which forwards the alerts to stakeholders (e.g., such as to an electronic mobile device, such as a cell phone).

Figure 122:
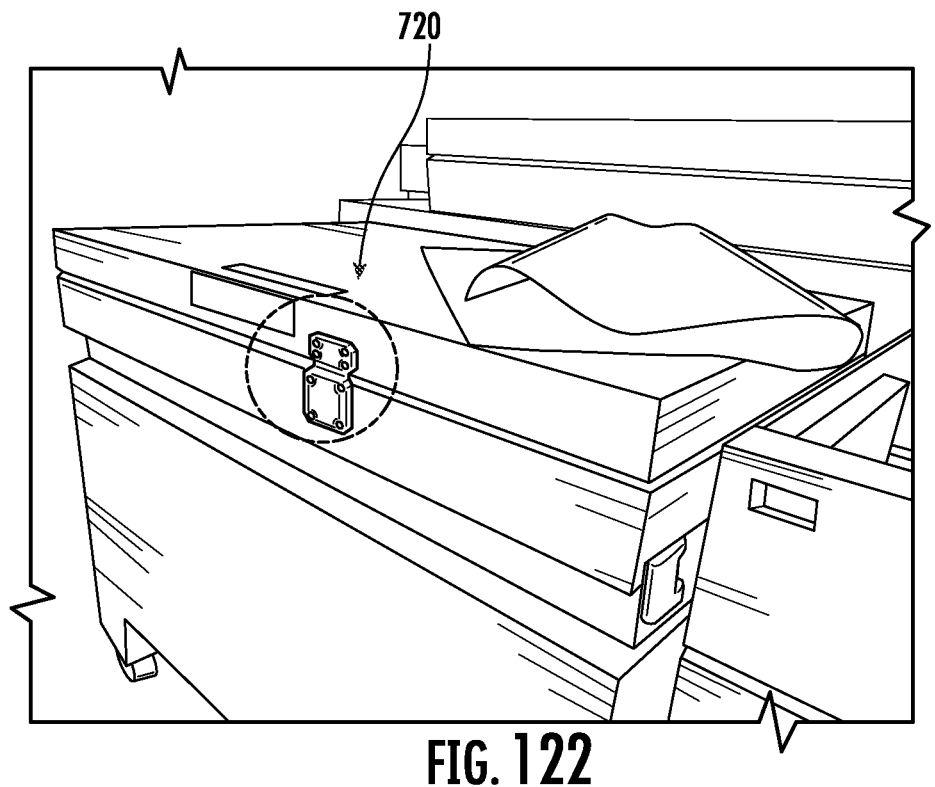
Figure 123:
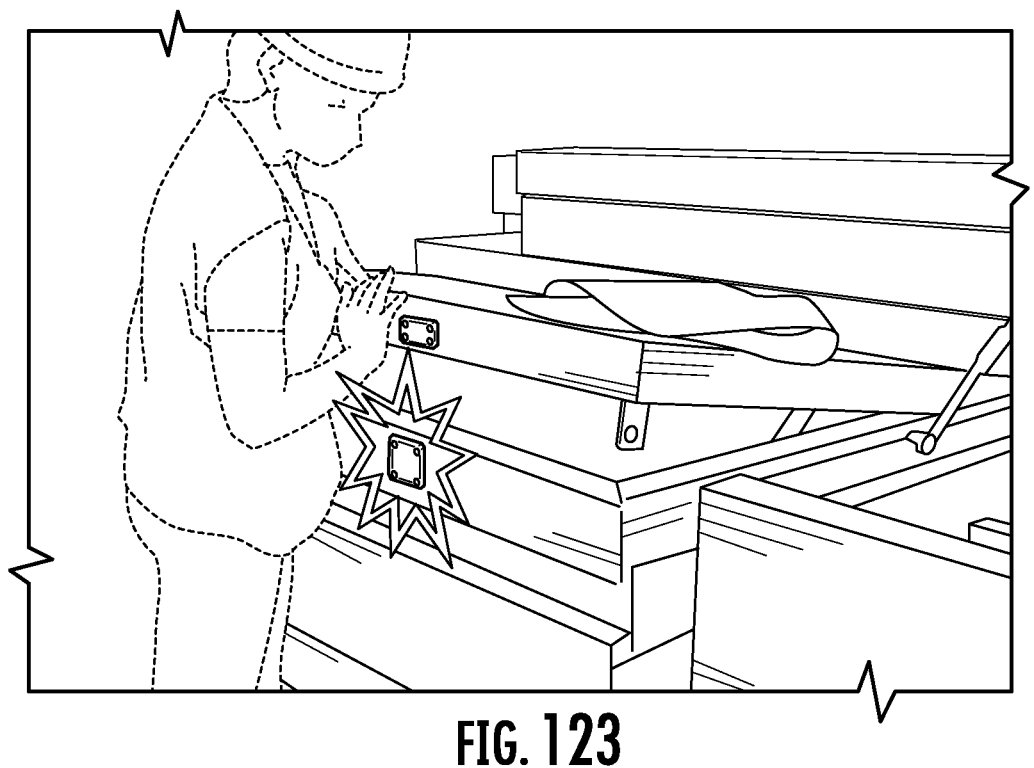

Referring to FIGS. 122-123, in various embodiments an access monitoring system can be applied to objects. For example, an access monitoring system 740 similar to the door monitor 720 described above can be applied to a box. When the box is opened an alarm is triggered, such as if the box is opened and there is not a person nearby that is authorized to open the box (e.g., because an unauthorized person opened the box). For example, the access monitoring system 740 includes one or more accelerometers to detect movement.

Figure 124:
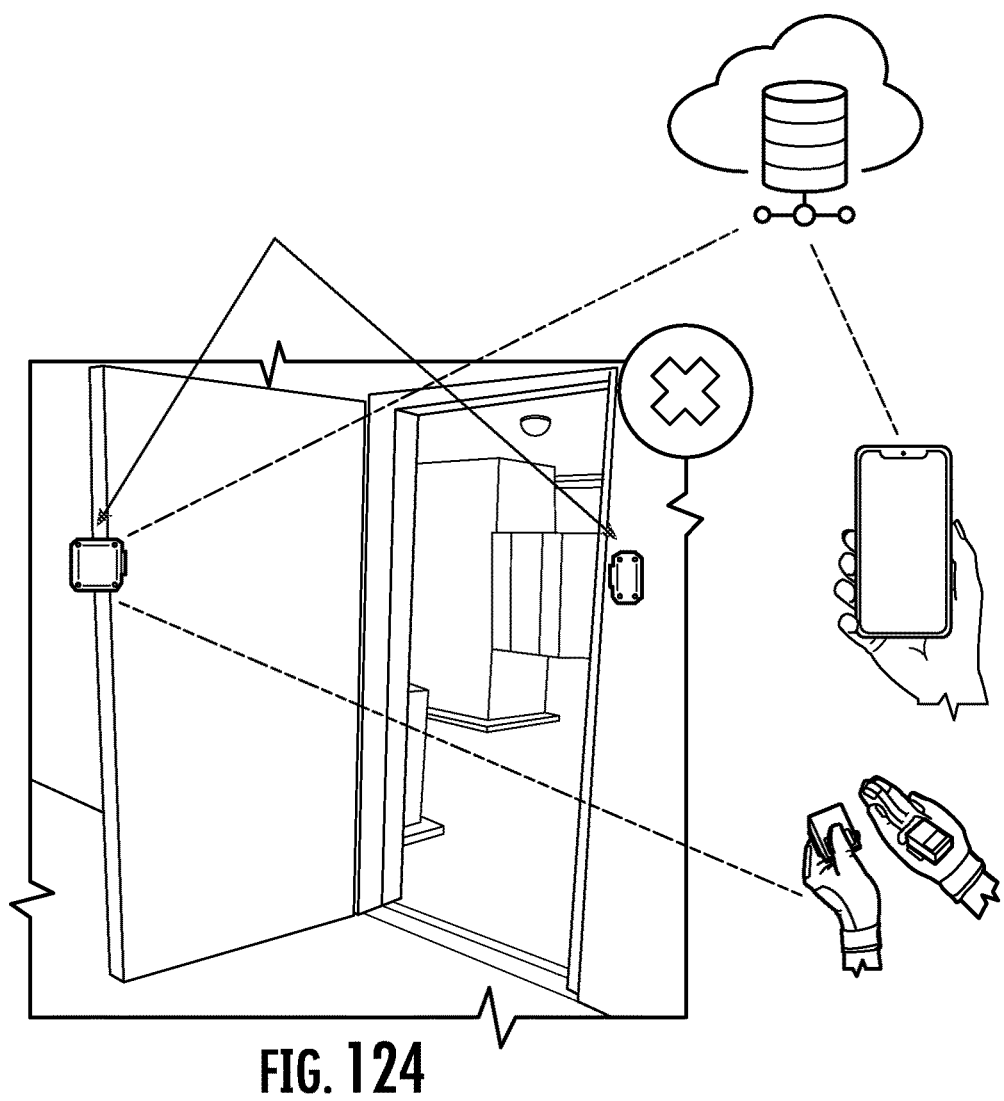
Figure 125:
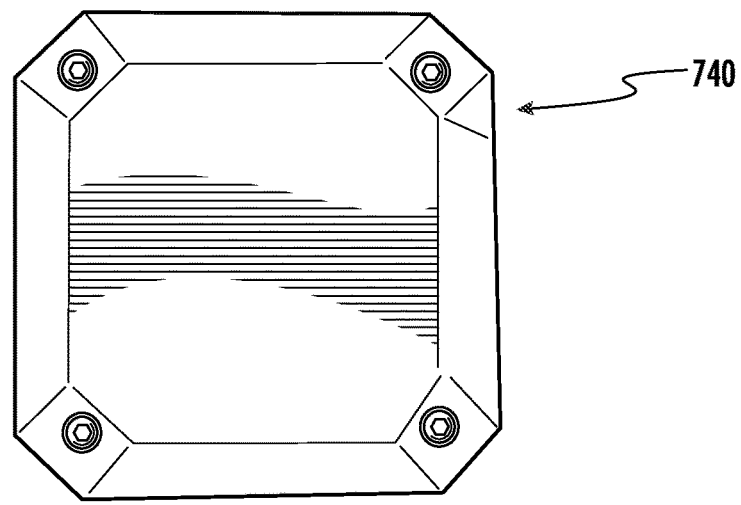
Figure 129:
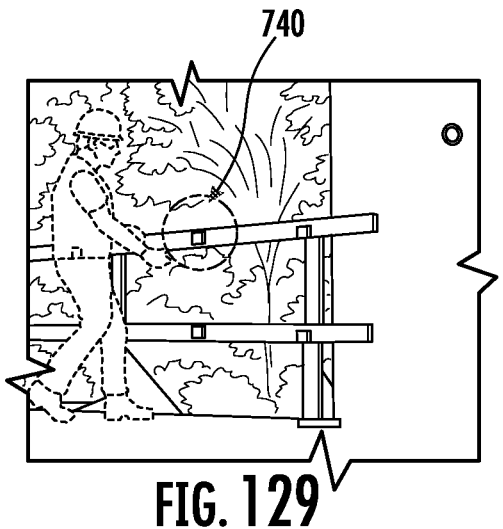
Figure 130:
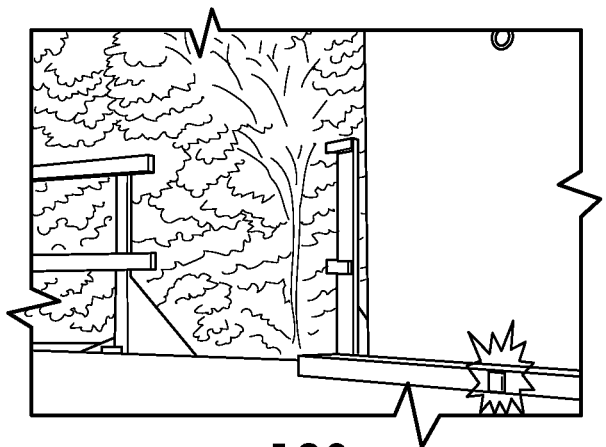

Referring to FIG. 124, in various embodiments when a door is opened, the keep out zone system first determines whether an authorized person is nearby. If not, an alarm is triggered.

In various embodiments, an alarm is triggered by the keep out zone system after a predetermined area of time. For example, the keep out zone system triggers an alarm if the door being monitored has been left open for 6 minutes or longer.

Referring to FIGS. 126-130, in various embodiments the devices described in this keep out zone system could be applied to barriers. For example, the devices could be coupled to a board covering a hole, and/or a guard rail blocking people from a dangerous fall.

Figure 131:
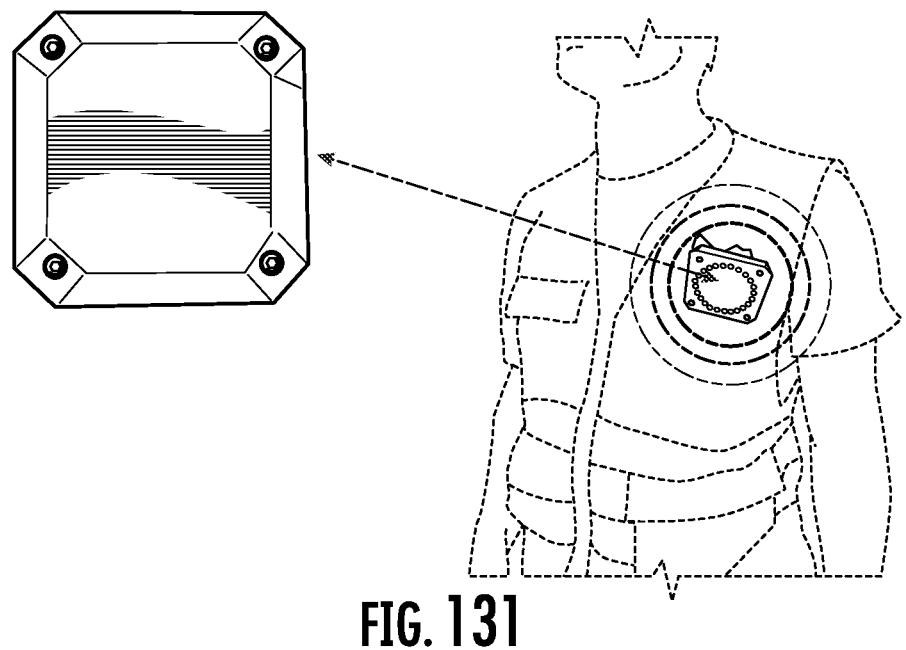
Figure 132:
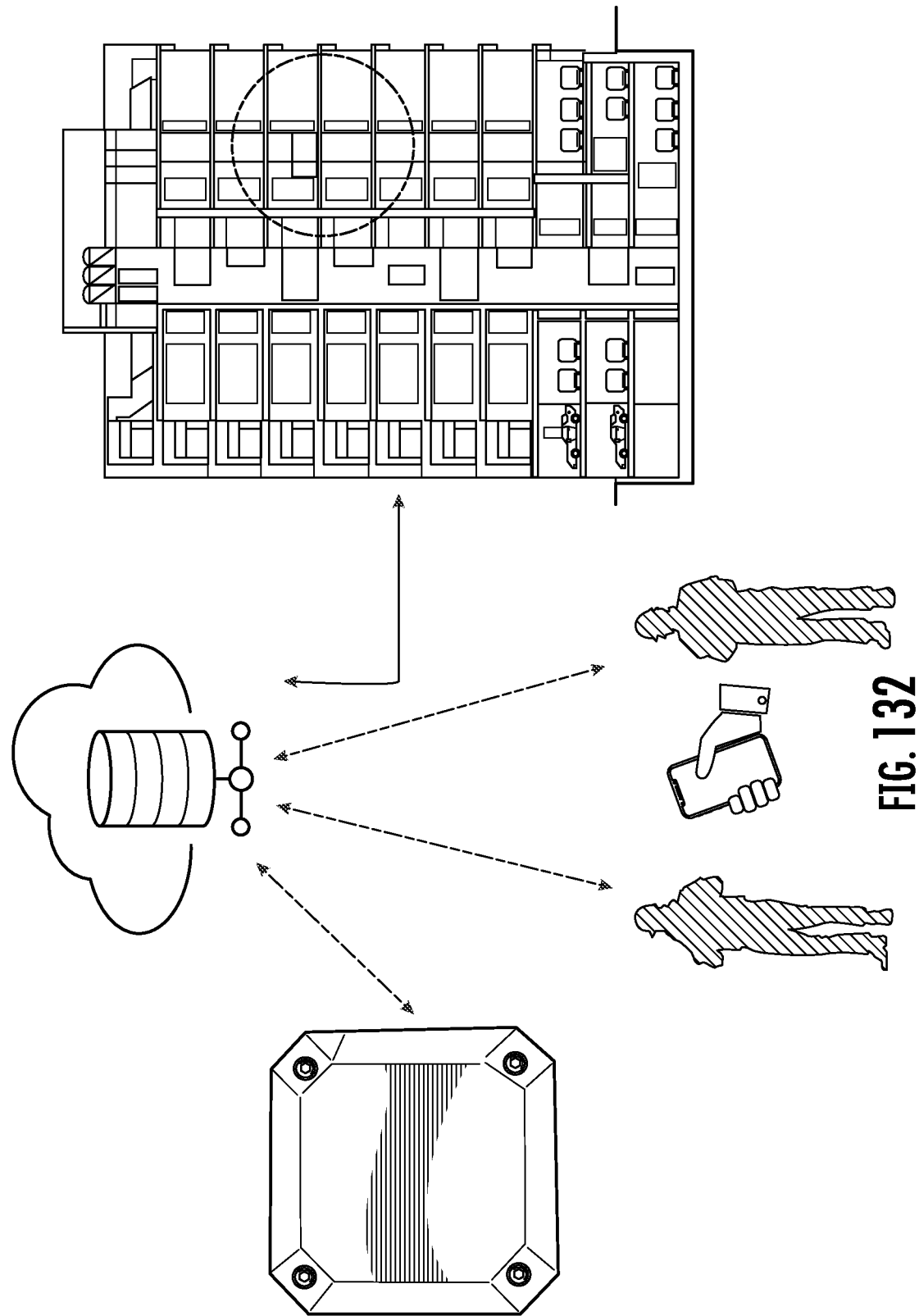
Figure 133:
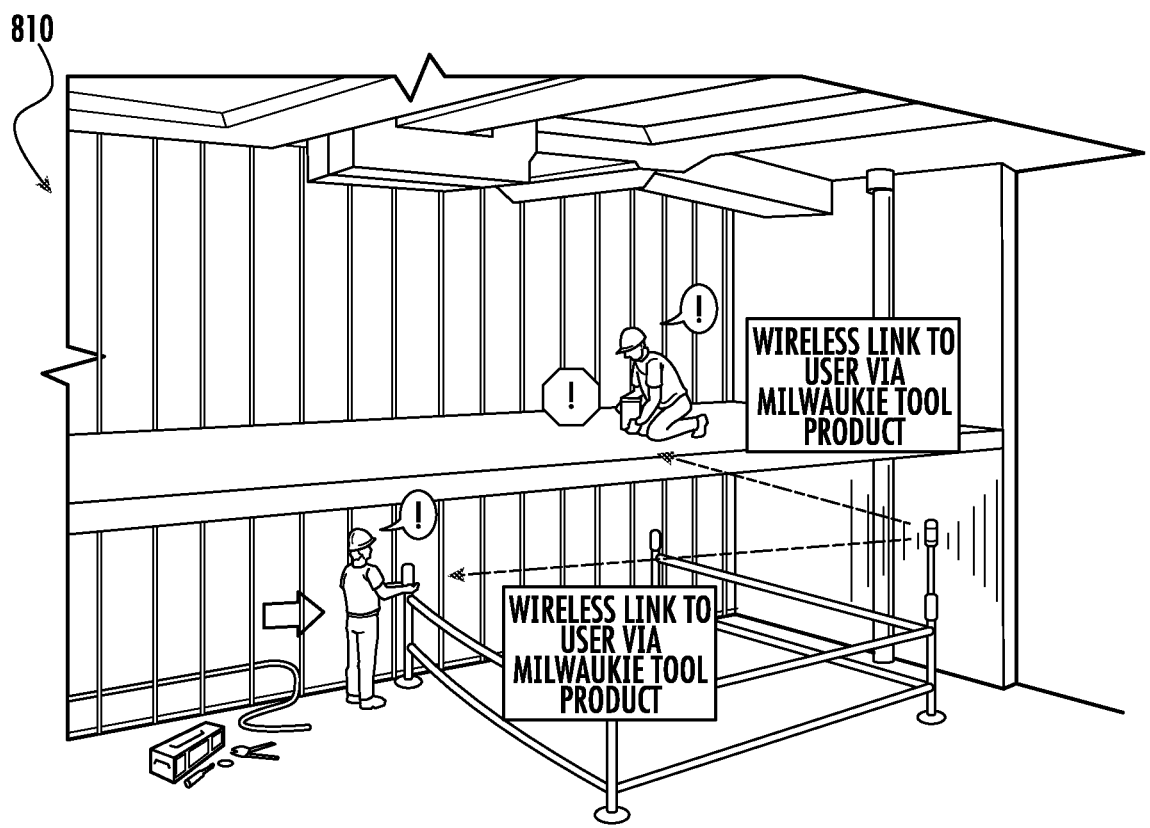
Figure 136:
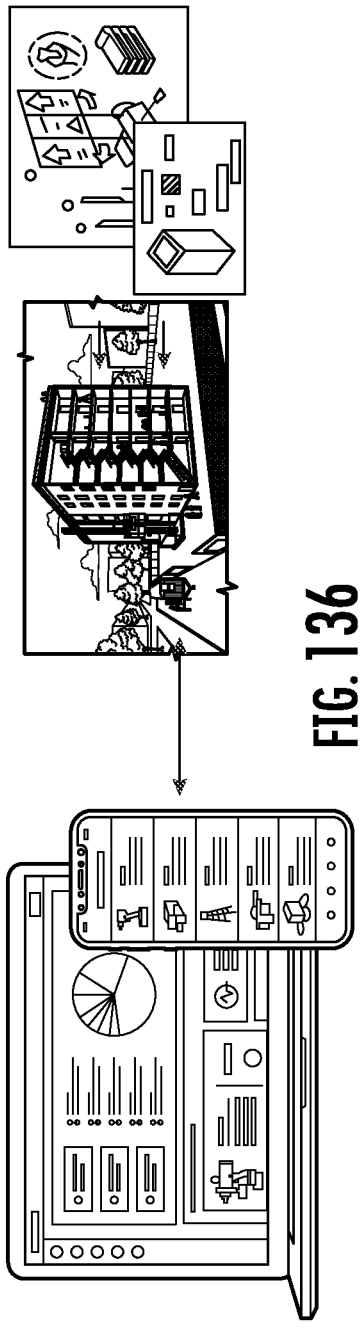

Referring to FIGS. 131-132, alerts may be sent to one or more recipients. Referring to FIG. 131, in one configuration an alert may be sent to a single person, such as the unauthorized person opening the door and/or removing the guard rail. Referring to FIG. 132, in another configuration the alert may be sent to multiple recipients (e.g., the person opening the door, a safety compliance person, and/or a central database for logging).

Referring to FIGS. 133-137, various methods of a keep out zone system 810 providing notifications and tracking the jobsite are shown. In various embodiments alerts and/or notifications are transmitted, such as wirelessly transmitted, to devices such as wearable devices 820, lighting devices, such as site lighting 830, and/or tools.

Referring to FIGS. 134-135, lighting devices, such as room lighting and/or headlamps, can be used to indicate status of the job site (e.g., before work has started, work is about to start, work has started and imminent danger is possible). For example, the lighting may flash if someone approaches the safety zone, generate sounds such as beeps as a warning, and/or both.

Referring to FIG. 135, tools may exhibit various alerts/notifications, such as haptic features, if someone is near or in the safety zone, such as a light flashing if a user approaches a safety zone, a delay on the tool trigger activating the device, the tool vibrating, and/or the tool being disabled.

In various embodiments the keep out zone system includes a range of alert capabilities, from simple warnings to full alerts. The level of the warning/alert selected may be configured by the person in charge of the safety area based on features such as how dangerous the area is, whether work is actively being performed in the area, the authorization level of the person entering the area, etc. At a lowest warning level, the system triggers a light on a tool or personal device (e.g., a headlamp). At a higher warning level the system triggers a delay on operating the tool and/or the tool moves to indicate the warning (such as via the tool shaking). At a higher warning level, the tool is disabled from working. At a higher warning level, a device is enabled to flash a light and/or emit a sound, such as a headlamp flashing and/or beeping. At a higher warning level of full alert an area-wide device, such as a flood light, flashes and/or beeps to signify to everyone in the area that a dangerous condition exists.

In various embodiments, the smart safety zone systems include tracking capabilities. For example, the smart safety zone system is configured to track workers, safety zones, and/or tools. Further, the smart safety zone system is configured to adjust the configuration of safety zones. For example, the smart safety zone system may be configured to receive a command from a user (e.g., from a handheld electronic device) that initiates alerts, such as a sign indicating that people near the safety zone should look up.

In various embodiments, the keep out zone system generates and delivers a report that provides information such as a floor where a safety zone is set up, the time a safety zone was set up or taken down, the person or people responsible for the safety zone, a hazard or task associated with the safety zone, and/or how many warning or infractions were generated with respect to the safety zone (e.g., such as over the course of the day). In various embodiments one or more benefits of these reports include expediting or enhancing period site walks (e.g., end of the day site walks) for safety and/or management of the worksite, confirming that safety controls were used correctly while hazardous work was being performed, confirming that the area is not still hazardous after the work has stopped (thereby allowing workers to start working in the safety area again after the safety area is no longer dangerous), and/or improving worker awareness and follow trends for future hazards/safety zones.

Figure 137:
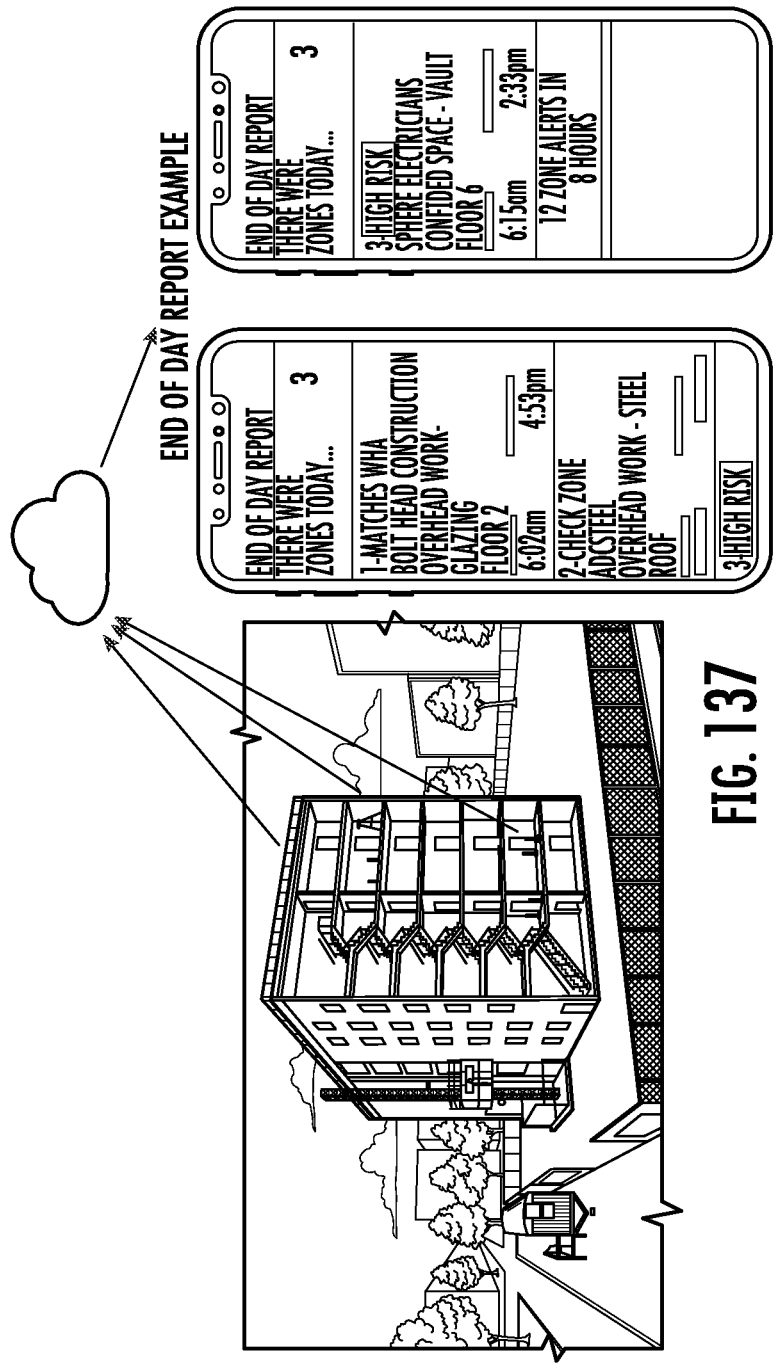

Referring to FIG. 137, in various embodiments the smart safety zone system generates reports, such as daily reports, based on stored information relating to the safety zone, workers, tools and/or equipment being monitored.

Referring to FIGS. 138-142, various aspects of a safety monitoring system 910 are shown. In various embodiments environmental conditions, such as temperature and/or humidity, are monitored. For example, a plurality of monitors are distributed around a worksite that monitor temperature and/or humidity. In some situations the monitors communicate the data to a central location, such as a server, and/or the monitors analyze the data and optionally initiate an alarm based on that analysis (e.g., if the temperature and/or humidity are too high).

In various embodiments of a safety monitoring system, the locations and/or count of people is monitored. This information can be used to provide a safer worksite.

For example, one exemplary method of monitoring a safety zone at a construction site includes receiving a first signal indicating a first number of people in a protected area on a construction site, receiving a second signal indicating the occurrence of an emergency event that corresponds to the protected area, receiving a third signal indicating a second number of the people that were in the protected area (e.g., counting workers that are currently outside the protected area but were previously in the protected area, such as by being one of the first number of people), and determining whether the protected area is evacuated by comparing the first number to the second number. For example, the safety monitoring system 910 includes devices that monitor entrances and exits to protected areas to monitor how many workers are present. Upon receiving a signal indicating the occurrence of an emergency event (e.g., a fire alarm is pulled), evacuated workers are counted. For example, counting the second number of the people that were in the evacuated may involve a personal electronic device (e.g., cell phone of a supervisor) scanning ID devices (e.g., personal devices 80) of each of the second number of the people.

As background, heat stroke, heat exhaustion, and dehydration can all be risks for workers on a jobsite, such as a construction jobsite. Various embodiments of the safety monitoring system 910 provide the ability for a foreman and/or safety personnel to receive remote notifications to protect workers (e.g., change worker location, alter the schedule, provide better airflow in one or more areas). In various embodiments, safety monitoring system 910 includes one or more sensors installed at locations of transit (e.g., stairwells, lift hoists) to identify which workers on are each floor and/or are in each area. Further, one or more sensors of safety monitoring system 910 monitor conditions, such as atmospheric conditions for the one or more floors and/or areas. In various embodiments, safety monitoring system 910 includes one or more thresholds, and safety monitoring system 910 is configured to generate an alarm if one or more conditions exceeds and/or equals the one or more thresholds. For example, safety monitoring system 910 includes a threshold for an atmospheric condition. After receiving data that measures the atmospheric condition, the safety monitoring system 910 compares the measured data to the threshold. Based on the results of that comparison, the safety monitoring system 910 determines whether to generate an alarm. As another example, if the temperature and/or humidity is above a threshold level (e.g., 90 degrees Fahrenheit, 90% humidity) then an alarm is generated, and the alarm is communicated to the worker in the area, a foreman in charge of the area, and/or a safety monitor individual.

Stated another way, in various embodiments a safety monitoring system 910 includes a first monitoring device 940 and a central server 990. The first monitoring device is configured to measure an atmospheric condition, to monitor the presence of a worker within a protected area on a construction site, and to generate a notification indicating the measurement of the atmospheric condition and the presence of the worker. The central server is configured to receive the notification from the first monitoring device, analyze the notification, and transmit an alarm to the worker in response to the analyzing of the notification. In various embodiments, the central server is configured to generate a second alarm to a second worker in response to analyzing the notification and in response to receiving data that the second worker is in the protected area.

In various embodiments, the notification indicating a measurement of the atmospheric condition and the presence of the worker includes a first signal indicating the measurement of the atmospheric condition and a second signal indicating the presence of the worker. In various other embodiments, the notification indicating a measurement of the atmospheric condition and the presence of the worker includes a single signal indicating both the measurement of the atmospheric condition and the presence of the worker.

Figure 138:
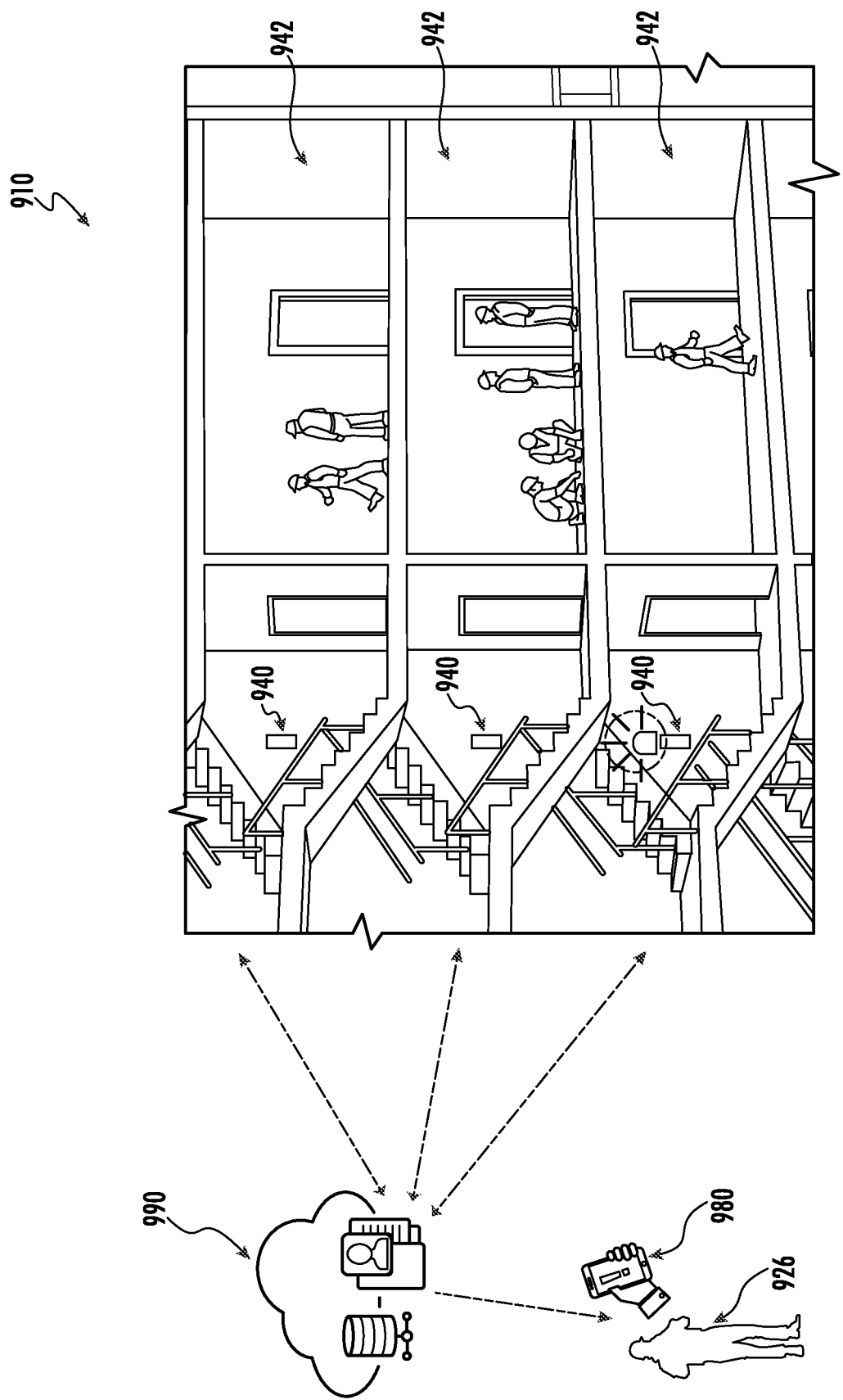

Referring to FIG. 138, in various embodiments safety monitoring system 910 includes one or more electronic monitoring devices 940. The electronic monitoring devices 940 monitor various conditions, such as atmospheric conditions (e.g., temperature, humidity). The electronic monitoring devices 940 communicate signals to central server 990, which stores the data in a database and/or communicates the data to personal device 980 of a safety monitor individual 926 responsible for monitoring safety conditions of the worksite.

Figure 139:
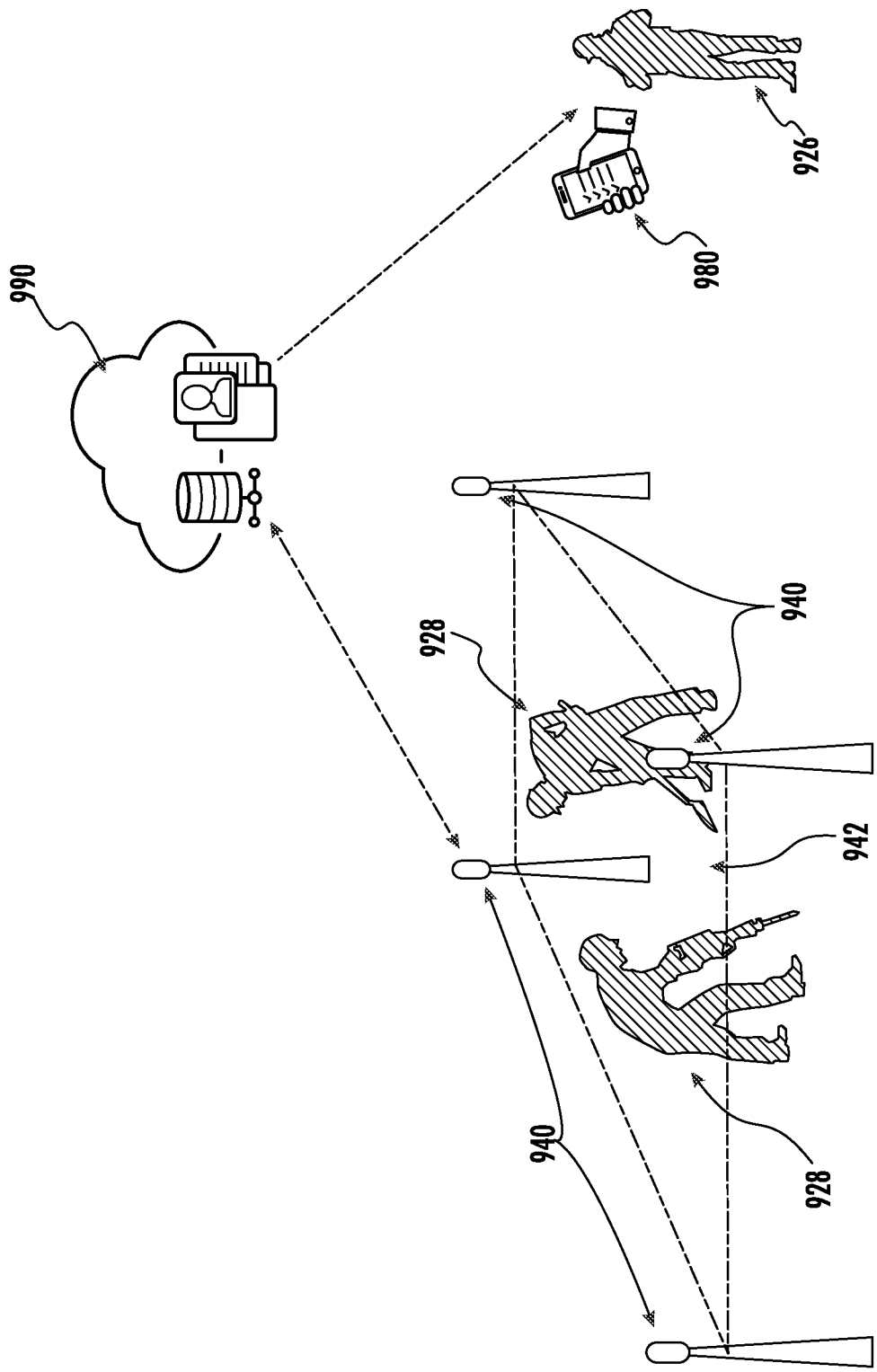

Referring to FIG. 139, in various embodiments safety monitoring system 910 includes one or more electronic monitoring devices 940 arranged around a protected area 942, such as around a periphery of the protected area 942. The one or more electronic monitoring devices 940 monitor the presence of workers 928 within the protected area 942 and/or the one or more electronic monitoring devices 940 monitor conditions, such as atmospheric conditions. The one or more electronic monitoring devices 940 generate a signal communicating the data collected to a central server 990, which optionally communicates the data to personal device 980 (e.g., a cellular phone) of a safety monitor individual 926 in charge of monitoring the protected area 942.

In response to detecting an atmospheric condition greater than a threshold (e.g., a high temperature of the ambient air), the safety monitoring system 910 (e.g., the one or more electronic monitoring devices 940) first determines whether there are workers 928 within the protected area 942. In various configurations, safety monitoring system 910 sends an alert to safety monitor individual 926 independent of whether a worker 928 is within the protected area. In various other configurations, safety monitoring system 910 only sends an alert to safety monitor individual 926 if at least one worker 928 is within the protected area 942 having the atmospheric condition greater than the threshold.

Figure 141:
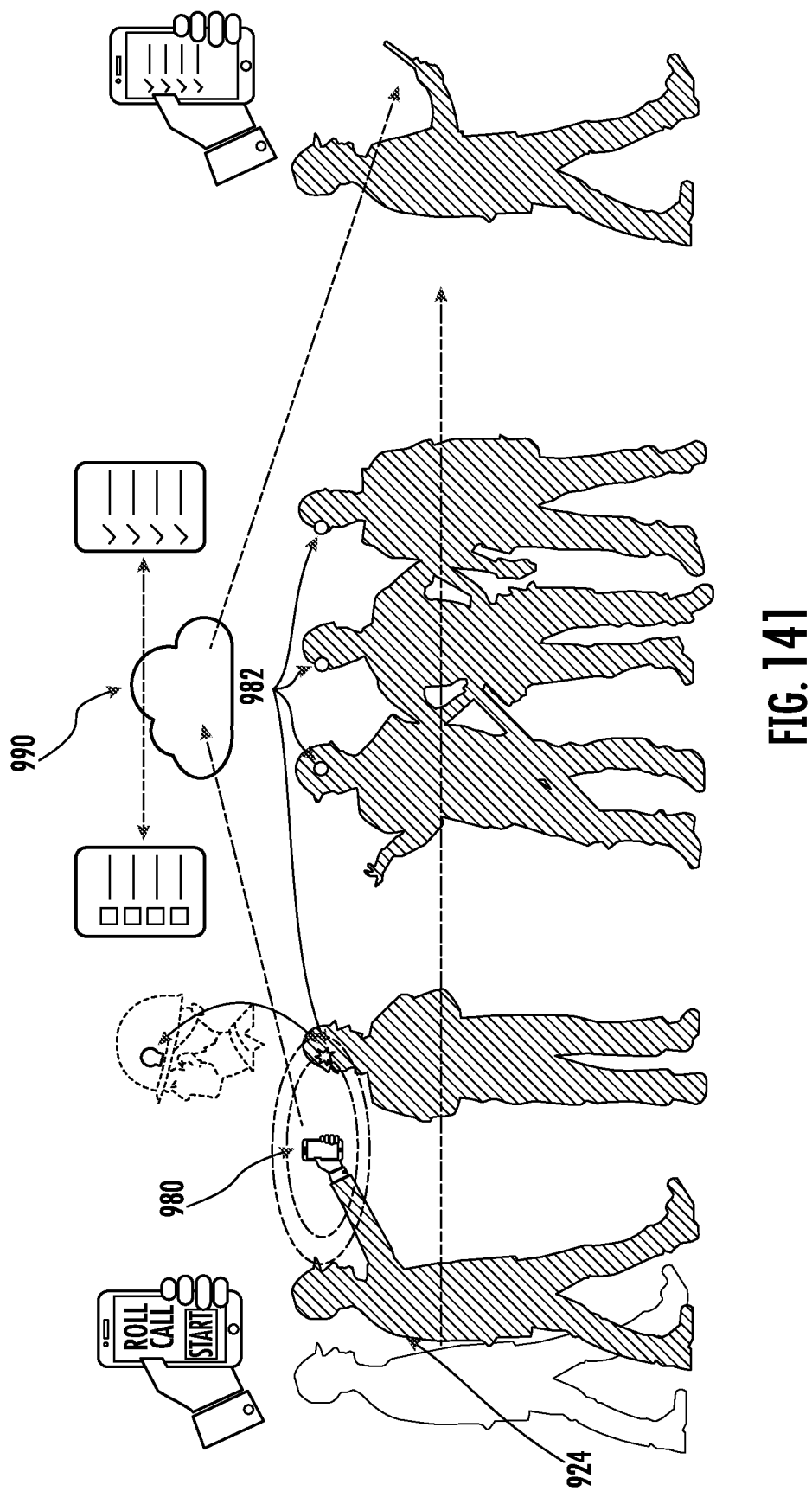
Figure 142:
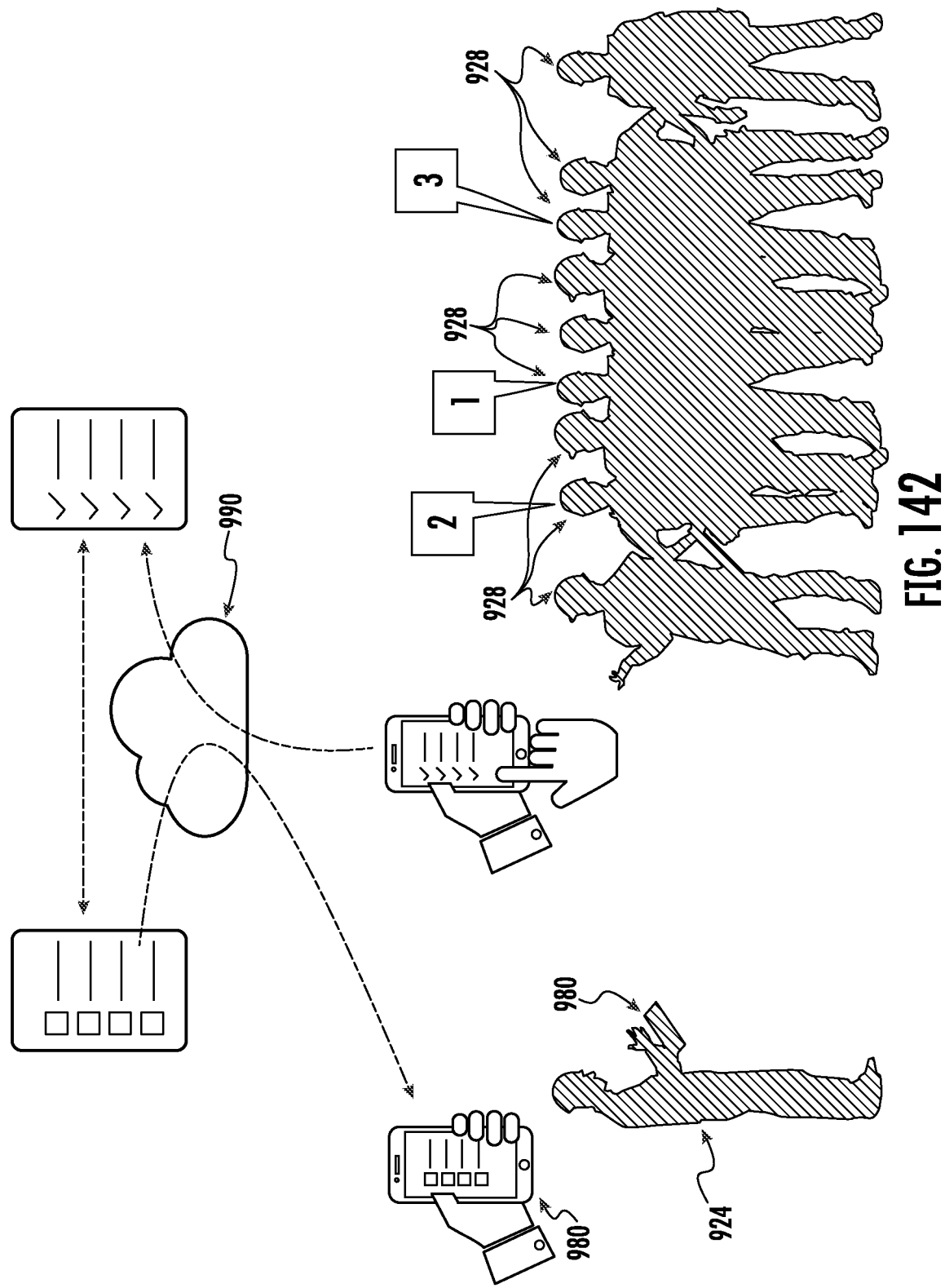

Referring to FIGS. 140-142, in the event of an emergency, the ability of safety monitoring system 910 to provide an accurate count of workers currently onsite can be very helpful to help avoid injury to one of the workers. In various embodiments safety monitoring system 910 is configured to provide a count of workers onsite within seconds of that information being requested, if not sooner (e.g., if the safety monitoring system 910 is constantly communicating the number of workers onsite). Further, safety monitoring system 910 can be configured to communicate the number of workers located in various areas of the worksite (e.g., 3 workers on the third floor, 4 workers on the fourth floor, etc.).

Referring to FIG. 140, in various embodiments safety monitoring system 910 includes one or more electronic monitoring devices 940 to scan the area for workers 928. For example, the one or more electronic monitoring devices 940 read ID devices 982 that identify each worker 928, such as uniquely identifying each worker 928.

Referring to FIG. 141, in various embodiments a personal device 980 (e.g., cell phone) of foreman 924 scans the ID devices 982 to identify workers 928. In this way, the workers 928 present for the rollcall can be quickly counted and identified, thereby facilitating the foreman 924 identifying the workers 928 unaccounted for.

Referring to FIG. 142, in various embodiments a foreman 924 manually enters information identifying workers 928 onsite, such as after reading through a rollcall and entering the identification and/or companies of the workers 928 present. In various embodiments, the one or more electronic monitoring devices 940 include a device that indicates that workers 928 should gather there for rollcall and/or counting (e.g., a flag and/or a light). The one or more electronic monitoring devices 940 communicate data to the central server 990. If an emergency occurs, the data collected at the central server 990 can be used to generate a current list of people onsite and/or an emergency muster station rollcall to confirm that every worker 928 is safe and accounted for.

In various embodiments, safety monitoring system 910 includes a plurality of portable electronic monitoring devices 940 configured to monitor a plurality of protected areas 942 at a construction site. A first monitoring device 940 of the plurality of monitoring devices 940 is configured to monitor the presence of a plurality of workers 928 within a first protected area 942 of the plurality of protected areas 942, and to generate a signal indicating the presence of the workers 928. The central server 990 is configured to receive the signal from the first monitoring device 940, and to analyze the signal and generate an alarm based on the analyzing of the signal. In various embodiments, the central server 990 is configured to receive a second signal indicating a count of the workers 928, and to compare the count of the workers 928 to the monitoring of the workers 928 to determine whether any workers 928 are unaccounted for. For example, after an emergency situation is identified the foreman may conduct a count of workers 928 that have exited the worksite to identify which workers 928, if any, are still unaccounted for and possibly still in the worksite.

Referring to FIGS. 143-152, various aspects of keep out zone system 1010 are shown. Keep out zone system 1010 is substantially the same as keep out zone system 10, keep out zone system 110, keep out zone system 210, or keep out zone system 310 except for the differences discussed herein. Keep out zone system 1010 is configured to monitor of workers and protected areas to detect if a worker is injured. For example, if a worker is injured by a tool or equipment and the worker and/or the tool immediately falls to the ground and does not move, keep out zone system 1010 may detect that event and generate an alarm.

One or more electronic monitoring devices 1040 are arranged around a protected area 1020, such as around a periphery of protected area 1020. Electronic monitoring devices 1040 are substantially the same as electronic monitoring devices 40 except for the differences discussed herein.

In use, worker 1050 can use various tools and/or equipment, such as equipment 1052. Monitoring the worker 1050 and/or equipment 1052 can provide improved safety for both the worker 1050 and the worksite generally.

In various embodiments, keep out zone system 1010 (e.g., via devices 1040) monitors equipment 1052 to determine whether equipment 1052 is being operated in a safe manner. For example, use of equipment 1052 may typically involve being picked up, actively engaged by a worker, then turned off and placed back down to a still position on the floor. Based on that pattern, if keep out zone system 1010 detects that equipment 1052 has experienced a quick change in altitude (drop) and/or a sudden impact (hitting the floor after being dropped), then keep out zone system 1010 may generate an alarm. Stated another way, in various embodiments device 1040 is configured to detect a worker and/or the electric tool falling within the protected area, and to generate a second safety alarm in response to the detection of the falling of the worker and/or the electric tool (e.g., tool 82).

Referring to FIGS. 143-147, various aspects of an exemplary use of keep out zone system 1010 are shown. Initially, a worker 1050 uses equipment 1052 in a protected area 1020 (FIG. 143). Then, keep out zone system 1010 detects that the worker 1050 and/or equipment 1052 has fallen and/or abruptly stopped working (FIG. 144). In certain situations (e.g., based on the severity of the detected fall), keep out zone system 1010 will generate an alarm immediately. Alternatively, keep out zone system 1010 will monitor how much time has passed since the event (FIG. 145), and once a threshold period of time has passed then keep out zone system 1010 will generate an alarm (FIG. 146). In various embodiments, the alarm is a loud sound, a visual signal (e.g., a flashing red light), and/or a networked communication to a remote party. In response to the alarm, one or more people may arrive to help the worker 1050 if he/she requires assistance (FIG. 147).

Referring to FIGS. 148-152, another exemplary use of keep out zone system 1010 is shown. Worker 1050 is using equipment 1052 (FIG. 148) and keep out zone system 1010 detects that that the worker 1050 and/or the equipment 1052 may be lying on the ground and/or have fallen (FIGS. 149-150). In response, an alarm is sent to a remote computing device, such as a central server 1060 via a wireless communication, which logs an event (e.g., a fall event).

In various embodiments, keep out zone system 1010 may alter monitoring functionality in response to detecting an event. For example, if a tool, equipment and/or worker falls or is dropped, keep out zone system 1010 may increase a monitoring rate in the area where the event occurred (e.g., increase resolution of the video and/or audio being captured, increase video frame-rate of monitoring devices, increase audio bandwidth of monitoring devices, and/or change the compression of the data being collected and communicated). As another example, if a tool, equipment and/or worker falls or is dropped, keep out zone system 1010 may flag a time-stamp in a database of stored events, and keep out zone system 1010 may display a particular camera on a display that is known to be monitored (e.g., in front of a safety monitoring individual). As another example, if a tool, equipment and/or worker falls or is dropped, keep out zone system 1010 may alter thresholds for detecting events (e.g., in response to detecting a fall event of equipment 1052, keep out zone system 1010 may initiate an alarm if it is detected that worker 1050 does not move within a reduced time frame, such as two seconds).

In various embodiments central server 1060 cross references the location of equipment 1052 with any workers in the same zone (e.g., in the same protected area 1020). Subsequently, central server 1060 forwards the alarm to a personal device 1080 (e.g., cell phone) of a person associated with the protected area 1020, such as a safety monitoring individual 1070 (FIG. 151), who then arrives to help (FIG. 152).

Referring to FIGS. 153-160, various aspects of keep out zone system 1110 are shown. Keep out zone system 1110 is substantially the same as keep out zone system 10, keep out zone system 110, keep out zone system 210, keep out zone system 310, or keep out zone system 1010 except for the differences discussed herein. Keep out zone system 1110 is directed at dynamically monitoring workers within and protected area(s), thereby enabling a quicker and more accurate response when detecting an emergency event. For example, if a fire is detected and the worksite needs to be evacuated, keep out zone system 1110 will provide an updated and accurate count and/or location of workers on the worksite to help managers confirm the worksite has been fully evacuated.

Figure 153:
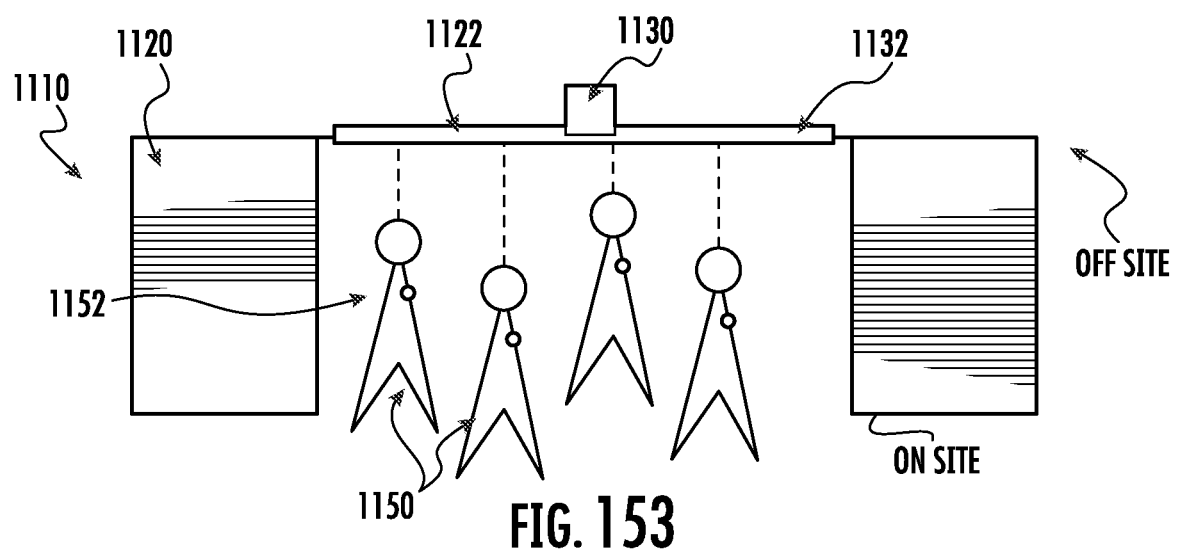
FIGS. 153-160 provide details regarding various aspects and embodiments related to a safety monitoring system.
Figure 154:
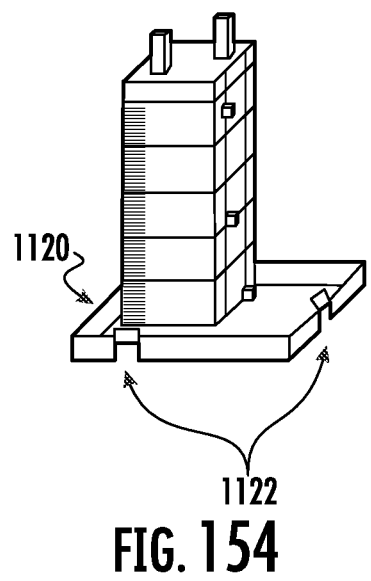
Figure 155:
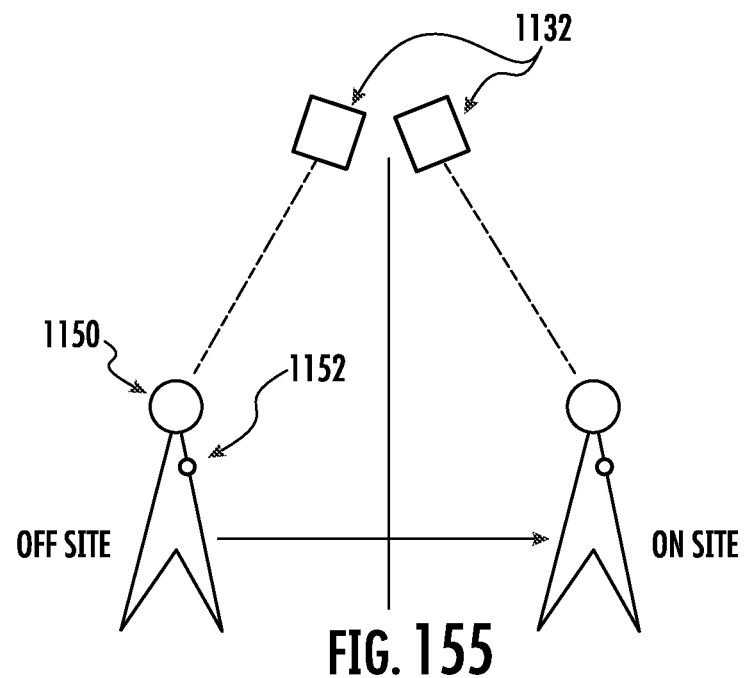
Figure 156:
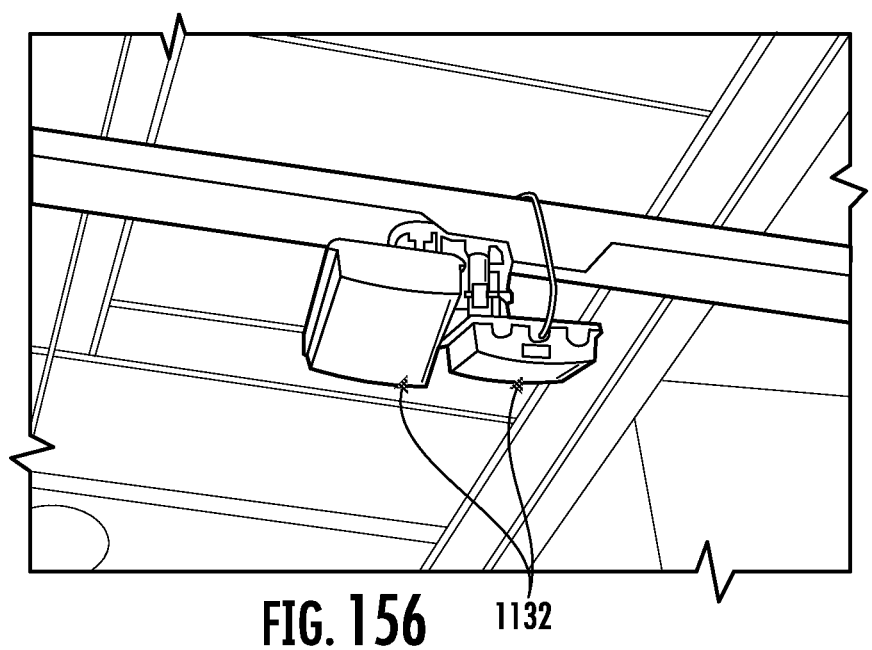
Figure 157:
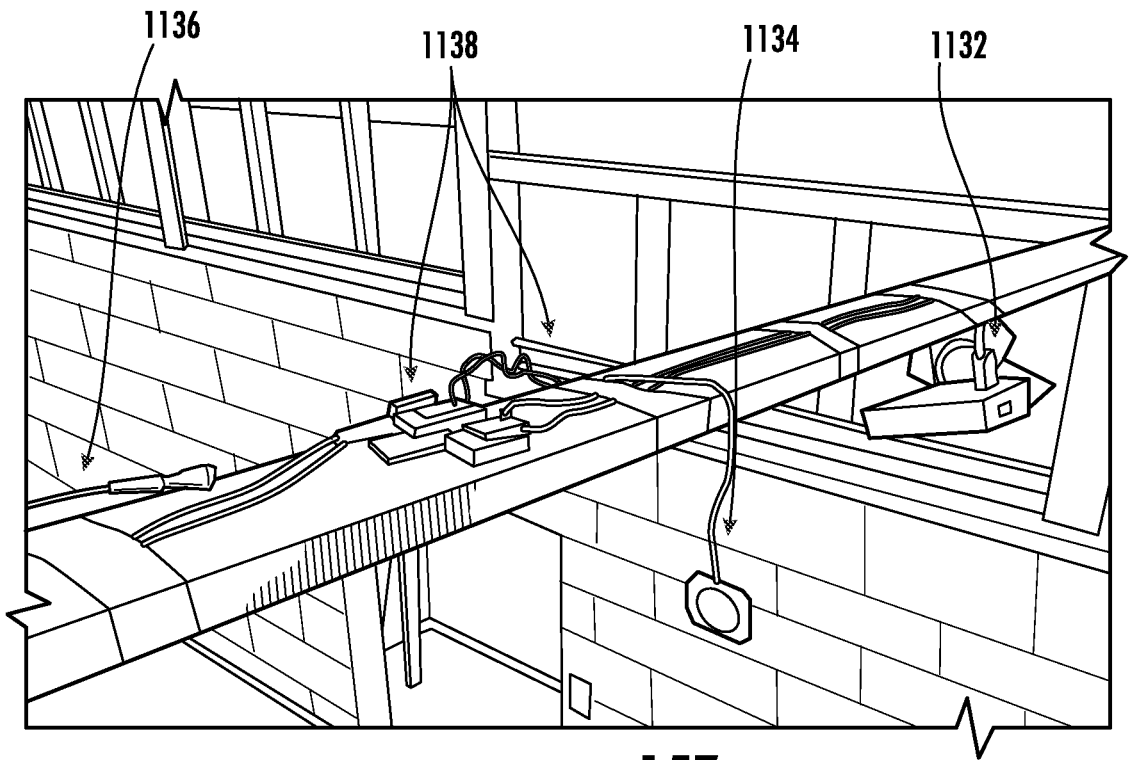

Referring to FIGS. 153-154, keep out zone system 1110 includes a periphery 1120 around a worksite, such as a fence around the worksite. One or more gates 1122 within the periphery 1120 permit workers 1150 to enter and exit the worksite.

Referring to FIGS. 153-158, as workers 1150 enter or exit the worksite, one or more technologies, shown as detecting system 1130, detecting system 1132, and/or camera 1140, track the events. In various embodiments, detecting system 1130 tracks whether workers 1150 are entering or exiting the worksite, and detecting system 1132 identifies and/or authenticates the workers 1150 (e.g., the trade and/or company of the respective workers 1050), such as via personal ID 1152 on the workers 1150 that personally identifies each worker 1150. In various embodiments, personal ID 1152 is a UHF passive sticker tag that corresponds to various information about worker 1050 (e.g., personal ID 1152 holds the trade of the worker, the company of the worker, the training of the worker, etc.). In various embodiments, camera 1140 is USB-compatible and transmits the data and/or images collected.

In various embodiments, detecting system 1132 includes two UHF RFID antennas aimed in different directions to determine the movement of personal ID 1152 past gate 1122. Detecting system 1132 transmits the collected data, such as to electronics 1138, which receives the RFID information to authenticate the workers 1150. In various embodiments, electronics 1138 is an electronic board configured to detect RFID signals for authentication of workers.

Figure 158:
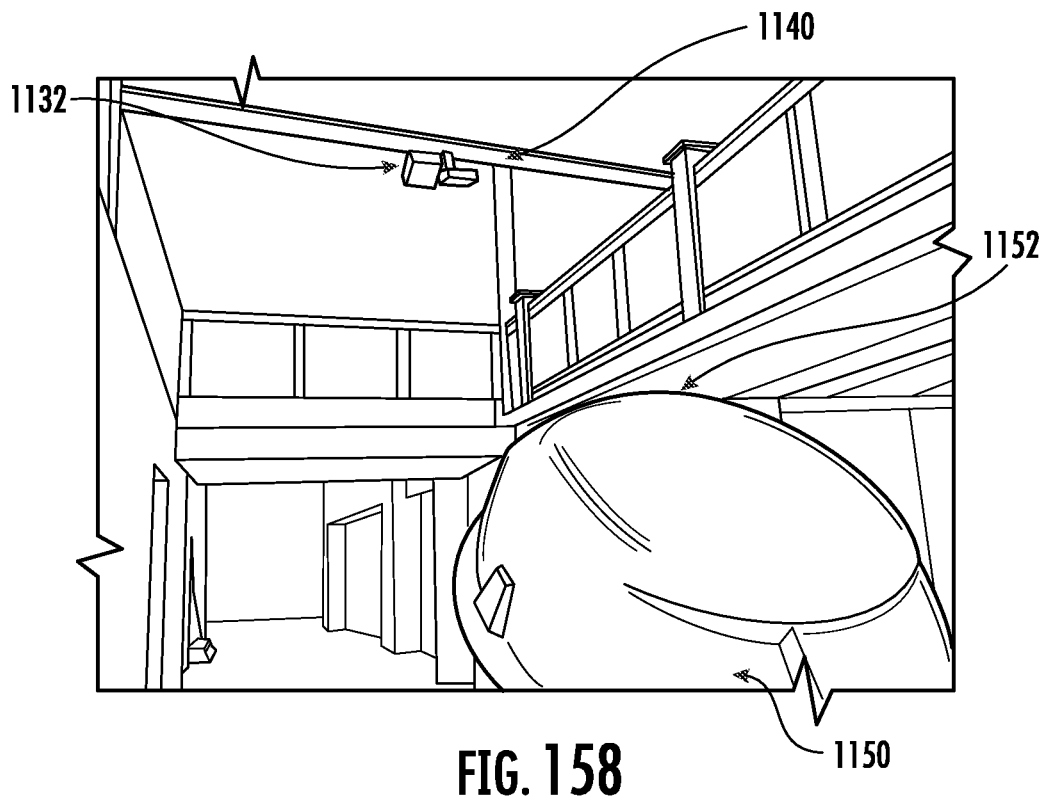

Referring to FIG. 158, one or more of gates 1122 include an indicator, such as a light-emitting device 1134, that indicates in real-time whether a worker 1150 is authenticated (e.g., light-emitting device 1134 flashes a green light for each worker that was authenticated and light-emitting device 1134 flashes a red light if a person was detected transiting the gate without being authenticated). One or more of detecting system 1130 and detecting system 1132 communicates data being monitored via a communication channel, shown as wire 1136.

Figure 159:
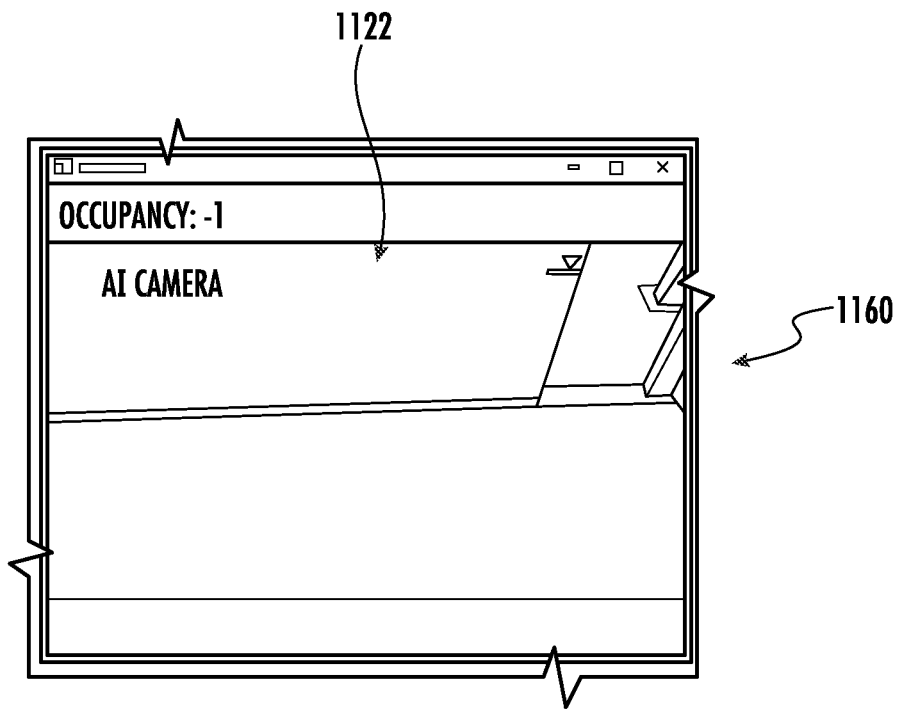
Figure 160:
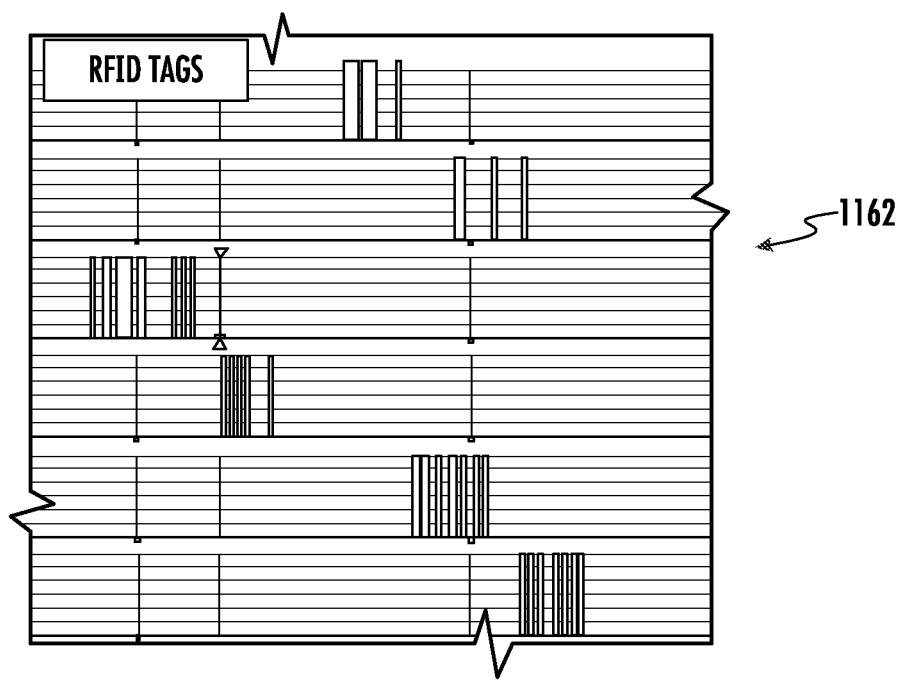

Referring to FIGS. 159-160, image 1160 from a camera is shown. The image 1160 is located at a gate 1122. In various embodiments, one or more detecting systems of keep out zone system 1110 detect and/or store RFID signals 1162 as workers transit the gate 1122.

In various embodiments, workers 1150 are detected via camera 1140 that includes analytical functionality (e.g., Artificial Intelligence), TMOS, PIR (passive infrared), analysis of photoelectric signals, an IR camera, LiDAR (light detection and ranging), and/or time-of-flight (e.g., measuring time for an object to transit a distance). In various embodiments, workers 1150 are authenticated using UHF RFID (ultra-high frequency radio frequency identification), Bluetooth, BLE (bluetooth low energy), UWB (ultra wideband), Barcode/Fiducial indicators, scanning badges, facial recognition, etc.

It should be understood that the figures illustrate the exemplary embodiments in detail, and it should be understood that the present application is not limited to the details or methodology set forth in the description or illustrated in the figures. It should also be understood that the terminology is for description purposes only and should not be regarded as limiting.

Further modifications and alternative embodiments of various aspects of the disclosure will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present disclosure.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred. In addition, as used herein, the article "a" is intended to include one or more component or element, and is not intended to be construed as meaning only one. As used herein, "rigidly coupled" refers to two components being coupled in a manner such that the components move together in a fixed positional relationship when acted upon by a force.

Various embodiments of the disclosure relate to any combination of any of the features, and any such combination of features may be claimed in this or future applications. Any of the features, elements or components of any of the exemplary embodiments discussed above may be utilized alone or in combination with any of the features, elements or components of any of the other embodiments discussed above.

For purposes of this disclosure, the term "coupled" means the joining of two components directly or indirectly to one another. Such joining may be stationary in nature or movable in nature. Such joining may be achieved with the two members and any additional intermediate members being integrally formed as a single unitary body with one another or with the two members or the two members and any additional member being attached to one another. Such joining may be permanent in nature or alternatively may be removable or releasable in nature.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above.

In various exemplary embodiments, the relative dimensions, including angles, lengths and radii, as shown in the Figures are to scale. Actual measurements of the Figures will disclose relative dimensions, angles and proportions of the various exemplary embodiments. Various exemplary embodiments extend to various ranges around the absolute and relative dimensions, angles and proportions that may be determined from the Figures. Various exemplary embodiments include any combination of one or more relative dimensions or angles that may be determined from the Figures. Further, actual dimensions not expressly set out in this description can be determined by using the ratios of dimensions measured in the Figures in combination with the express dimensions set out in this description.

What is claimed is:

1. A safety monitoring system comprising:
   a first device configured to generate an alert providing an indication of a protected area on a construction site, wherein the alert comprises audio and/or visual elements;
   a second device configured to generate an electronic signal in response to detecting an intrusion to the protected area; and
   a third device remote from the second device, the third device configured to receive a notification that the intrusion was detected in the protected area.

2. The safety monitoring system of claim 1, the second device configured to emit a laser along a periphery of the protected area.

3. The safety monitoring system of claim 2, the first device comprising a detector configured to detect the laser.

4. The safety monitoring system of claim 1, comprising:
   a personal electronic device; and
   a wire extending between the first device and the second device, the wire configured to emit a radio signal that is detected by the personal electronic device, wherein the personal electronic device is configured to emit a warning signal as a result of detecting the radio signal.

5. The safety monitoring system of claim 1, comprising an elongate structure extending between the first device and the second device, wherein the second device is configured to monitor a length and/or a tension of the elongate structure.

6. The safety monitoring system of claim 1, the second device comprising an accelerometer, wherein the detecting the intrusion to the protected area is a result of receiving a signal from the accelerometer.

7. The safety monitoring system of claim 1, wherein the third device is remote from the protected area.

8. The safety monitoring system of claim 1, wherein the electronic signal received by the third device comprises a text message.

9. The safety monitoring system of claim 8, wherein the notification comprises the text message.

10. The safety monitoring system of claim 8, wherein the text message comprises information identifying an intruder that caused the intrusion.

11. The safety monitoring system of claim 1, the third device comprising a hard hat.

12. The safety monitoring system of claim 11, the hard hat comprising a lighting element configured to emit a light in response to receiving the notification that the intrusion was detected in the protected area.

13. The safety monitoring system of claim 11, the hard hat comprising a haptic element configured to vibrate in response to receiving the notification that the intrusion was detected in the protected area.

14. A safety monitoring system comprising:
a first device configured to generate an electronic signal in response to detecting an intrusion to a protected area on a construction site; and
an electric tool configured to:
receive a notification that the intrusion was detected in the protected area; and
generate a safety alarm in response to the detection of the intrusion.

15. The safety monitoring system of claim 14, wherein the electric tool is configured to disable a functionality in response to the detection of the intrusion.

16. The safety monitoring system of claim 14, comprising a second device configured to detect a worker and/or the electric tool falling within the protected area, and to generate a second safety alarm in response to the detection of the falling of the worker and/or the electric tool.

17. A safety monitoring system comprising:
a first monitoring device configured to measure an atmospheric condition, to monitor the presence of a worker within a protected area on a construction site, and to generate a notification indicating the measurement of the atmospheric condition and the presence of the worker; and
a central server configured to:
receive the notification from the first monitoring device;
analyze the notification; and
transmit an alarm to the worker in response to the analyzing of the notification.

18. The safety monitoring system of claim 17, the central server configured to transmit a second alarm to a second worker in response to analyzing the notification and in response to receiving data that the second worker is in the protected area.

19. The safety monitoring system of claim 17, wherein the notification indicating the measurement of the atmospheric condition and the presence of the worker comprises a first signal indicating the measurement of the atmospheric condition and a second signal indicating the presence of the worker.

20. A method for monitoring a safety zone at a construction site comprising:
receiving a first signal indicating a first number of people in a protected area on a construction site;
receiving a second signal indicating the occurrence of an emergency event that corresponds to the protected area;
receiving a third signal indicating a second number of the people that were in the protected area; and
determining whether the protected area is evacuated by comparing the first number to the second number.

21. The method of claim 20, comprising counting the second number of the people that were in the protected area via a personal electronic device scanning ID devices of each of the second number of the people.

* * * * *